(12) United States Patent
Thorson et al.

(10) Patent No.: US 9,879,043 B1
(45) Date of Patent: Jan. 30, 2018

(54) SYNTHESIS OF NON-NATURAL COFACTOR ANALOGS OF S-ADENOSYL-L-METHIONINE USING METHIONINE ADENOSYLTRANSFERASE

(71) Applicant: University of Kentucky Research Foundation, Lexington, KY (US)

(72) Inventors: Jon Thorson, Lexington, KY (US); Tyler Huber, Lexington, KY (US); Jianjun Zhang, Lexington, KY (US); Shanteri Singh, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 323 days.

(21) Appl. No.: 14/298,874

(22) Filed: Jun. 6, 2014

Related U.S. Application Data

(60) Provisional application No. 61/832,038, filed on Jun. 6, 2013.

(51) Int. Cl.
| | |
|---|---|
| C07H 19/16 | (2006.01) |
| C12P 19/28 | (2006.01) |
| C12P 13/12 | (2006.01) |
| C12P 11/00 | (2006.01) |
| C12P 9/00 | (2006.01) |
| C12Q 1/48 | (2006.01) |
| C12P 19/40 | (2006.01) |
| C07D 405/14 | (2006.01) |
| C12P 17/18 | (2006.01) |

(52) U.S. Cl.
CPC ........... *C07H 19/16* (2013.01); *C07D 405/14* (2013.01); *C12P 17/188* (2013.01); *C12P 19/40* (2013.01)

(58) Field of Classification Search
CPC ........ C07H 19/16; C12N 9/10; C07C 328/58; C12Q 1/48; C12P 19/40
See application file for complete search history.

(56) References Cited

PUBLICATIONS

J. K. Coward, E. P. Slisz, J. Med. Chem. 1973, 16, 460-463.
Hoffman, J.L. (1986). Chromatographic analysis of the chiral and covalent instability of S-adenosyl-L-methionine. Biochemistry 25, 4444-4449.
K. Islam, W. Zheng, H. Yu, H. Deng, M. Luo, Expanding Cofactor Repertoire of Protein Lysine Methyltransferase for Substrate Labeling, ACS Chem. Biol. 2011, 6, 679-684.
I. R. Bothwell, K. Islam, Y. Chen, W. Zheng, G. Blum, H. Deng, M. Luo, Bioorthogonal Profiling of Protein Methylation Using Azido Derivative of S-Adenosyl-L-methionine, J. Am. Chem. Soc. 2012, 134, 5905-5912.
D. F. Iwig, S. J. Booker, Biochemistry, 2004, 43, 13496-13509.
D. F. Iwig, A. T. Grippe, T. A. McIntyre, S. J. Booker, Biochemistry, 2004, 43, 13510-13524.
J. Jiracek, M. Collinsova, I. Rosenberg, M. Budesinsky, E. Protivinska, H. Netusilova, T. A. Garrow, J. Med. Chem. 2006, 49, 3982-3989.
D. K. Liscombe, G. V. Louie, J. P. Noel, Nat. Prod. Rep. 2012, 29, 1238-1250.
Z. J. Lu, G. D. Markham, J. Biol. Chem. 2002, 277, 16624-16631.
S. C. Lu, J. M. Mato, Physio. Rev. 2012, 92, 1515-1542.
Markham, G.D., and Pajares, M.A. (2009). Structure-function relationships in methionine adenosyltransferases. Cellular and molecular life sciences : CMLS 66, 636-648.
O. M. Ottink, F. H. Nelissen, Y. Derks, S. S. Wijmenga, H. A. Heus, Anal. Biochem. 2010, 396, 280-283.
K. Sato, M. Hirayama, Synthetic Studies of the Derivatives of Acetylene. I. Reactions of 5-Bromopent-3-en-l-yne1), Bull. Chem. Soc. Jpn. 1969, 42, 2589-2592.
T. Shiraiwa, K. Nakagawa, N. Kanemoto, T. Kinda, H. Yamamoto, Chem. Pharm. Bull. 2002, 50, 1081-1085.
H. Stecher, M.Tengg, B. J. Ueberbacher, P. Remler, H. Schwab, H. Griengl, M. Gruber-Khadjawi, Angew. Chem. Int. Ed. Engl. 2009, 48, 9546-9548.
Wang, R., Islam, K., Liu, Y., Zheng, W., Tang, H., Lailler, N., Blum, G., Deng, H., and Luo, M. (Jan. 2013). Profiling genome-wide chromatin methylation with engineered posttranslation apparatus within living cells. Journal of the American Chemical Society 135, 1048-1056.
R. Wang, W. Zheng, H. Yu, H. Deng, M. Luo, J. Am. Chem. Soc. 2011, 133, 7648-7651.
N. Yarlett, J. Garofalo, B. Goldberg, M. A. Ciminelli, V. Ruggiero, J. R. Sufrin, C. J. Bacchi, Biochim. Biophys. Acta 1993, 1181, 68-76.
Y. Yi, S. X. Fa, W. Cao, L. W. Zeng, M. X. Wang, H. P. Xu, X. Zhang, Chem. Commun. 2012, 48, 7495-7497.
Zhang, C.; Weller, R. L.; Thorson, J. S.; Rajski, S. R. Journal of the American Chemical Society 2006, 128, 2760-1.
Z. S. Zhou, E. Smith, R. G. Matthews, Bioorg. Med. Chem. Lett. 2000, 10, 2471-2475.

*Primary Examiner* — Lawrence E Crane
(74) *Attorney, Agent, or Firm* — Stites & Harbison PLLC; Sean P. Ritchie

(57) ABSTRACT

The present disclosure relates to the synthesis of non-natural analogs of S-adenosyl-L-methionine (SAM) and/or of Se-adenosyl-L-methionine (SeAM) by reacting a methionine analog and adenosine triphosphate (ATP) in the presence of at least one methionine adenosyltransferase (MAT), and to use thereof with downstream SAM and/or SeAM utilizing enzymes. The non-natural analogs of SAM and/or SeAM have the general formula:

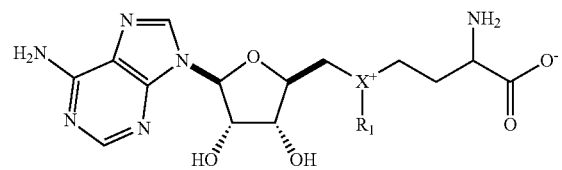

where X is S or Se, and $R_1$ is an alkyl group.

13 Claims, 13 Drawing Sheets

SYNTHESIS OF NON-NATURAL COFACTOR ANALOGS OF S-ADENOSYL-L-METHIONINE USING METHIONINE ADENOSYLTRANSFERASE

RELATED APPLICATION

This application claims priority from U.S. Provisional Patent Application No. 61/832,038, filed Jun. 6, 2013, the entire disclosure of which is incorporated herein by this reference.

TECHNICAL FIELD

The presently-disclosed subject matter generally relates to the synthesis of non-natural cofactor analogs of S-adenosyl-L-methionine (SAM) and/or of Se-adenosyl-L-methionine (SeAM) and to the various use(s) thereof.

INTRODUCTION

Methionine adenosyltransferase (MAT) is a family of enzymes that utilizes adenosine triphosphate (ATP) and methionine as substrates to produce S-adenosyl-L-methionine (SAM or AdoMet), a methyl donor in the biological methylation of biomolecules and bioactive natural products. (FIG. 1) [42]. The reaction occurs in an unusual two-step mechanism in which the adenosyl group is transferred from ATP to the sulfur atom of methionine, cleaving the triphosphate, and the triphosphate is subsequently hydrolyzed to PPi and Pi [45].

MAT is present in all living organisms, from bacteria to mammals. To date, MAT structures from *E. coli* [40], *Thermococcus kodakarensis* [48], *Burkholderia pseudomallei* (PDB code 3IML), *Entamoeba histolytica* (PDB code 3SO4), *Mycobacterium marinum* (PDB code 3RV2), *Mycobacterium avium* (PDB code 3S82), *Mycobacterium tuberculosis* (PDB code 3TDE), *Rattus norvegicus* [36] and *Homo sapiens* [50] have been solved. They are more than 50% identical to one other and share several common features: (i) they usually appear as oligomeric proteins with a highly conserved three-domain fold [43]; (ii) divalent cations such as $Mg^{2+}$ are required for activity and monovalent cations such as $K^+$ is able to enhance the reaction rate [44]; (iii) a flexible loop suspended above the active site, serves as a "gate" and is involved in the catalytic activity of the enzyme [34].

Moreover, some specific analogs of SAM bearing alternative alkyl substitution for the native methyl group have been successfully used in vitro for the methyltransferase-catalyzed alkylation of natural products [57], DNA [58], and proteins [59]. While these recent studies suggest MTases tolerate alternative SAM alkyl donors, the methods proposed in such studies remain impractical due to a number of key factors. For example, previously known synthetic routes to SAM analogs are multistep strategies that suffer from poor overall yields and difficult purification protocols. In addition, the corresponding SAM analogs are often highly labile and are unable to pass through the cell membranes. Accordingly, there is a need in the art for a simple method of providing improved non-natural SAM analogs.

BRIEF SUMMARY

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of features.

In some embodiments, the present disclosure is directed to the synthesis of non-natural L-methionine and/or L-selenomethionine analogs and to uses thereof. Accordingly, in certain embodiments, the present disclosure provides compounds of the Formula II:

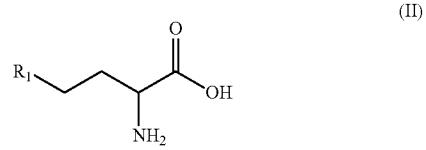

wherein $R_1$ is any alkyl group. In certain embodiments, $R_1$ comprises a propyl group, an allyl group, an aryl group and/or a propargyl group. Further, in some embodiments, $R_1$ is selected from the group consisting of

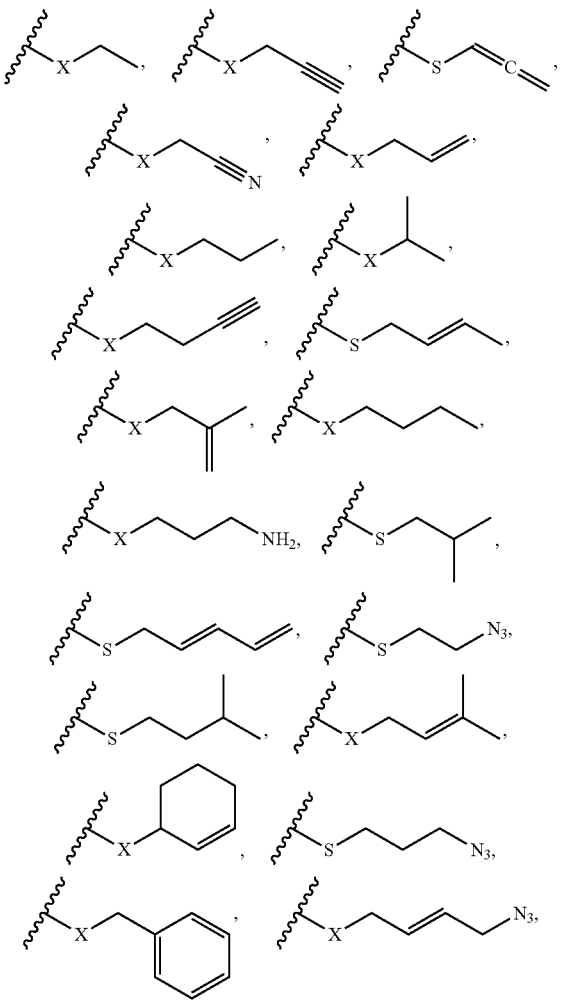

-continued

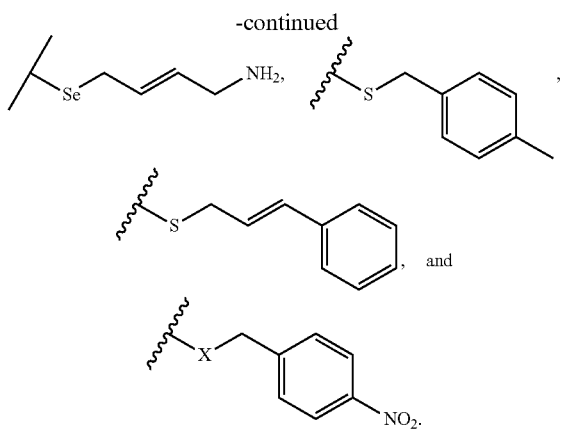

And in some embodiments, X is selected from the group consisting of S and Se. In still further embodiments, $R_1$ is selected from the group consisting of

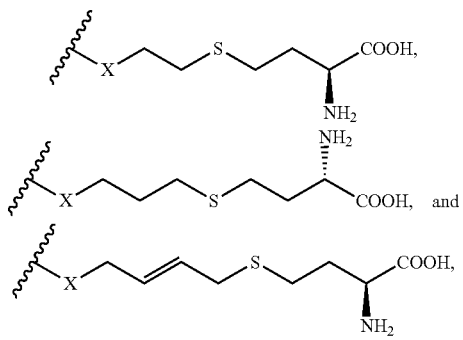

and X may be S.

In some embodiments, the present disclosure is directed to the synthesis of non-natural cofactor analogs of S-adenosyl-L-methionine (SAM) and/or Se-adenosyl-L-methionine (SeAM) using methionine adenosyltransferase and to uses of the non-natural SAM and/or SeAM analogs. Accordingly, in some embodiments, the present disclosure provides a SAM analog and/or a SeAM analog of the Formula I:

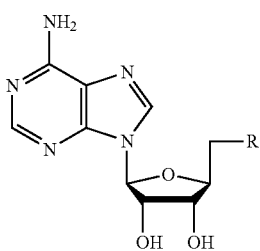

(I)

wherein R is a compound according to Formula II and wherein R is attached through an S or Se atom and/or through the X atom. In certain embodiments, R comprises methionine-tetrazole.

Further, the present disclosure also provides, in certain embodiments, methods of producing an S-adenosyl-L-methionine analog and/or a Se-adenosyl-L-methionine (SeAM) analog, comprising at least the step of reacting a first substrate with a second substrate in the presence of a methionine adenosyltransferase (MAT).

Likewise, the present disclosure provides, in some embodiments, methods of producing an indolocarbazole analog. Such methods comprise the step of reacting a first substrate with a second substrate in the presence of a methionine adenosyltransferase (MAT).

In some embodiments of the methods provided herein, the first substrate comprises a compound according to Formula II, the second substrate comprises adenosine triphosphate (ATP) and/or the MAT comprises at least one of human MAT II catalytic alpha and regulatory beta subunit (hMAT2), human MAT II catalytic alpha subunit alone (hMAT2A), human MAT I catalytic subunit alpha (hMAT1A), *Escherichia coli* MAT (eMAT), *Sulfolobus solfataricus* MAT (sMAT), and *Methanocaldococcus jannaschii* MAT (mMAT). Additionally, the present disclosure provides that any of the methods described herein may be conducted in one pot, i.e., in a single vessel.

The present disclosure further presents a method for production of a chemical library, the method comprising at least the step of reacting a plurality of compounds according to Formula II with ATP in the presence of at least one MAT to obtain at least one non-natural compound. In some embodiments, the at least one non-natural compound is a SAM analog and/or a SeAM analog.

Furthermore, the present disclosure also provides, in certain embodiments, a method of producing a SAM analog by reacting a first substrate comprising methionine-tetrazole with a second substrate in the presence of at least one methionine adenosyltransferase (MAT). Moreover, in some embodiments, the second substrate comprises ATP. And in some embodiments, the MAT comprises at least one of human MAT II catalytic alpha and regulatory beta subunit (hMAT2), human MAT II catalytic alpha subunit alone (hMAT2A), human MAT I catalytic subunit alpha (hMAT1A), *Escherichia coli* MAT (eMAT), *Sulfolobus solfataricus* MAT (sMAT), and *Methanocaldococcus jannaschii* MAT (mMAT).

In some embodiments, the present disclosure provides a method for producing a natural product analog, comprising: (i) reacting a methionine analog and at least one methionine adenosyltransferase to produce an S-adenosyl-L-methionine analog in a vessel; (ii) providing at least one methyl transferase and at least one natural product in the vessel; and (iii) alkylating the natural product in the presence of the methyl transferase and the S-adenosyl-L-methionine analog to produce a natural product analog in the vessel. In some embodiments, the methionine analog is a compound according to Formula II, as described herein. And in certain embodiments, S-adenosyl-L-homocysteine hydrolase is also provided in the vessel.

Na, NH$_3$, −78° C. with 1 or 1-Se; (ii) K$_2$CO$_3$, acetone with 1-Hcy; (iii) NaBH$_4$/NaOH, H$_2$O, THF, 5 h with 1-Se; (iv) HCl, Reflux with 2-Se (see Table 1).

Figure 5:
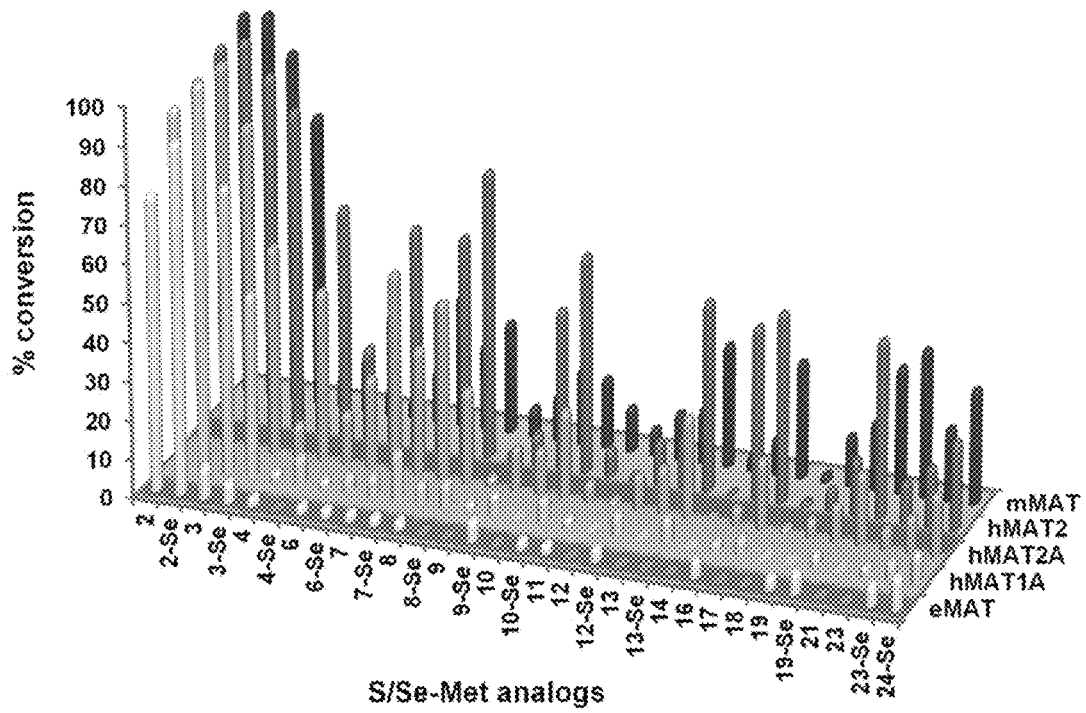

FIG. 5 illustrates the turnover of S/Se-Met analogs to the corresponding S(Se)AM analogs catalyzed by selected MATs based upon reverse phase high performance liquid chromatography (RP-HPLC) (average percent error≤5%). Notably, no product formation was observed in the absence of MAT, S/Se-Met analogs or ATP.

Figure 6:
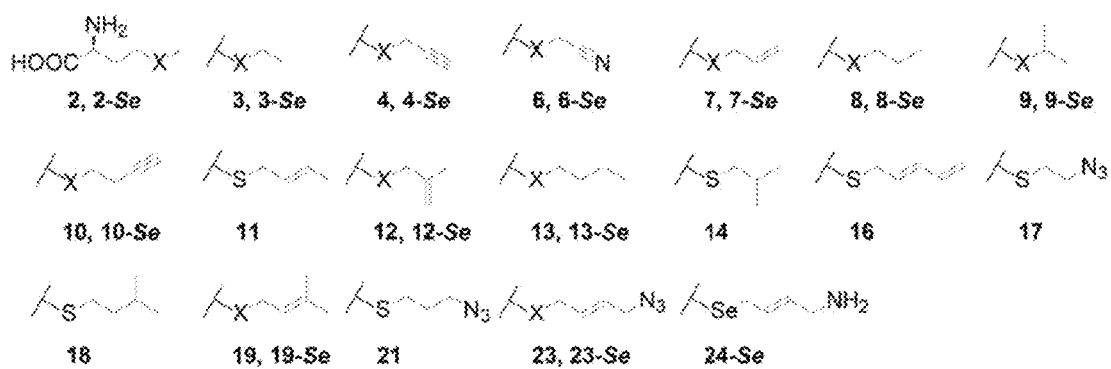

FIG. 6 provides the structures of the S/Se-Met analogs listed in FIG. 5 (X=S, Se).

Figure 7:
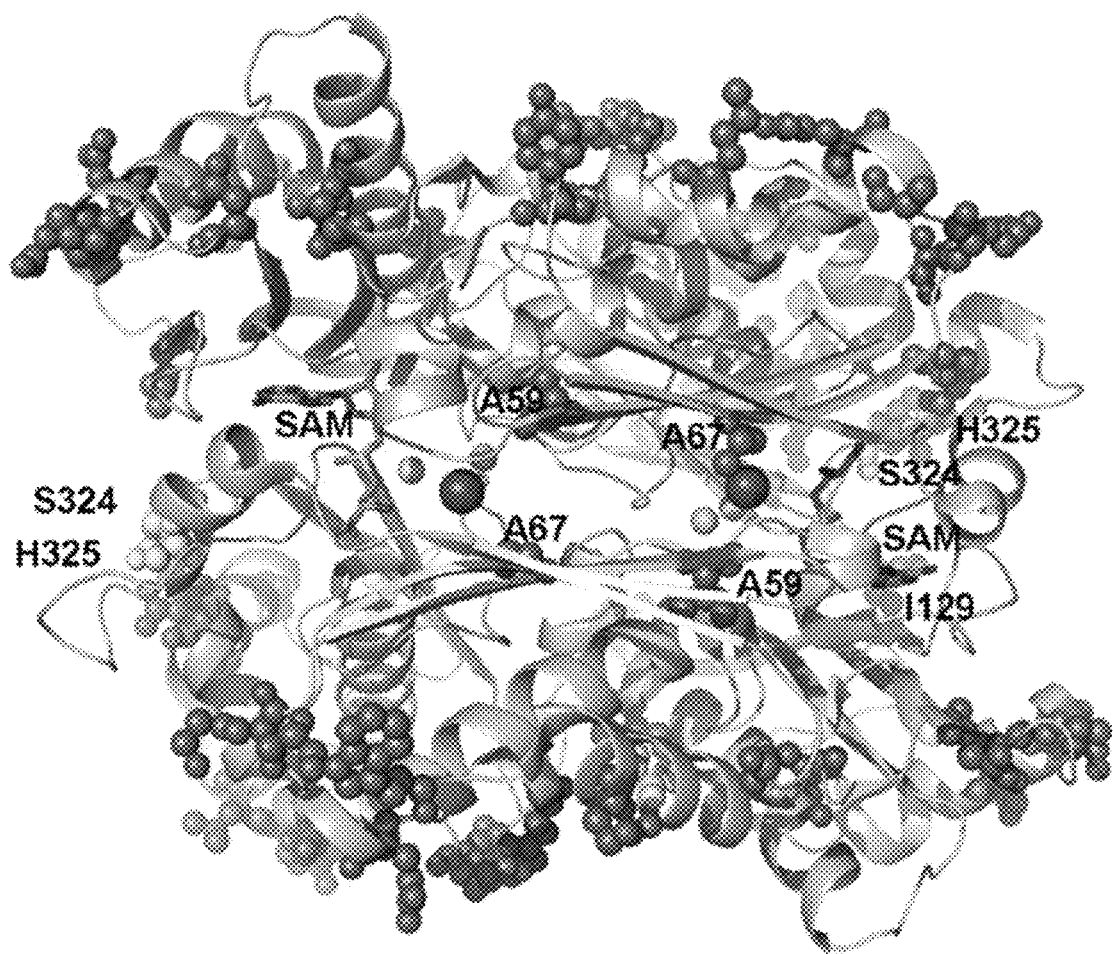

FIG. 7 presents mapping of residue positions that differ among eMAT (Protein Data Bank (PDB) ID:1RG9), hMAT2A (PDB ID:2PO2) and hMAT1A (PDB ID:2OBV) on the hMAT2A homodimeric structure. Conserved residues among all three MATs are indicated by grey ribbons; residues that differ among all three MATs are highlighted as ball and stick models; and conserved residues among 'stringent' MATs (hMAT1A and eMAT) which differ from the more permissive hMAT2A are highlighted by lighter-colored ball and stick models.

Figure 8:
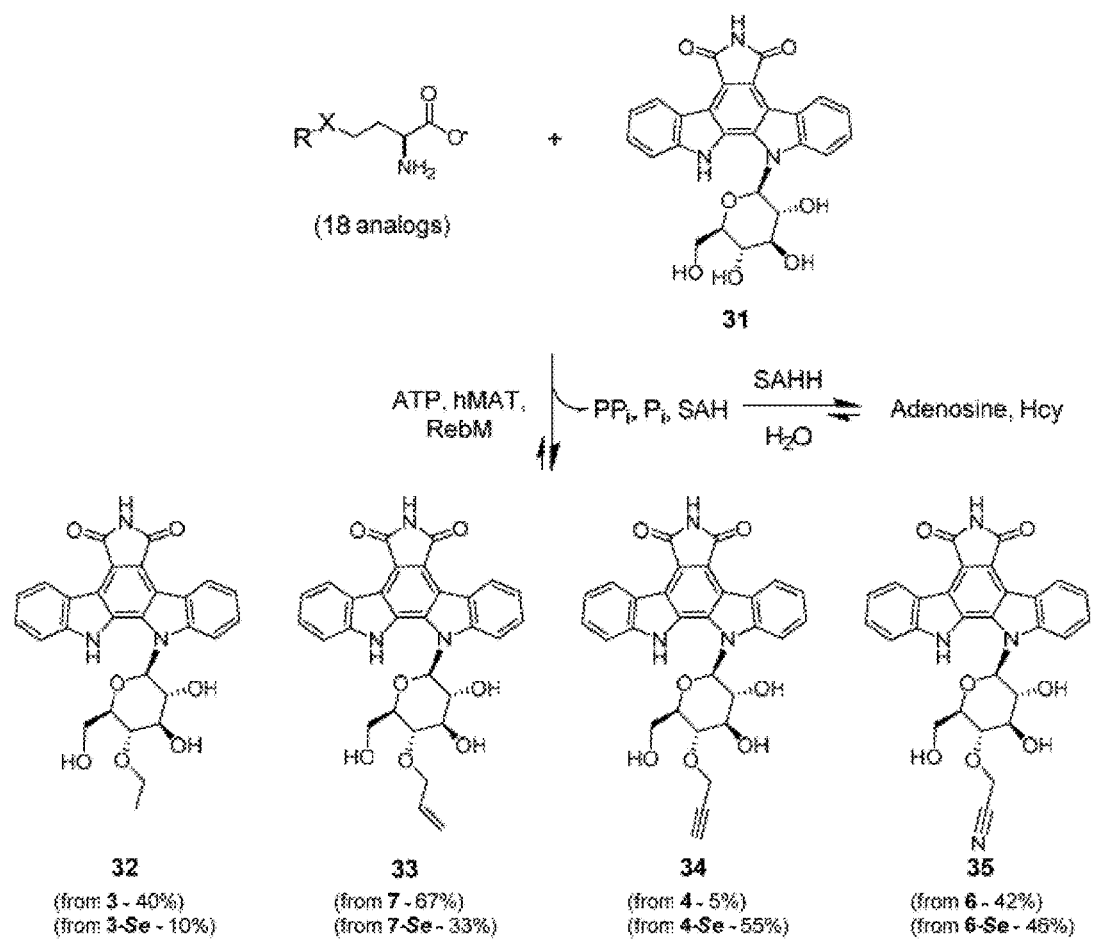

FIG. 8 provides the products of hMAT2A-RebM coupled reaction in the presence of 3/3-Se, 7/7-Se, 4/4-Se, and 6/6-Se (see FIG. 5, FIG. 6). The percent product formation is noted in parentheses based upon the S/Se-Met analogs utilized (average percent error≤5%).

Figure 9:
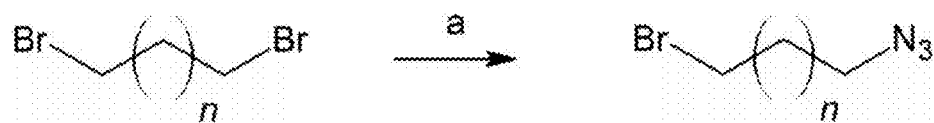
Figure 10:
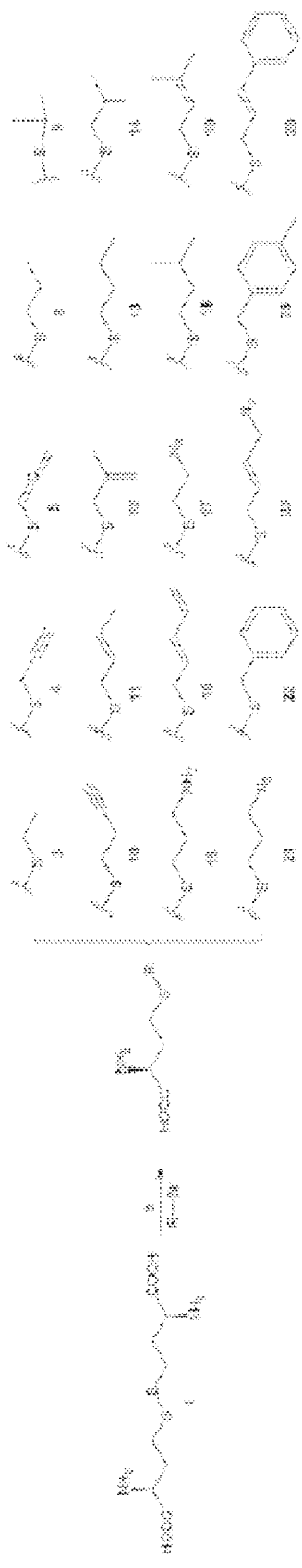

FIG. 9 shows the synthesis of S/Se-alkylated L-methionine analogs, when "a" is NaN$_3$, nBu$_4$NHSO$_4$, NaHCO$_3$ (sat)/CH$_2$Cl$_2$;

FIG. 10 shows the synthesis of S/Se-alkylated L-methionine analogs, when "b" is Na, NH$_3$, −78° C.

Figure 11:

FIG. 11 shows the synthesis of S/Se-alkylated L-methionine analogs, when "c" is K$_2$CO$_3$, acetone.

Figure 12:

FIG. 12 shows the synthesis of S/Se-alkylated L-methionine analogs, when "b" is Na, NH$_3$, −78° C.

Figure 13:
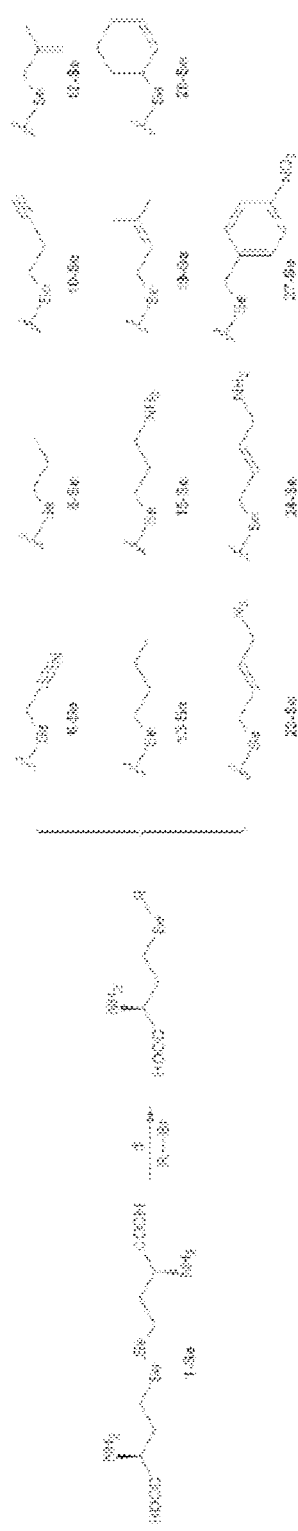

FIG. 13 shows the synthesis of S/Se-alkylated L-methionine analogs, when "d" is NaBH$_4$/NaOH, H$_2$O, THF, rt (room temperature), 5 h.

Figure 14:

FIG. 14 shows the synthesis of S/Se-alkylated L-methionine analogs, when "e" is HCl, reflux.

Figure 15:
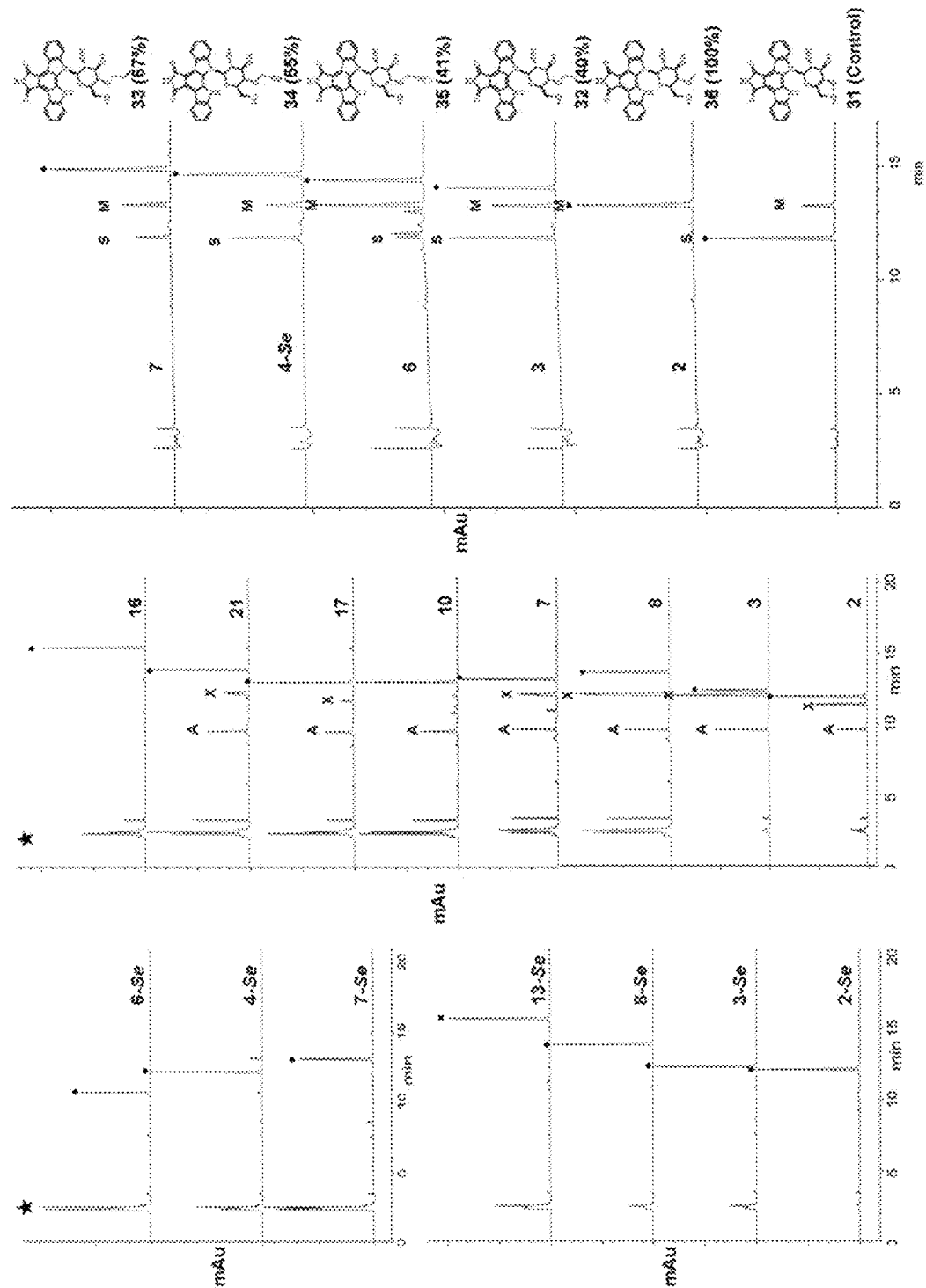

FIG. 15 provides high performance liquid chromatography (HPLC) traces for representative reactions. The first column (left/bottom) provides representative reactions (Method D) catalyzed by hMAT2 illustrating the production of Se-SAM analogs (denoted by a black dot) in the presence of a select set of L-SeMet analogs. Starting material (ATP) is designated by a star. The second column (middle) provides representative reactions (Method D) catalyzed by hMAT2 illustrating the production of SAM analogs (denoted by a black dot) and/or 5'-methyl-thio-5'-deoxyadenosine (MTA, designated by a 'X') in the presence of a select set of L-Met analogs. Starting material (ATP) is designated by a star and the SAM degradation product, adenine, is labeled with an 'A'. The third column (right/top) provides representative hMAT/RebM coupled reactions (Method E) where the peaks corresponding to differentially alkylated products are highlighted by the black dot and peaks at 'S' and 'M' correspond to the remaining substrate and methylated products, respectively. A small amount of methylated product is formed in the control lacking L-Met/L-Met analog (bottom panel), suggesting purified hMAT2 and/or RebM retains a small amount of residual L-Met and/or SAM. For all chromatograms illustrated, numbers within each correspond to the Se-Met or S-Met analogs utilized.

Figure 16:
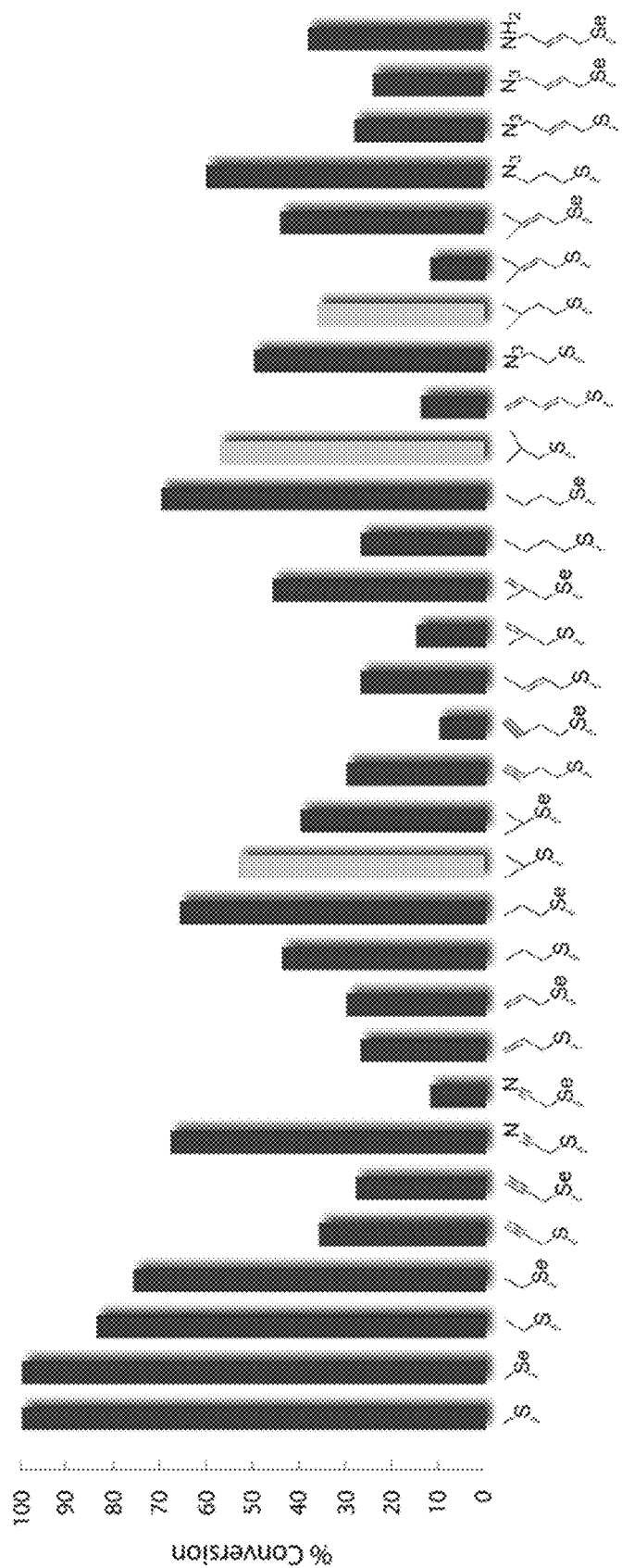

FIG. 16 illustrates the turnover of S/Se-Met analogs to the corresponding S(Se)AM analogs catalyzed by sMAT based upon RP-HPLC (average percent error≤5%, see Table 4).

Light-colored bars (referring to branched L-alkyl-substituted analogs) denote analogs for which only trace turnover was observed with MATs studied to date. As controls, no product formation was observed in the absence of sMAT, S/Se-Met analogs or ATP.

Figure 17:
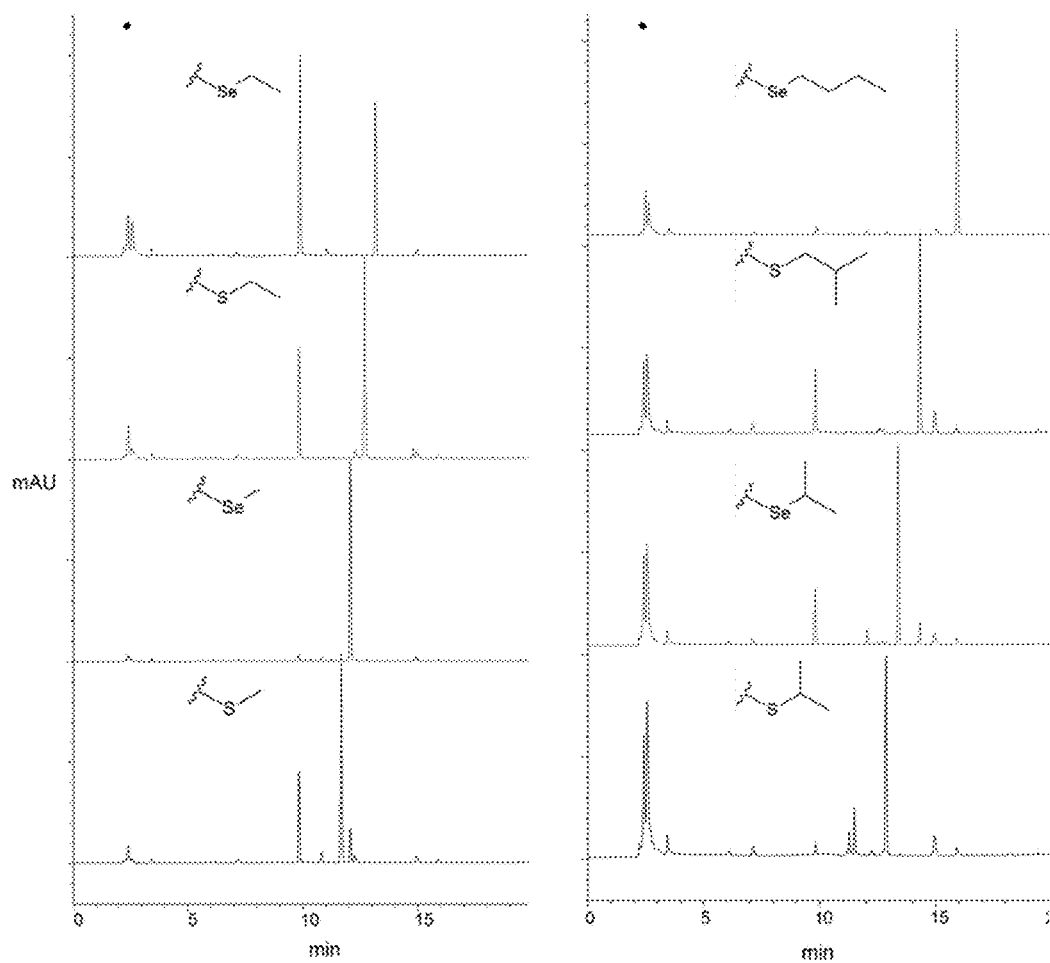

FIG. 17 provides HPLC traces for representative sMAT reactions illustrating the production of SAM analogs and/or 5'-methyl-thio(seleno)-5'-deoxyadenosine (MTA) in the presence of a select set of L-Met analogs. Starting material (ATP) is designated by a dot.

Figure 18:
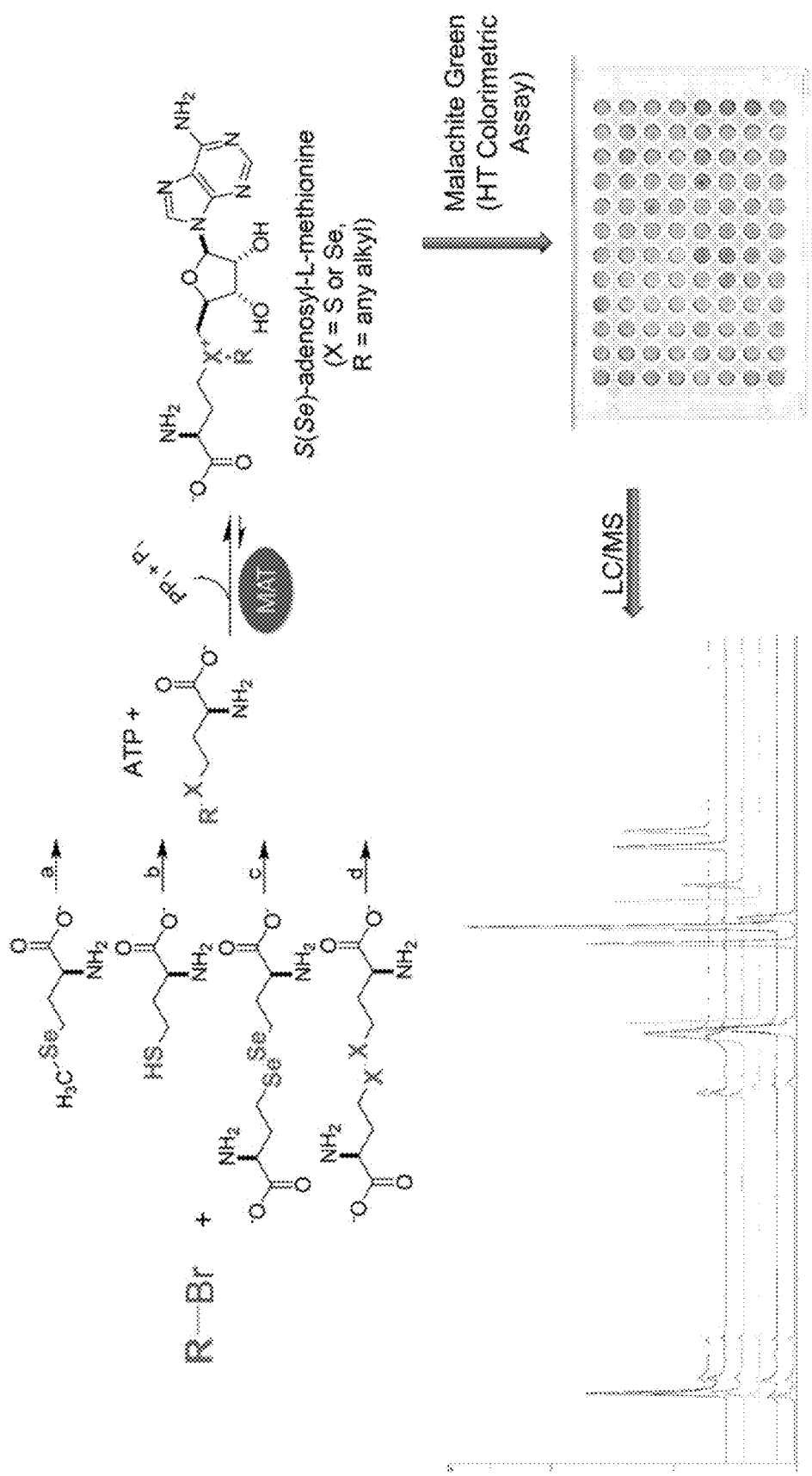

FIG. 18 shows an example of a synthesis of (seleno) methionine analogs, high-throughput MAT assay, and product verification via LC/MS.

Figure 19:
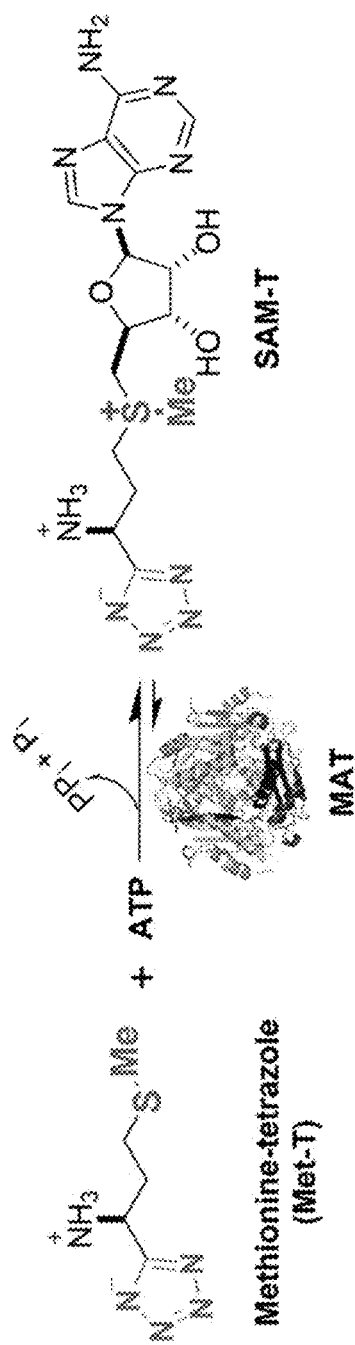

FIG. 19 illustrates a reaction catalyzed by MAT.

Figure 20:

FIG. 20 presents the synthesis of methionine tetrazole (T-met), where: (a) is (Boc)$_2$O, pyridine, NH$_4$HCO$_3$, rt, 5 h, 70-8-%; (b) is (TFA)$_2$O: pyridine (1:1), THF, 0° C., 3 h, 85-95%; (c) is NaN$_3$, ZnBr$_2$, H$_2$O/2-propanol (2:1), 80° C., 16 h, 80-90%; and (d) is Et$_2$NH, CH$_2$Cl$_2$, 0.5 h, 80-94%.

Figure 21:
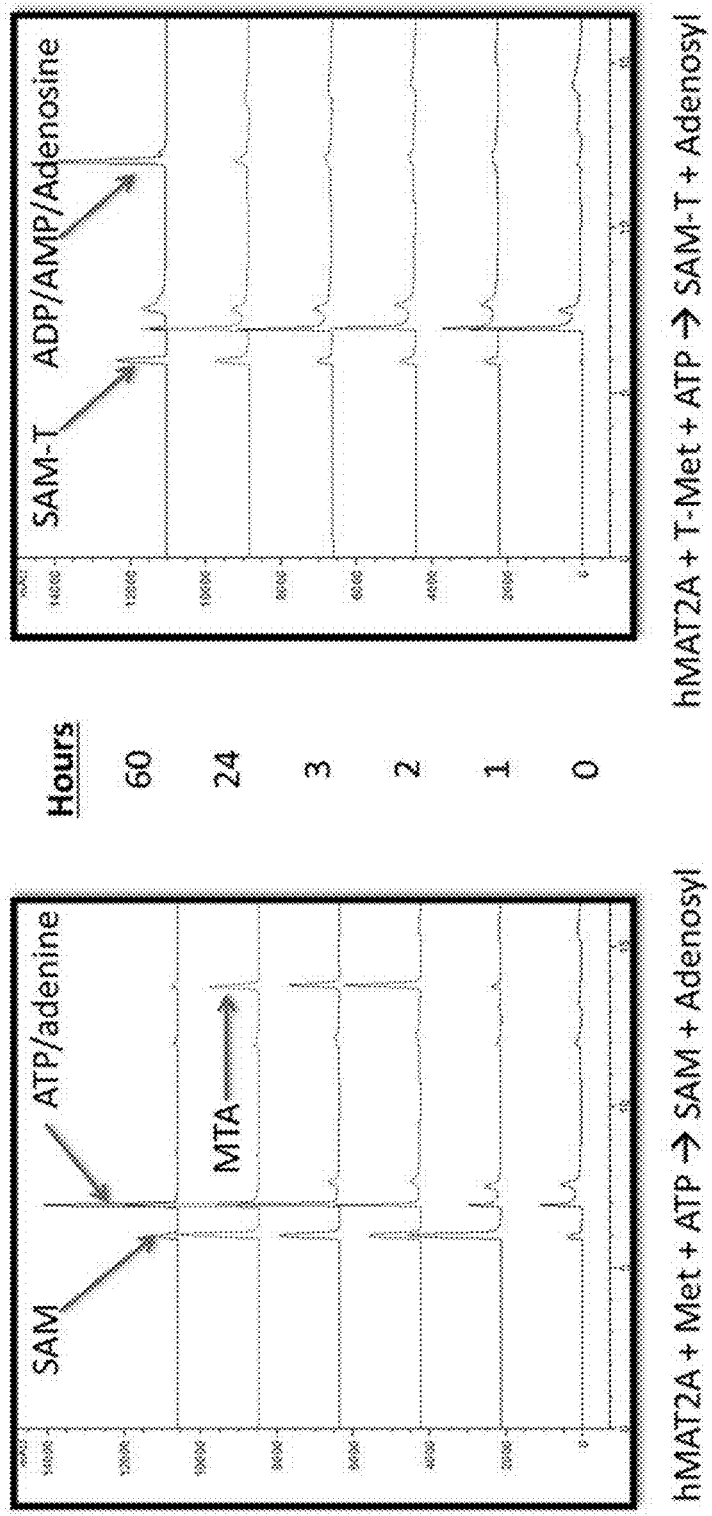

FIG. 21 provides data illustrating the stability of SAM-T relative to native SAM.

DETAILED DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All references to singular characteristics or limitations of the present disclosure shall include the corresponding plural characteristic(s) or limitation(s) and vice versa, unless otherwise specified or clearly implied to the contrary by the context in which the reference is made.

The methods and compositions of the present disclosure, including components thereof, can comprise, consist of, or consist essentially of the essential elements and limitations of the embodiments described herein, as well as any additional or optional components or limitations described herein or otherwise useful.

While the terms used herein are believed to be well understood by one of ordinary skill in the art, some definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a fluorophore" includes a plurality of such images, and so forth.

Unless otherwise indicated, all numbers expressing quantities, properties, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

With regard to alkyl substituents, the term "alkyl" refers to alkyl groups with the general formula $C_nH_{2n+1}$, where n is in the range of about 1 to about 18 or more. The groups can be straight-chained or branched. Alkyl, when used herein, also comprises "lower alkyls," which refer to alkyl groups with the general formula $C_nH_{2n+1}$, where n is in the range of about 1 to about 6. In some embodiments, n is about 1 to about 3. Examples include methyl, ethyl, propyl, isopropyl, n-butyl, sec-butyl, t-butyl, isobutyl, n-pentyl, isopentyl, neopentyl, n-hexyl, and the like. Throughout the specification "alkyl" is generally used to refer to both unsubstituted alkyl groups and substituted alkyl groups, and this practice holds true for the other groups (e.g., cycloalkyl, etc.) described herein.

The term "aryl" as used herein is a group that contains any carbon-based aromatic group including, but not limited to, benzene, naphthalene, phenyl, biphenyl, phenoxybenzene, and the like. The term "aryl" also includes biaryls (e.g., naphthalene or biphenyl) or "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, optionally substituted alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "thiol" as used herein is represented by a formula —SH.

The term "substrate" means a substance that is acted upon by an enzyme in a chemical reaction.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds, peptides, lipids, oligonucleotides, and oligosaccharides. Illustrative substituents include, for example, those described herein. The permissible substituents can be one or more and the same or different for appropriate organic compounds. For purposes of this disclosure, cobalamin may comprise alkyl substituents and/or any permissible substituents of organic compounds described herein, including those that induce strain in the embodied compounds. This disclosure is not intended to be limited in any manner by the permissible substituents of organic compounds.

Notably, throughout the present disclosure, various embodiments of the methods and compositions provided herein are described in the written examples and in the drawings. In these examples and drawings, some specific structures are labeled with numbers (e.g., 1, 2, 3, etc.) to refer to the structures. For example, FIG. 8 includes distinct structures/compounds labeled as 31, 32, 33, 32, and 35, respectively.

The presently-disclosed subject matter further includes pharmaceutical compositions comprising compounds as disclosed herein. Such pharmaceutical compositions may comprise at least one pharmaceutically-acceptable carrier. In this regard, the term "pharmaceutically acceptable carrier" refers to sterile aqueous or non-aqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions, which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents. Moreover, the compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use. The formulations can be presented in unit-dose or multi-dose containers, for example sealed ampoules and vials, and can be stored in a frozen or freeze-dried (lyophilized) condition requiring only the addition of sterile liquid carrier immediately prior to use.

The presently-disclosed subject matter further includes a kit that can include a compound or pharmaceutical composition as described herein, packaged together with a device useful for administration of the compound or composition. As will be recognized by those or ordinary skill in the art, the appropriate administration-aiding device will depend on the formulation of the compound or composition that is selected and/or the desired administration site/method. For example, if the formulation of the compound or composition is appropriate for injection in a subject, the device could be a syringe. For another example, if the desired administration site is cell culture media, the device could be a sterile pipette.

Still further, the presently-disclosed subject matter includes a method for treating disease(s), such as cancer. In some embodiments, the method comprises administering a compound, including one of the compounds described herein, to an administration site of a subject in need thereof.

The term "administering" refers to any method of providing a compound and/or pharmaceutical composition thereof to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition (e.g., cancer, tumors, etc.). In further various aspects, a preparation can be administered prophylactically; that is, administered for prevention of a disease or condition.

In some embodiments, a subject will be administered an effective amount of the compound. In this respect, the term "effective amount" refers to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Additionally, the terms "subject" or "subject in need thereof" refer to a target of administration, which optionally displays symptoms related to a particular disease, pathological condition, disorder, or the like. The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "subject" includes human and veterinary subjects.

The terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Moreover, in some embodiments, the present disclosure provides a novel chemoenzymatic alternative for the synthesis of SAM and/or SeAM analogs. Certain embodiments of the subject matter of the present disclosure are related to methionine analog synthesis to provide substrates for a range of permissive methionine adenosyltransferases (MATs). Further embodiments of the present disclosure include analogs of S-adenosyl-1-methionine. Still further embodiments of the present disclosure include analogs of Se-adenosyl-L-methionine. And various embodiments of the present disclosure are advantageous at least because they circumvent liabilities of the existing state of the art.

One embodiment of the subject matter of the present disclosure is a chemoenzymatic synthesis of SAM analogs and/or SeAM analogs. In some embodiments, the present disclosure provides methods of reacting S/Se-Met analogs with methyl transferases to produce SAM and/or SeAM analogs. In certain methods of the present disclosure, ≥about 20% turnover from S/Se-Met analog(s) to SAM/SeAM analog(s) is achieved. And in other embodiments, ≥about 10%, and/or ≥about 30%, and/or ≥about 40% and/or ≥about 50% turnover from S/Se-Met analog(s) to SAM and/or SeAM analog(s) is achieved in the presently disclosed methods.

Embodiments of the subject matter of the present disclosure also present the ability to directly couple SAM and/or SeAM synthesis with downstream MTase utilization in a one-pot reaction. As such, one embodiment of the subject matter of the present disclosure is a process using MAT to produce SAM and/or SeAM analogs.

An additional advantage of this approach is the permeability of cells to methionine, suggesting the novel potential for intracellular SAM and/or SeAM analog synthesis as enabling technology for a broad range of chemical and/or biological applications.

In some embodiments, the present disclosure is directed to the synthesis of L-methionine and/or L-selenomethionine analogs, including non-natural and/or synthetic analogs, and to uses thereof. Indeed, in certain embodiments, the disclosure provides compounds of the Formula II:

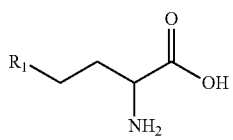
(II)

wherein $R_1$ is an alkyl group. In certain embodiments, $R_1$ comprises a propyl group, an allyl group, an aryl group and/or a propargyl group. Further, in some embodiments, $R_1$ is chosen from:

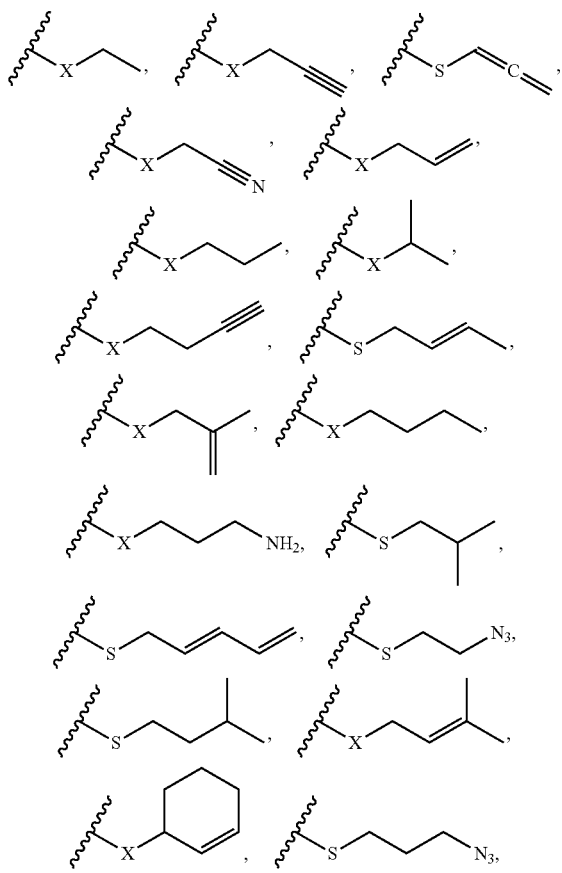

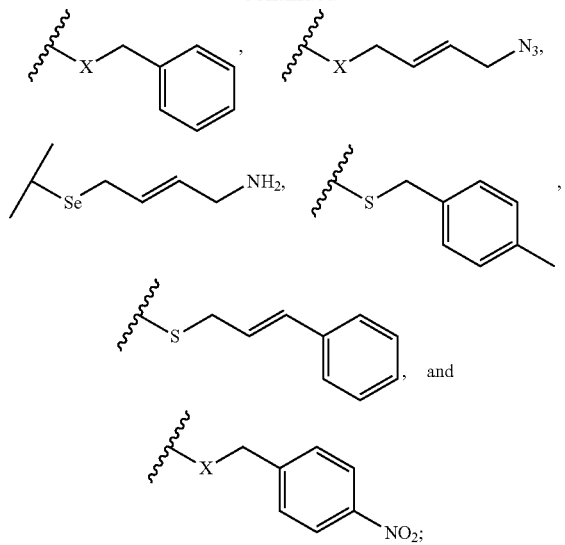

and X is selected from the group consisting of S and Se.

In some embodiments, $R_1$ is selected from the group consisting of

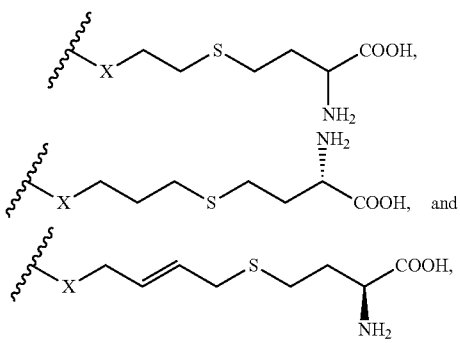

wherein X is S.

Additionally, the present disclosure is directed to the synthesis of cofactor analogs of S-adenosyl-L-methionine and/or Se-adenosyl-L-methionine using methionine adenosyltransferase, such as non-natural and/or synthetic analogs, and to uses thereof.

Accordingly, in some embodiments, the present disclosure provides an S-adenosyl-L-methionine (SAM) and/or an Se-adenosyl-L-methionine (SeAM) analog of the Formula I:

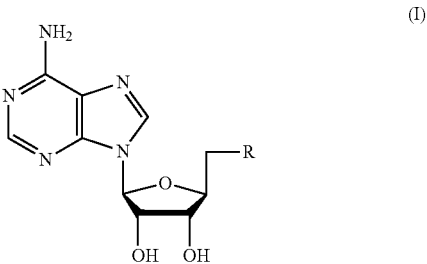
(I)

wherein R comprises a compound according to Formula II and wherein R is attached through an S or Se atom and/or through the X atom. And in certain embodiments, R comprises methionine-tetrazole.

The present disclosure also provides, in certain embodiments, methods of producing a SAM analog and/or a SeAM analog, comprising at least the step of reacting a first substrate with a second substrate in the presence of a methionine adenosyltransferase (MAT). Additionally, the present disclosure provides, in some embodiments, methods of producing an indolocarbazole analog. Such methods comprise the step of reacting a first substrate with a second substrate in the presence of a methionine adenosyltransferase (MAT).

In some embodiments, the first substrate comprises a compound according to Formula II, the second substrate comprises adenosine triphosphate (ATP) and/or the MAT comprises at least one of human MAT II catalytic alpha and regulatory beta subunit (hMAT2), human MAT II catalytic alpha subunit alone (hMAT2A), human MAT I catalytic subunit alpha (hMAT1A), *Escherichia coli* MAT (eMAT), *Sulfolobus solfataricus* MAT (sMAT), and *Methanocaldococcus jannaschii* MAT (mMAT). Additionally, the present disclosure provides that any of the methods described herein may be conducted one pot, i.e., a single vessel. The terms "vessel", "pot" and "container" are used interchangeably in the present disclosure.

The present disclosure further presents a method for production of a chemical library, the method comprising the step of reacting a plurality of compounds according to Formula II with ATP in the presence of at least one MAT to obtain at least one synthesized compound. In some embodiments, the at least one synthesized compound is a SAM analog and/or a SeAM analog. Furthermore, the present disclosure also provides, in certain embodiments, a method of producing at least one SAM analog and/or at least one SeAM analog. The method comprises the step of reacting a first substrate comprising methionine-tetrazole with a second substrate in the presence of at least one methionine adenosyltransferase (MAT). Moreover, in some embodiments, the second substrate comprises ATP and/or the MAT comprises at least one of human MAT II catalytic alpha and regulatory beta subunit (hMAT2), human MAT II catalytic alpha subunit alone (hMAT2A), human MAT I catalytic subunit alpha (hMAT1A), *Escherichia coli* MAT (eMAT), *Sulfolobus solfataricus* MAT (sMAT), and *Methanocaldococcus jannaschii* MAT (mMAT).

And in some embodiments, the present disclosure provides a method for producing a natural product analog, comprising: (i) reacting a methionine analog and at least one methionine adenosyltransferase to produce a SAM analog and/or a SeAM analog in a vessel; (ii) providing at least one methyl transferase and at least one natural product in the vessel; and (iii) alkylating the natural product in the presence of the methyl transferase and the SAM analog and/or the SeAM analog to produce a natural product analog in the vessel. In some embodiments, the methionine analog is a compound according to Formula II, as described hereinabove.

Similarly, the present disclosure provides a method for alkylating at least one drug, at least one molecule of DNA and/or at least one protein, the method comprising (i) reacting a methionine analog and at least one methionine adenosyltransferase to produce a SAM analog and/or a SeAM analog in a vessel; (ii) providing at least one methyl transferase and at least one drug, at least one molecule of DNA and/or at least one protein in the vessel; and (iii) alkylating the at least one drug, at least one molecule of DNA and/or at least one protein to produce a drug analog, a DNA analog and/or a protein analog in the vessel.

And in certain embodiments, S-adenosyl-L-homocysteine hydrolase (SAH-hdyrolase) is provided in the vessel. It is believed that inclusion of SAH-hydrolase (SAHH) in the coupled reaction may prevent product inhibition associated with most if not all methyltransferases.

In some embodiments, the present disclosure provides an S-adenosyl-L-methionine (SAM) or Se-adenosyl-L-methionine (SeAM) analog of the Formula III:

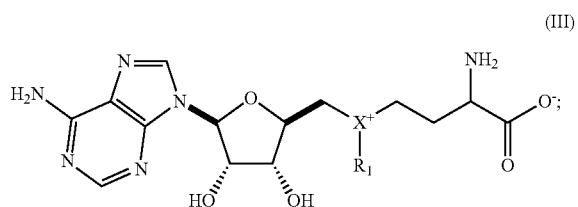

(III)

wherein X is selected from the group consisting of S and Se; wherein, when X is S, $R_1$ is selected from the group consisting of:

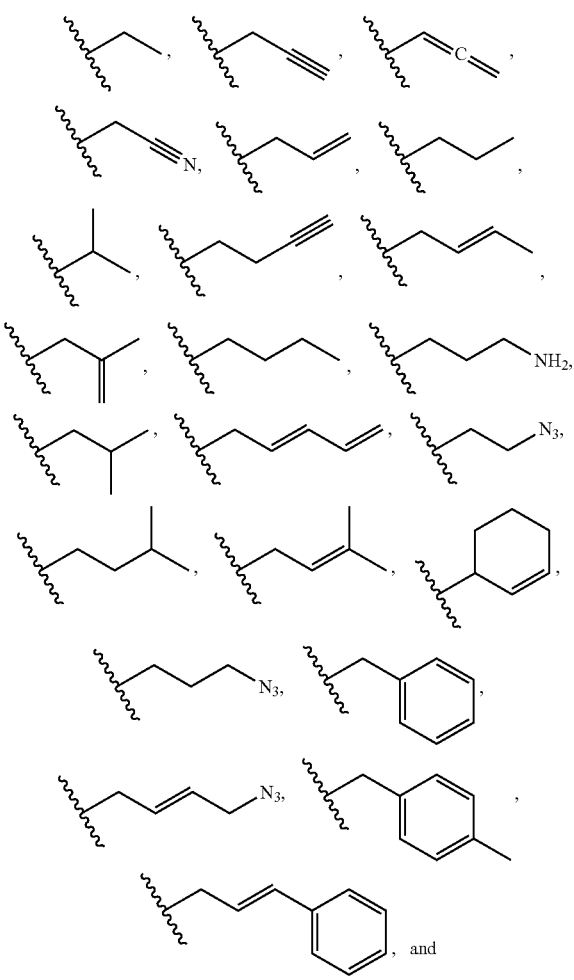

-continued

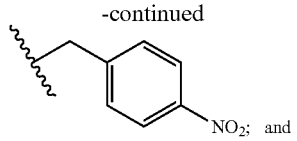

NO₂; and wherein, when X is Se, R₁ is selected from the group consisting of:

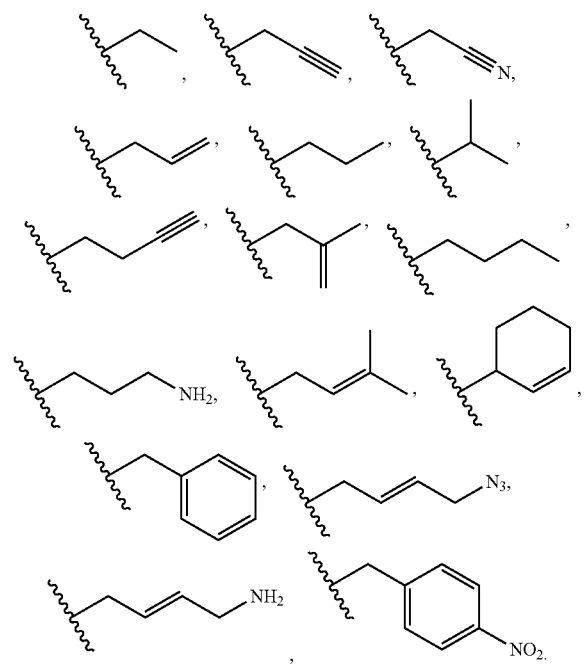

In some embodiments, the present disclosure provides an S-adenosyl-L-methionine analog of the Formula I:

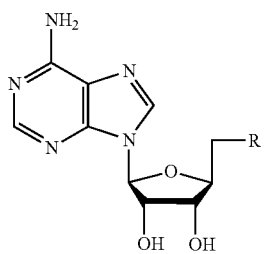

(I)

wherein R is a compound according to Formula II and R is attached through an S atom.

In some embodiments, the present disclosure provides a method of producing an S-adenosyl-L-methionine analog or an S-adenosyl-L-methionine analog of the present disclosure, comprising the step of reacting a first substrate comprising a methionine analog with a second substrate in the presence of a methionine adenosyltransferase (MAT). In some embodiments, the second substrate comprises adenosine triphosphate (ATP), and in certain embodiments, the MAT comprises at least one of human MAT II catalytic alpha and regulatory beta subunit (hMAT2), human MAT II catalytic alpha subunit alone (hMAT2A), human MAT I catalytic subunit alpha (hMAT1A), *Escherichia coli* MAT (eMAT), *Sulfolobus solfataricus* MAT (sMAT), and *Methanocaldococcus jannaschii* MAT (mMAT).

In some embodiments of the methods of the present disclosure, the first substrate is a compound of the Formula II:

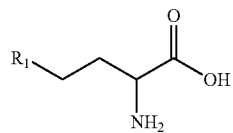

(II)

wherein R₁ is selected from the group consisting of

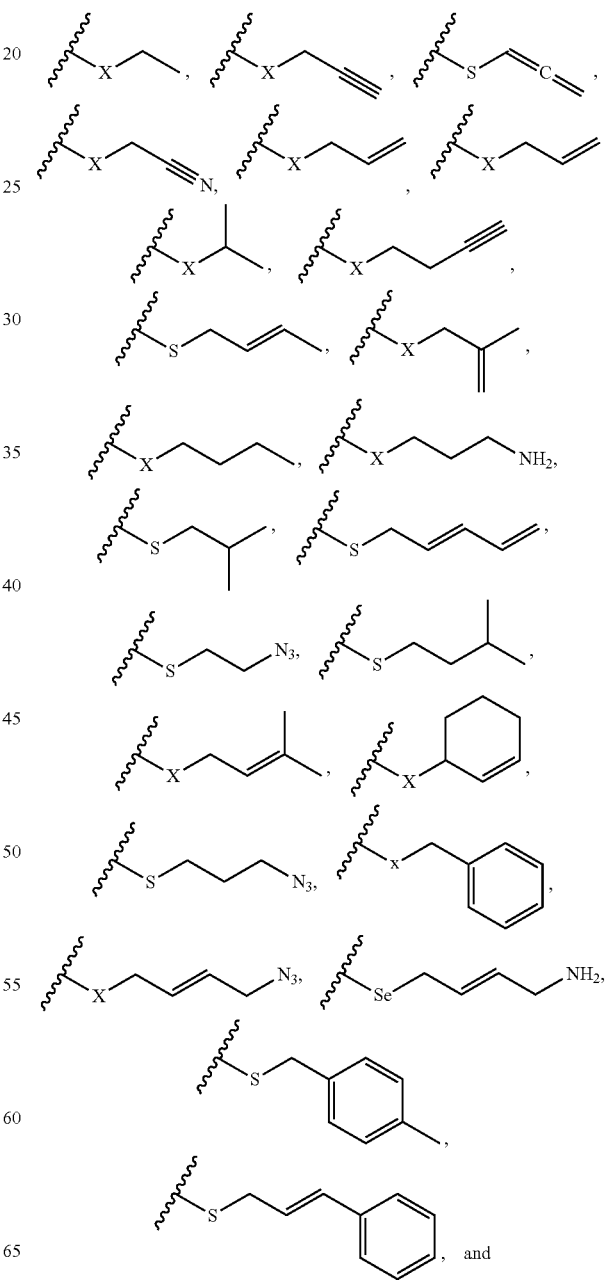

and

-continued

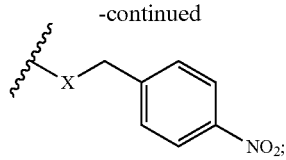

wherein X is selected from the group consisting of S and Se.

Further, in some embodiments, the present disclosure provides a method of producing an indolocarbazole analog, comprising the step of reacting a first substrate comprising a methionine analog with a second substrate in the presence of a methionine adenosyltransferase (MAT), wherein the methionine analog is a compound of the Formula II:

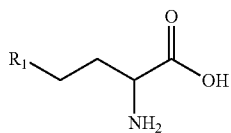
(II)

wherein $R_1$ is selected from the group consisting of

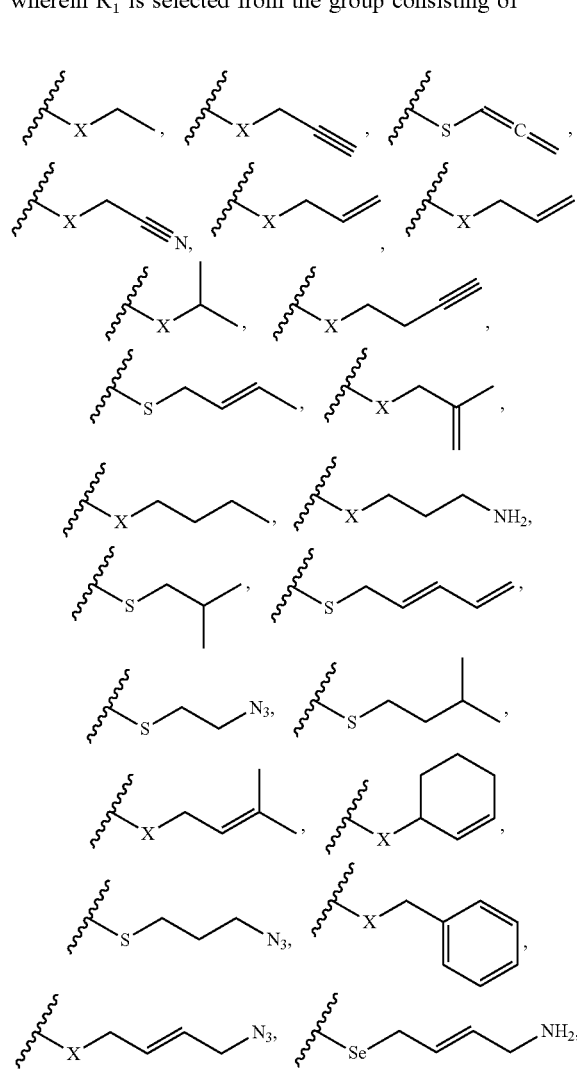

-continued

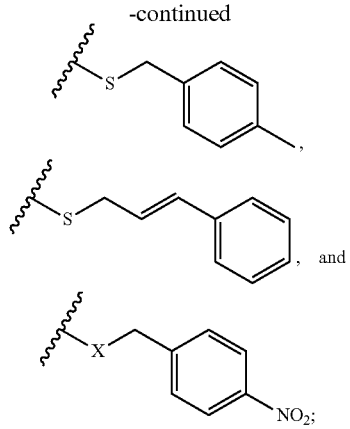
, and

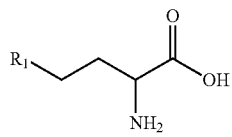

and wherein X is selected from the group consisting of S and Se. In some embodiments, the second substrate comprises at least one indolocarbazole group. And in some embodiments, the MAT comprises at least one of human MAT II catalytic alpha and regulatory beta subunit (hMAT2), human MAT II catalytic alpha subunit alone (hMAT2A), human MAT I catalytic subunit alpha (hMAT1A), *Escherichia coli* MAT (eMAT), *Sulfolobus solfataricus* MAT (sMAT), and *Methanocaldococcus jannaschii* MAT (mMAT).

Moreover, in some embodiments, the present disclosure provides a method for producing a natural product analog, comprising: (i) reacting a methionine analog and at least one methionine adenosyltransferase to produce an S-adenosyl-L-methionine analog and/or an Se-adenosyl-L-methionine analog of the present disclosure in a vessel; (ii) providing at least one methyl transferase and a natural product in the vessel; and (iii) alkylating the natural product in the presence of the methyl transferase and the S-adenosyl-L-methionine analog and/or Se-adenosyl-L-methionine analog to produce a natural product analog in the vessel. In some embodiments of this method, the methionine analog is a compound of the Formula II:

(II)

wherein $R_1$ is selected from the group consisting of

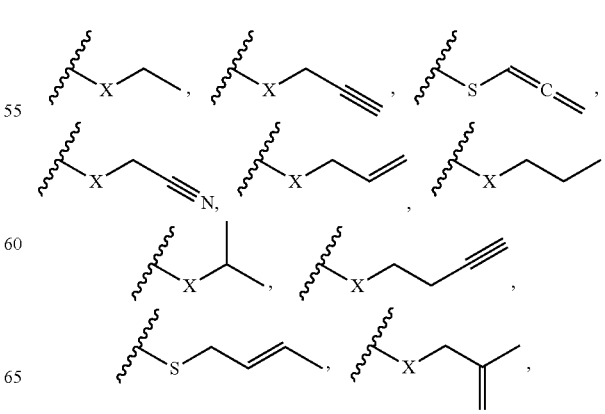

-continued

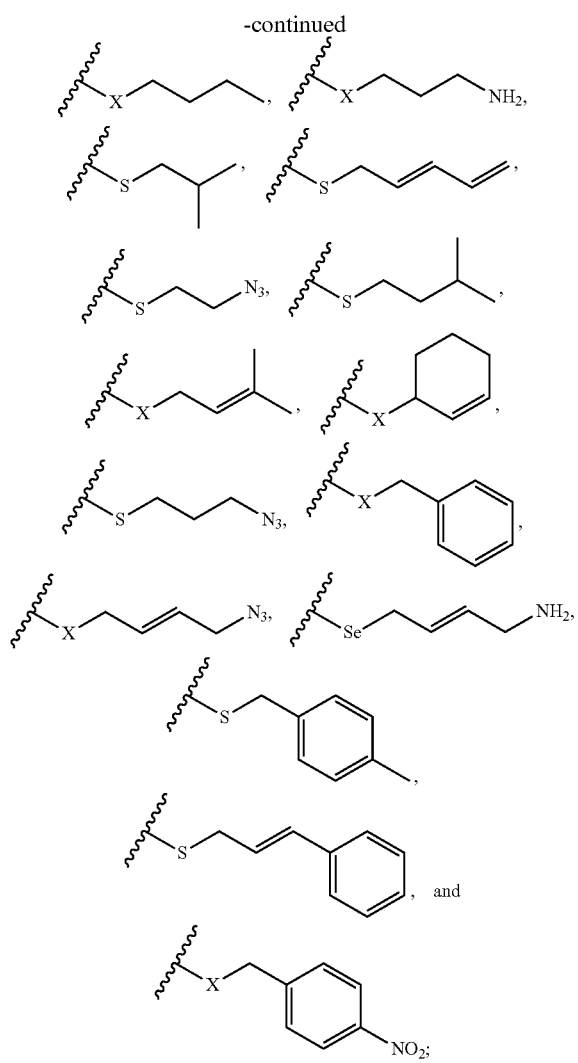

and wherein X is selected from the group consisting of S and Se.

The present disclosure profiles a range of MATs to identify MAT(s) that turn over a wide range of methionine analogs to the corresponding SAM and/or SeAM analogs. Further, the present disclosure demonstrates that a MAT reaction can be coupled in a single pot to generate differential alkylation. This enzymatic platform for differential alkylation (alkylrandomization) is an improvement over the existing prior art.

As indicated herein, in some embodiments, the subject matter of the present disclosure is directed to the synthesis of differentially alkylated analogs. Another embodiment provides a process of combining a library of differentially-alkylated analogs with a promiscuous methionine adenosyltransferase to afford the synthesis of differentially alkylated SAM and/or SeAM analogs. In certain embodiments, the present disclosure is directed to a method for producing a chemical library, comprising reacting a plurality of L-methionine and/or L-selenomethionine analogs with ATP in the presence of at least one MAT to obtain a plurality of SAM and/or SeAM analogs.

Another embodiment of the subject matter of the present disclosure is a process of the compounds of the present disclosure with promiscuous methyltransferases to afford differential alkylation of drugs and natural products. A further embodiment of the subject matter of the present disclosure provides differentially alkylated SAM and/or SeAM analogs. Yet another embodiment of the subject matter of the present disclosure provides SAM and/or SeAM analogs bearing reactive functional groups as reagents for cell biology/epigenetics.

And a further embodiment of the subject matter of the present disclosure is the process of feeding said analogs (bearing reactive functional groups) to afford the above in a cell-based format (versus crude extracts which is the current state of the art). Additionally, the subject matter of the present disclosure provides a platform for MAT engineering and evolution, a coupled MAT-MTase platform for natural product alkylrandomization, and a platform for MTase engineering and evolution.

One of ordinary skill in the art would readily recognize that embodiments of the subject matter of the present disclosure provide robust combinatorial methods for the synthesis of methionine analogs.

Moreover, the ability to couple SAM synthesis and utilization in a single vessel circumvents issues associated with rapid SAM analog decomposition.

EXAMPLES

The presently-disclosed subject matter is further illustrated by the following specific but non-limiting examples. The examples may include compilations of data that are representative of data gathered at various times during the course of development and experimentation related to the presently-disclosed subject matter.

Example I

Chemoenzymatic Synthesis of SAM Analogs:

This example highlights a broadly applicable platform for the syntheses of SAM analogs that is directly compatible with downstream SAM utilizing enzymes. The ability to couple SAM synthesis and utilization in a single vessel circumvents issues associated with rapid SAM analog decomposition and thereby opens the door to the further interrogation of a wide range of SAM utilizing enzymes. As a proof of concept for the feasibility of natural product 'alkylrandomization', the coupled strategy was used to generate a small set of indolocarbazole analogs in conjunction with the rebeccamycin O-methyltransferase RebM.

Figure 2:
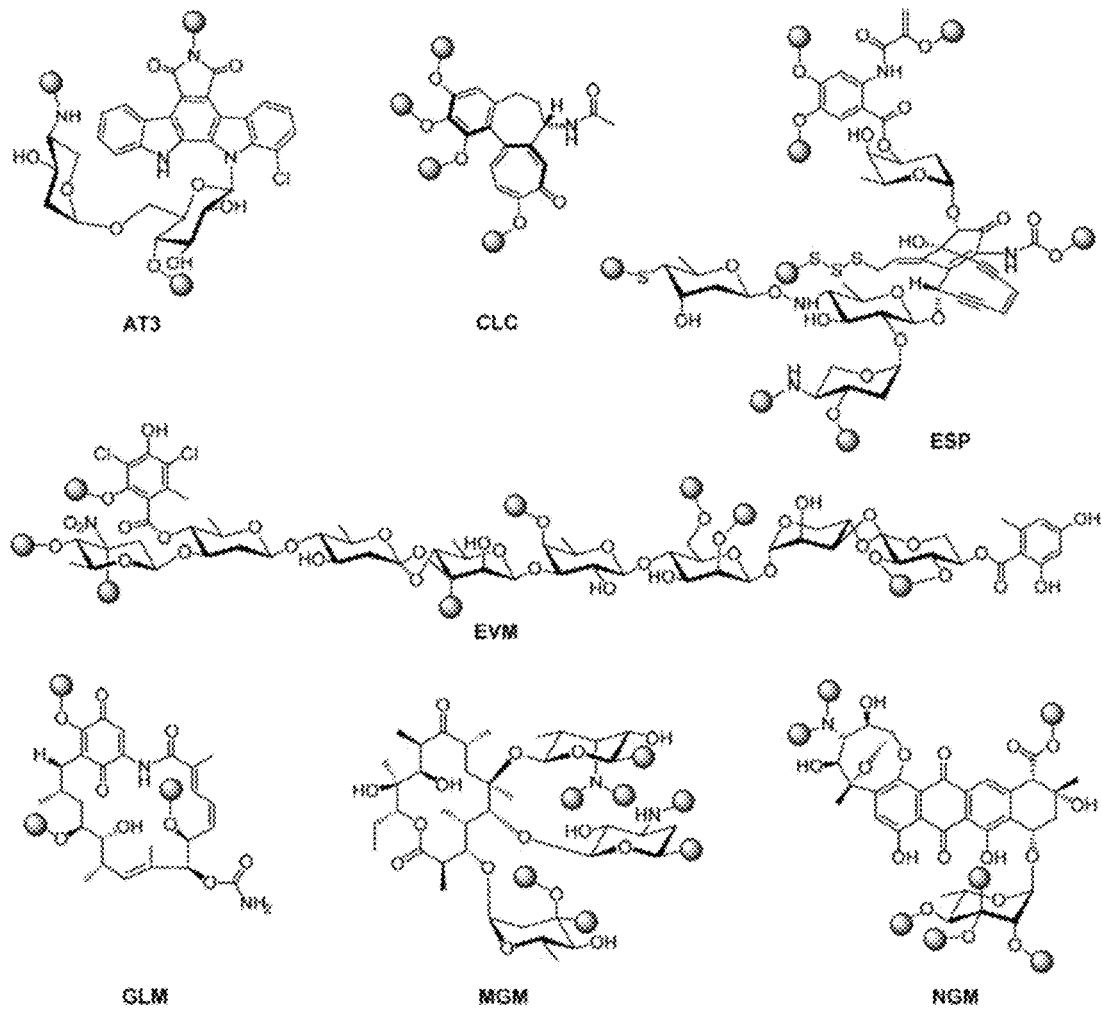
FIG. 2 shows representative methylated natural products where methyl groups deriving from SAM via MT-catalyzed methylation are highlighted as spheres. AT3 (AT2433); CLC (colchicine); ESP (esperamicin); EVM (evernimicin); GLM (geldamycin); MGM (megalomicin); and NGM (nogalamycin) are presented.
Figure 3:
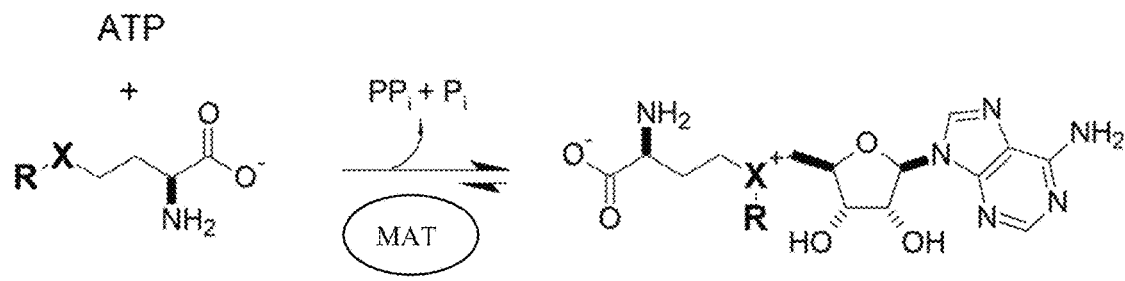
FIG. 3 provides a methionine adenosyltransferase (MAT)-catalyzed reaction, where L-Met (R═CH3, X═S) is the native substrate leading to native product S-adenosylmethionine (R═CH3, X═S). The variability of both R and X is described within the present disclosure.

Enzyme-catalyzed late stage group transfer-based tailoring reactions contribute to the structural and functional diversity of many complex natural products (NPs).[1] Representative examples include amination, acylation, alkylation, glycosylation, halogenation, phosphorylation and sulfation and, in some cases, enzymes responsible for such transformations display notable flexibility with respect to their substrate scope. [2] Such promiscuity is an enabling feature of chemoenzymatic NP diversification platforms as exemplified by NP glycorandomization (a platform for differential glycosylation of natural products/drugs).[3] Among the examples above, enzyme-catalyzed alkylation is a highly prevalent occurrence that leads to NP N-, O-, S- and/or C-alkylation (FIG. 2).[4] Thus, a platform to co-opt natural product methyltransferases (MTs) for broad natural product differential alkylation (alkylrandomization) will dramatically expand the potential scope of NP chemical diversity.

The typical alkyl donor for MT-catalyzed alkylation is S-adenosyl-L-methionine (SAM) and importantly, the present inventors have demonstrated NP [5], protein, [6] and nucleic acid [7] MTs to transfer alternative alkyl groups in the presence of suitably modified SAM analogs. However, reminiscent of the restriction imposed upon glycorandomization by sugar nucleotide availability, access to stable SAM analog arrays similarly restricts NP alkylrandomization development.

Current state-of-art for SAM analog chemical synthesis relies upon multi-step syntheses of diastereomeric SAM analog mixtures and requires HPLC purification to remove starting material, S-adenosyl-homocysteine (SAH, a strong inhibitor of MTs). [8] The desired purified SAM analogs from this process are also markedly unstable, thereby limiting their practical development as standalone synthetic reagents and/or biological probes. Within this context, a general platform to enable the generation and direct utilization of SAM analogs, beginning from stable precursors, would be considered advantageous.

Figure 1:
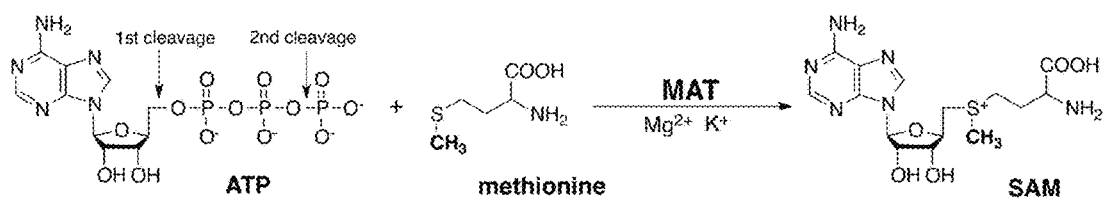
FIG. 1 illustrates a reaction catalyzed by MAT.

To address this need, herein a broad substrate specificity assessment of a representative set of five distinct methionine adenosyltransferases (MATs) from various sources is described. MAT (EC 2.5.1.6; also sometimes referred to as AdoMet synthetase or SAM synthetase) is the primary catalyst used for the biosynthesis of SAM from adenine triphosphate (ATP) and L-methionine (Met) (FIG. 1, FIG. 2) and there is preliminary evidence to suggest certain MATs to be capable of Met analog utilization. [6e, 9] Consistent with this notion, the studies highlighted herein reveal human MAT II (hMAT2) to enable the cumulative synthesis of a broad panel of unnatural SAM analogs (29 analogs detected) starting from synthetic S/Se-alkylated Met analogs (44 analogs) or commercial sources (3 analogs).

To demonstrate the feasibility of NP alkylrandomization, this study also highlights the subsequent generation of a small set of indolocarbazole analogs using a coupled hMAT2-RebM system, where RebM is the sugar C4'-O-MT involved in rebeccamycin biosynthesis. [5a, 10] This study offers both a strategic advance in terms of NP diversification and reveals hMAT2 to display surprising permissivity.

Figure 4:
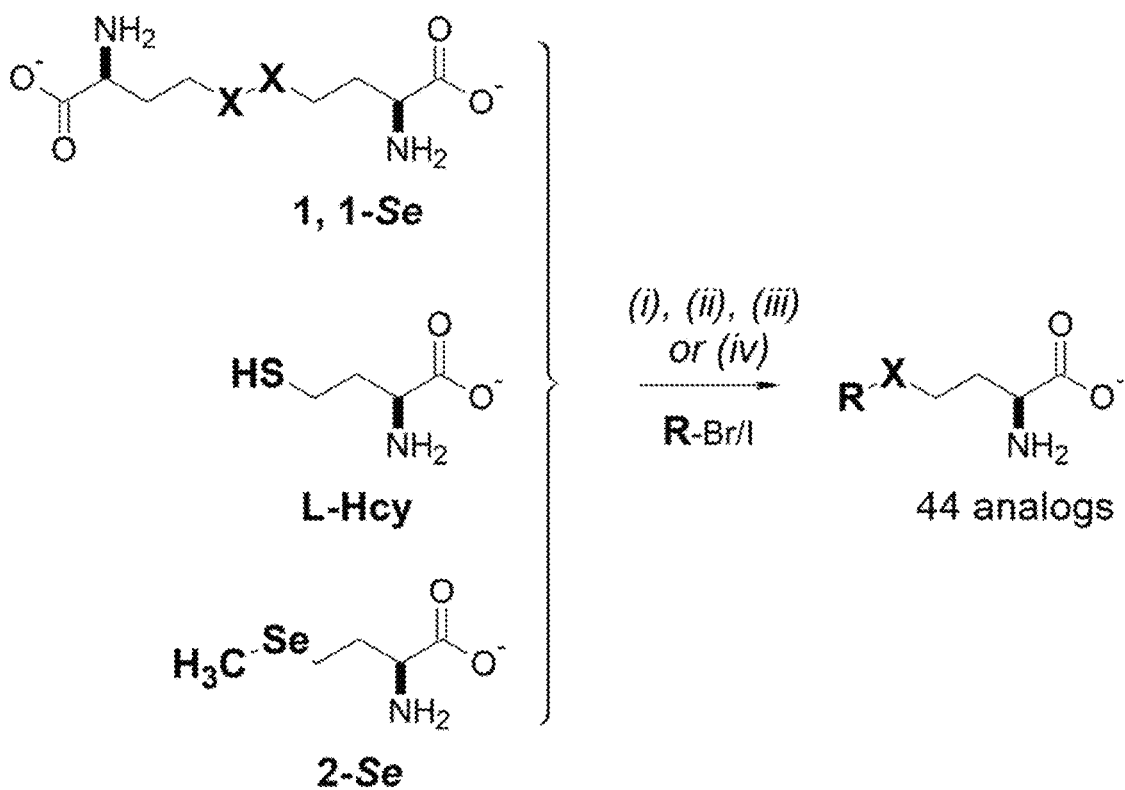
FIG. 4 presents the general methodology for the synthesis of S- and Se-L-Met analogs (X═S and Se, respectively) (i)

Given the conflicting reports regarding the relative stability of S- versus Se-SAM [6c, 6d, 11] and the fact that Se-SAM is considered a better alkyl donor than S-SAM in MT-catalyzed reactions due to the inherently longer and weaker Se—C bond, [11b] both S- and Se-Met analogs were synthesized for this study. The general strategy for the synthesis of the S- and Se-Met analog panel employed direct or reductive alkylation of the corresponding L-homocysteine dimer (1 or 1-Se, FIG. 4 i and iii, respectively), L-Hcy (FIG. 4, ii) or 2-Se (FIG. 4, iv) following modifications of reported strategies. [12] The desired S- and Se-Met analogs were purified from crude reaction mixtures by reverse phase high pressure liquid chromatography (RP-HPLC), $C_{18}$ RP flash chromatography or Dowex 50W8X-200 resin to afford isolated yields ranging from 20-90% (see Table 1).

TABLE 1

Summary of synthesized L-methionine and L-selenomethionine analogs

| Code | Compound | Method S-alkyl | Se-alkyl | Code | Compound | Method S-alkyl | Se-alkyl |
|---|---|---|---|---|---|---|---|
| 1, 1-Se | X-X-COOH/NH2 | c.a.[a] | ref [25] | 16 | S-CH=CH-CH=CH2 | FIG. 10 | n.a.[b] |
| 2, 2-Se | NH2/HOOC-X | c.a.[a] | c.a.[a] | 17 | S-CH2CH2-N3 | FIG. 10 | n.a.[b] |
| 3, 3-Se | X-Et | FIG. 10 | FIG. 12 | 18 | S-CH2CH2-iPr | FIG. 10 | n.a.[b] |
| 4, 4-Se | X-propargyl | FIG. 10 | FIG. 12 | 19, 19-Se | X-prenyl | FIG. 10 | FIG. 13 |
| 5 | S-allenyl | FIG. 10 | n.a.[b] | 20, 20-Se | X-cyclohexenyl | FIG. 11 | FIG. 13 |
| 6, 6-Se | X-CH2CN | FIG. 11 | FIG. 13 | 21 | S-CH2CH2CH2-N3 | FIG. 10 | n.a.[b] |
| 7, 7-Se | X-allyl | FIG. 11 | FIG. 12 | 22, 22-Se | X-benzyl | FIG. 10 | FIG. 14 |

TABLE 1-continued

Summary of synthesized L-methionine and L-selenomethionine analogs

| Code | Compound | Method S-alkyl | Se-alkyl | Code | Compound | Method S-alkyl | Se-alkyl |
|---|---|---|---|---|---|---|---|
| 8, 8-Se | [X-CH2CH2CH3] | FIG. 10 | FIG. 13 | 23, 23-Se | [X-CH2-CH=CH-CH2-N3] | FIG. 10 | FIG. 12 |
| 9, 9-Se | [X-CH(CH3)2] | FIG. 10 | FIG. 14 | 24-Se | [X-CH2-CH=CH-CH2-NH2] | n.a.[b] | FIG. 13 |
| 10, 10-Se | [X-CH2CH2-C≡CH] | FIG. 10 | FIG. 13 | 25 | [S-CH2-C6H4-CH3] | FIG. 10 | n.a.[b] |
| 11 | [S-CH2-CH=CH-CH3] | FIG. 10 | n.a.[b] | 26 | [S-CH2-CH=CH-C6H5] | FIG. 10 | n.a.[b] |
| 12, 12-Se | [X-CH2-C(=CH2)-CH3] | FIG. 10 | FIG. 12 | 27, 27-Se | [X-CH2-C6H4-NO2] | FIG. 11 | FIG. 13 |
| 13, 13-Se | [X-CH2CH2CH2CH3] | FIG. 10 | FIG. 13 | 28 | [S-CH2CH2-S-CH2CH2-CH(NH2)-COOH] | FIG. 10 | n.a.[b] |
| 14 | [S-CH2-CH(CH3)2] | FIG. 10 | n.a.[b] | 29 | [S-CH2CH2CH2-S-CH2CH2-CH(NH2)-COOH] | FIG. 10 | n.a.[b] |
| 15, 15-Se | [X-CH2CH2CH2-NH2] | FIG. 10 | FIG. 13 | 30 | [S-CH2-CH=CH-CH2-S-CH2CH2-CH(NH2)-COOH] | FIG. 10 | n.a.[b] |

[a]c.a.: commercially available;
[b]n.a.: not available.

A representative set of MATs from variant sources, including bacterial, archaeal and mammalian orthologs, were selected for the initial assessment. Specifically, the exploratory set included human MAT II catalytic alpha and regulatory beta subunit (hMAT2),[13] human MAT II catalytic alpha subunit alone (hMAT2A),[13] human MAT I catalytic subunit alpha (hMAT1A),[13] *Escherichia coli* MAT (eMAT),[14] and the thermophilic *Methanocaldococcus jannaschii* MAT (mMAT).[15] The basis for inclusion of the human homologs derives from an interest to interrogate the substrate specificities of disease-relevant hMATs,[16] while the additional bacterial and archaeal homologs were selected to compare and contrast the current study with prior work relating to their substrate specificities.[9a, 17]

Standard uniform assay conditions (2 mM Met analog, 1 mM ATP, 5 μM MAT, 25 mM Tris, 5 mM MgCl$_2$, 50 mM KCl, pH 8, 4 h) were adopted to facilitate this broad assessment. For the thermophilic counterpart (mMAT), reactions were conducted at 65° C., while all other reactions were incubated at 37° C. Production of SAM analogs was determined by an RP-HPLC end point assay to afford complete analysis of the desired SAM analog and/or any corresponding degradation products known to directly derive from the desired SAM analog intermediate. Putative SAM analog and SAM-derived degradative product formation was subsequently confirmed via high-resolution mass spectrometry (HRMS) analysis for all positive reactions (see Table 2).

TABLE 2

Summary of MAT reactions

| Analog | Percentage Turn-over | | | | | H. R. Mass (m/z) | |
| --- | --- | --- | --- | --- | --- | --- | --- |
| | eMAT | hMAT1A | hMAT2A | hMAT2 | mMAT | Theoretical | Observed |
| 2 | 90 | 95 | 100 | 100 | 100 | 399.1445, 297.0896[a]  | 399.1444, 298.0965[b] |
| 2-Se | 100 | 100 | 100 | 100 | 100 | 447.0890, 345.0340[a] | 447.0895, 346.0416[b] |
| 3 | 8 | 75 | 90 | 88 | 94 | 413.1602, 311.1052[a] | 413.1599, 312.1121[b] |
| 3-Se | 5 | 57 | 53 | 82 | 73 | 461.1046, 359.0497[a] | 416.1040, 360.0565[b] |
| 4 | 2 | 2 | 6 | 20 | 6 | 321.0896[a] | 322.1051[b] |
| 4-Se | 0 | 7 | 44 | 58 | 14 | 369.0340[a] | 370.0411[b] |
| 6 | 2 | 2 | 13 | 20 | 6 | 322.0848[a] | 323.0919[b] |
| 6-Se | 2 | 4 | 23 | 33 | 0 | 370.0293[a] | 371.0371[b] |
| 7 | 2 | 5 | 50 | 52 | 16 | 425.1602, 323.1052[a] | 425.1609, 324.1129[b] |
| 7-Se | 2 | 10 | 42 | 59 | 15 | 371.0497[a] | 372.0568[b] |
| 8 | 2 | 5 | 54 | 55 | 21 | 427.1758, 325.1209[a] | 427.1759, 326.1281[b] |
| 8-Se | 0 | 6 | 24 | 74 | 27 | 475.1203, 373.0653[a] | 475.1200, 374.0726[b] |
| 9 | 0 | 2 | 2 | 2 | 8 | 427.1758, 325.1209[a] | 427.1762, 326.1282[b] |
| 9-Se | 5 | 5 | 11 | 10 | 10 | 373.0653[a] | 374.0743[b] |
| 10 | 0 | 0 | 12 | 40 | 16 | 437.1602, 335.1052[a] | 437.1599, 336.1124[b] |
| 10-Se | 2 | 6 | 22 | 55 | 17 | 383.0497[a] | 384.0566[b] |
| 11 | 2 | 2 | 5 | 25 | 30 | 439.1758, 337.1209[a] | 439.1754, 338.1275[b] |
| 12 | 0 | 0 | 2 | 2 | 6 | 439.1758, 337.1209[a] | 439.1754, 338.1282[b] |
| 12-Se | 3 | 5 | 11 | 12 | 14 | 385.0653[a] | 386.0730[b] |
| 13 | 0 | 0 | 12 | 13 | 12 | 441.1915, 339.1365[a] | 441.1966, 340.1477[b] |
| 13-Se | 0 | 6 | 26 | 49 | 32 | 489.1359, 387.0810[a] | 489.1358, 388.0882[b] |
| 14 | 0 | 0 | 0 | 0 | 1 | 441.1915, 339.1365[a] | 441.1918, 340.1439[b] |
| 16 | 4 | 2 | 4 | 44 | 8 | 451.1758 | 451.1756 |
| 17 | 0 | 4 | 18 | 49 | 29 | 454.1616, 352.1066[a] | 454.1615, 353.1140[b] |
| 18 | 0 | 0 | 0 | 0 | 1 | 455.2071, 353.1522[a] | 455.2123, 354.1634[b] |
| 19 | 3 | 0 | 4 | 6 | 13 | 453.1915 | 453.2044 |
| 19-Se | 5 | 3 | 9 | 15 | 16 | 399.0810[a] | 400.0878[b] |
| 21 | 0 | 0 | 19 | 46 | 31 | 468.1772, 366.1223[a] | 468.1772, 367.1296[b] |
| 23 | 0 | 2 | 5 | 12 | 32 | 480.1772, 378.1223[a] | 480.1768, 379.1292[b] |
| 23-Se | 5 | 4 | 9 | 15 | 18 | 426.0667[a] | 427.0687[b] |
| 24-Se | 8 | 7 | 16 | 25 | 30 | 400.0762[a] | 401.0830[b] |

[a]theoretical mass of degraded 5'-alkyl-thio(seleno)-5'-deoxyadenosine (MTA); observed mass of degraded 5'-alkyl-thio(seleno)-5'-deoxyadenosine (MTA):
[b][M + H]

A cumulative comparison of the substrate specificity for all five MAT model systems based upon RP-HPLC is illustrated in FIG. 5 and FIG. 6 wherein observed 5'-methyl-thio(seleno)-5'-deoxyadenosine (MTA) production (via RP-HPLC) was interpreted as product based upon the well-established SAM decay pathways indicating MTA to directly derive from SAM (not ATP). [6d, 11a, 18] This cumulative analysis revealed hMAT2 to be the most permissive of the MATs tested at 37° C., while the thermophilic mMAT also displayed notable permissivity at 65° C. Of the 47 putative substrates tested with hMAT2, 10 led to appreciable (>50%) SAM analog production, an additional 8 led to moderate (25-50%) conversion, while 11 offered detectable product (<25%) under the conditions described. In general, smaller alkyl substitutions were better tolerated, suggesting steric infringement to possibly prohibit larger substitutions. Interestingly, in the case where direct comparisons could be made, the degree of unsaturation correlated with a reduction in turnover (e.g., propyl>allyl>propargyl). Also, in most cases, Se-analogs were preferred over their S-comparators, most notably for hMAT2. Consistent with previous studies, [19] the regulatory beta subunit of MAT2A improved the overall proficiency of hMAT2 and, in some cases, this increase in proficiency translated to a slight increase in permissivity in the current study. Finally, the addition of inorganic pyrophosphatase in an attempt to drive the reaction via degradation of the pyrophosphate co-product did not appreciably increase turnover.

Based on these results, the corresponding MATs can be generally classified as having broad (hMAT2/hMAT2A), medium (mMAT) or stringent (eMAT and hMAT1A) substrate specificities. Superimposition of available X-ray structures (hMAT1A, hMAT2A and eMAT) reveal a root mean square deviation (rmsd) of 0.268 Å between hMAT2A and hMAT1A (sequence identity of ~85%) and ~0.56 Å between eMAT and hMAT1A or hMAT2A (sequence identity of ~58%). Structural comparison of the permissive (hMAT2A) and stringent (hMAT1A and eMAT) MATs highlights key distinctions among residues (FIG. 7). Interestingly, while hMAT2A active site mutagenesis has led to a slight improvement in turnover with an unnatural analog, [6e] the current structural comparison suggests the broad substrate specificity of hMAT2A to be predominately mediated by residues within the secondary shell and/or on the solvent-exposed surface distal to active-site loops that likely contribute to interdomain movement/dynamics. Whether or not these residues contribute to the hMAT2 alpha/beta interface is currently unknown.

To subsequently assess the feasibility of 'alkylrandomization' via a single vessel coupled MAT/MT reaction, the rebeccamycin MT RebM was selected as the representative methyl transferase (MT). RebM is the sugar C4'-O-MT involved in rebeccamycin biosynthesis and has previously been demonstrated to tolerate both alternative acceptors and alkyl donors. [5a, 10] The coupled system also employed standard assay conditions (2 mM Met analog, 1 mM ATP, 50 µM rebeccamycin congener compound 31, 5 µM hMAT2, 10 µM RebM, 5 µM SAH-hydrolase, 25 mM Tris, 5 mM $MgCl_2$, 50 mM KCl, pH 8, 24 h at 37° C.) and included only S/Se-Met analogs that afforded ≥20% turnover with hMAT2 under standard conditions (FIG. 5, FIG. 6). From this pilot study, 8 out of 18 of the selected S/Se-Met series led to the production of the corresponding differentially alkylated indolocarbazoles in appreciable yields (≥40%, FIG. 8 and FIG. 15). Importantly, inclusion of SAH-hydrolase (SAHH) in the coupled reaction, to prevent product inhibition associated with most if not all MTs, [20] improved overall product yields by 15-40%. Notably, this is the first report of MT-catalyzed acetonitrilylation (See FIG. 8, compound 35 deriving from L-Met analog 6 or 6-Se).

In conclusion, the broad substrate specificity analysis presented revealed hMAT2/2A and mMAT to display notably broad substrate tolerance. Of these, hMAT2A is overexpressed in a number of tumor types, [21] where inhibition of hMAT2A by small molecule inhibitors or siRNA affords dramatic tumor reduction. [22] The discovered substrate malleability of hMAT2A in conjunction with aberrant cancer-specific hMAT2A overexpression therefore may offer the potential to employ suitable S/Se-Met analogs as cell-based metabolic probes of the role of methylation in cancer. In addition, the work highlighted herein enables one of the first the facile syntheses of SAM analogs directly compatible with downstream SAM utilizing enzymes including MTs and is advantageous over other recently reported chemoenzymatic strategies that depend upon synthetic non-native alkylated amino acid alkyl donors and nucleoside acceptors. As such, this platform circumvents a major liability of prior SAM analog/MT strategies, namely SAM analog decomposition, and thereby opens the door to the further interrogation of a host of MTs which operate upon macromolecular (protein/nucleic acid) and small molecule (natural products) substrates. Finally, the strategy presented unveils a single vessel proof of concept for natural product 'alkyl-randomization' which, while currently somewhat limited via enzyme specificity, is expected to be further advanced via MT/MAT directed evolution and/or structure-based engineering in a manner reminiscent to that used for advancing glycorandomization. [3, 23]

Materials and Methods

Unless otherwise stated, all general chemicals and reagents were purchased from Sigma-Aldrich (St. Louis, Mo., USA) or Acros (New Jersey, USA) and were reagent grade or better. L-homocystine was purchased from Bachem (Torrance, Calif., USA). L-homocystine [24] and L-selenohomocysteine [25] were synthesized following previously published protocols. *E. coli* BL21(DE3) competent cells were purchased from Invitrogen (Carlsbad, Calif.). The pET28a *E. coli* expression vector was purchased from Novagen (Madison, Wis.). Primers were purchased from Integrated DNA Technology (Coralville, Iowa). Pfu DNA polymerase was purchased from Stratagene (La Jolla, Calif.). Restriction enzymes and T4 DNA ligase were purchased from New England Biolabs (Ipswich, Mass.). PD-10 column and Ni-NTA superflow columns were purchased from GE Healthcare (Piscataway, N.J.).

High-resolution mass spectrometric data were obtained using a Waters (Milford, Mass.) LCT time-of-flight spectrometer for electrospray ionization (ESI) or AB SCIEX TripleTOF® 5600 System. NMR spectra were obtained on Varian Unity Inova 400 or 500 MHz instruments (Palo Alto, Calif.) at the NMR facility of College of Pharmacy at University of Kentucky using 99.8% $CDCl_3$ with 0.05% v/v TMS, 99.8% $CD_3OD$ or 99.8% $D_2O$ from Cambridge Isotopes (Cambridge Isotope Laboratories, MA, USA). $^1H$ and $^{13}C$ chemical shifts were referenced to internal solvent resonances. Multiplicities are indicated by s (singlet), d (doublet), t (triplet), q (quartet), quin (quintet), m (multiplet), and br (broad). Chemical shifts are reported in parts per million (ppm) and coupling constants J are given in Hz. Routine $^{13}C$ NMR spectra were fully decoupled by broadband WALTZ decoupling. All NMR spectra were recorded at ambient temperature.

Normal-phase flash chromatography was performed on 40-63 µm, 60 Å silica gel (from Silicycle, Quebec, Canada). Analytical TLC was performed on silica gel glass TLC plates (from EMD chemical Inc). Visualization was accomplished with UV light (254 nm) followed by staining with dilute sulfuric acid (5% in ethanol) solution or 10% ninhydrin in ethanol and heating. High performance liquid chromatography (HPLC) was accomplished using an Agilent 1260 system equipped with a diode array detector (DAD).

Method A (HPLC):

Analytical reverse-phase (RP) HPLC was conducted with a Luna C-18 (5 µm, 4.6 mm×250 mm) column (Phenomenex, Torrance, Calif., USA) [gradient of 1% B to 40% B over 22 min, 55% B to 100% B over 3 min, 100% B for 6 min, 100% B to 5% B over 1 min, 5% B for 3 min (A=ddH$_2$O with 0.1% TFA; B=acetonitrile) flow rate=1 mL min$^{-1}$; $A_{218}$]. The reaction was monitored by the retention time difference between starting material and product.

Method B (HPLC):

Semi-preparative RP HPLC was conducted on a Gemini $C_{18}$ (5 µm, 10×250 mm; Phenomenex, Torrance, Calif., USA) column to purify the methionine analogs [gradient of 5% B to 55% B over 25 min, 55% B to 100% B over 2 min, 100% B for 6 min, 100% B to 5% B over 1 min, 5% B for 4 min (A=ddH$_2$O with 0.1% TFA; B=acetonitrile) flow rate=4.5 mL min$^d$; $A_{218}$].

Method C (Flash Chromatography):

Pilot reversed-phase purification was conducted by flash column chromatography using an Alltech $C_{18}$ Extract-Clean column (10,000 mg, 75 mL, Alltech Associates, Deerfield, Ill., USA) for the scale-up purification of methionine analogs. The column was pre-equilibrated with ddH$_2$O/0.1% TFA and after loading the solid crude material, a gradient of 100/0 to 60/40 water:acetonitrile containing 0.1% TFA was used as the mobile phase. Eluted fractions were checked by TLC (15:1:84 MeOH/NH$_4$OH/CHCl$_3$, ninhydrin stain) and confirmed via analytical HPLC (Method A) to identify product fractions.

Method D (HPLC):

To monitor MAT reactions, analytical RP HPLC employed a Luna $C_{18}$ column (5 µm, 4.6 mm×250 mm; Phenomenex, Torrance, Calif., USA) [gradient of 10% B to 40% B over 15 min, 40% B to 75% B over 5 min (A=10 mM NaH$_2$PO$_4$, 5 mM octane sulfonic acid, pH was adjusted to 3.5 using phosphoric acid; B=acetonitrile) flow rate=1 mL min$^{-1}$; $A_{254}$].

Method E (HPLC):

To monitor the coupled hMAT2/RebM reactions, analytical RP HPLC was conducted with a Luna $C_{18}$ column (5 µm, 4.6 mm×250 mm; Phenomenex, Torrance, Calif., USA) [gradient of 10% B to 100% B over 20 min (A=ddH$_2$O with 0.1% TFA; B=acetonitrile) flow rate=1 mL min$^{-1}$; $A_{315}$].

The sequence of MATs involved in this study can be found within the National Center for Biotechnology Information (NCBI) Protein database and include: *Homo sapiens* MAT2A (hMAT2A; genebank accession number AAH01686.1); *Homo sapiens* MAT1A (hMAT1A, genebank accession number AAQ89058.1); *Homo sapiens* MAT II (co-expression of MAT2A with MAT2B; genebank accession number AAH01686.1); *Escherichia coli* MAT (eMAT; genebank accession number AAG58073.1); and *Methanocaldococcus jannaschii* (mMAT; genebank accession number Q58605.1).

All DNA sequencing was conducted by the University of Wisconsin Biotechnology Center with the primers T7 promoter. All Luria-Bertani (LB) media and agar were supplemented with 35 μg mL$^{-1}$ kanamycin. High-throughput assay absorbance readings were conducted using a FLUOstar Omega plate reader (BMG Labtechnologies, Cary, N.C., USA). HPLC peak areas were integrated with Star Chromatography Workstation Software (Varian, Palo Alto, Calif., USA) and the percent conversion calculated as a percent of the total peak area. High resolution electrospray ionization (ESI) mass spectra were recorded on a AB Sciex Triple TOF 5600 instrument coupled with an Eksigent Ekspert micro LC 200 system with source temperature of 150° C., ion spray voltage floating (ISVF) of 5000 V in positive mode. Samples were infused at 20 μL min-1 and spectra collected for 3 min at a resolution greater than 31000. In negative mode ISVF of −4000 V was used. C17 lysophosphatidyl choline with a mass of 510.3554 and C17 lysophosphatidic acid with a mass of 423.2517 were used as internal references to calibrate the spectra in positive and negative modes respectively.

General Procedure of for Azido Installation (FIG. 9, used for compounds 17, 21, 23, 23-Se, 28, 29 and 30). Dibromo-alkane (1.0 g, 1.0 eq) was dissolved in 20 mL $CH_2Cl_2$ and to this was added $nBu_4NHSO_4$ (0.5 eq) and $NaN_3$ (0.8 eq) under stirring. A 20 mL sat. $NaHCO_3$ solution was subsequently added and the reaction was stirred vigorously for 2 h. The organic layer was washed with water and brine (20 mL each) and then dried over $Na_2SO_4$. After the $CH_2Cl_2$ solvent was concentrated in vacuo carefully, the product was used directly as a monobromo or dibromo mixture without further purification for the alkylation reaction.

General Procedure for the Na/$NH_3$ Reduction & S-Alkylation of L-Homocystine (FIG. 10, used for compounds 3, 4, 5, 8-19, 21-23, 25, 26 and 28-30). L,L-homocystine (100 mg, 0.37 mmol) (from Bachem, Torrance, Calif., USA) was added to 20 mL liquid ammonia at −78° C. and stirred until fully dissolved. Small fragments of sodium metal (34 mg, 1.5 mmol) were added until a deep blue color persisted for at least 1 min. The corresponding alkyl bromide (2.0 eq) was then introduced, which caused the blue solution to quickly proceed to a mixture with a white precipitate. Ammonium chloride (20 mg, 0.37 mmol) was then added to the reaction and the reaction was immediately removed from the cooling bath. The reaction flask was left open to the atmosphere at ambient temperature to allow ammonia to evaporate. The resulting residue was dissolved in 5 mL deionized water and the pH was adjusted to pH 5-7 by the addition of 1 M HCl. The solvent was removed under reduced pressure and the residue was dried. A fraction (10 mg) of the dried residue was dissolved with 400 μL $dH_2O$ with 0.1% TFA, adjusted to pH 3 by the addition of 1 M HCl, centrifuged and subsequently purified by semi-preparative HPLC (Method B) to ultimately afford the desired S-alkylated L-methionine analogs in 22%-99% yield.

General Procedure for the S-Alkylation of L-Homocysteine (FIG. 11, used for compounds 6, 7, 20 and 27). L-homocysteine[S1] (10 mg, 0.07 mmol) was dissolved in 1 mL acetone and to this was added the corresponding alkyl bromide (2.0 eq) and $K_2CO_3$ (20 mg, 0.14 mmol). The reaction was stirred under room temperature until HPLC indicated the completion of the reaction (Method A). The solvent was removed in vacuo, the resulting residue was dissolved in 400 μL $dH_2O$ with 0.1% TFA, adjusted to pH 3 by the addition of 1 M HCl, centrifuged and subsequently purified by semi-preparative HPLC (Method B) to ultimately afford the desired S-alkylated L-methionine analogs in 20%-60% yield.

General Procedure for the Na/$NH_3$ Reduction & Alkylation of L-Selenohomocystine (FIG. 11, used for compounds 3-Se, 4-Se, 7-Se, 12-Se and 23-Se). L-Selenohomocystine[S2] (100 mg, 0.27 mmol) was treated in manner identical to that described in the section labeled "general procedure for the Na/$NH_3$ reduction & S-alkylation of L-homocysteine" to provide the desired Se-alkylated L-selenomethionine analogs in yields ranging from 16%-85% yield.

General procedure for $NaBH_4$ reduction & Se-alkylation of L-selenohomocystine (FIG. 13, used for compounds 6-Se, 8-Se, 10-Se, 13-Se, 15-Se, 19-Se, 20-Se, 24-Se, 27-Se). According to a procedure from Zhang et al., [26] to the THF solution of L-selenohomocystine[S2] (100 mg, 0.276 mmol) in a small flask was added alkyl bromide (4.0 eq) under $N_2$ with stirring at room temperature. $NaBH_4$ (83.5 mg, 2.21 mmol, 8 eq) was dissolved in 0.12 M NaOH/water, and this solution was introduced to the reaction flask drop-wise via syringe. The reaction was subsequently stirred under $N_2$ at room temperature for 5 h and then adjusted to pH 5-7 by addition of 1 M HCl. The solvent was removed completely under reduced pressure and the residue was dried. A portion (10 mg) of the dried residue was dissolved with 400 μL $H_2O$ with 0.1% TFA, adjusted to pH 3 by addition of 1 M HCl, centrifuged and the supernatant was purified by preparative HPLC (Method B) to provide the desired Se-alkylated L-selenomethionine analogs in yields ranging from 18%-99% yield.

General Procedure for the Demethylation & Se-Alkylation of L-Selenomethionine (FIG. 14, used for compounds 9-Se, 22-Se). According to a procedure from Dekker, et al, [27] L-selenomethionine (100 mg, 0.51 mmol) was dissolved in 5 mL of concentrated HCl and to this was added the corresponding alkyl bromide (5.0 eq). The reaction was refluxed at 100° C. for 12 h. The reaction was then allowed to cool down to room temperature, diluted with water (10 mL), and adjusted with 30% $NH_4OH$ to pH=7. The solvent was concentrated under reduced pressure to less than 1 mL, frozen at −80° C., and lyophilized to form a dry powder. The powder was purified by reversed-phase flash chromatography (Method C), to give 9-Se (9% yield) and 22-Se (7% yield).

Example (2S)-2-amino-4-(ethylsulfanyl)butanoic acid (compound 3)

Some modifications of the strategy illustrated in FIG. 10 were employed for the synthesis of compound 3. Specifically, the dried residue after completion of the L-homocystine (250 mg, 0.932 mmol)/iodoethane (165 μL, 2.04 mmol) and subsequent evaporation of $NH_3$ was dissolved in $ddH_2O$ (30 mL) and solid NaOH (1.20 g, 0.03 mol) was added, creating a 1 M sodium hydroxide solution. After stirring for 1 h, the basic solution was slowly loaded onto a Dowex 50W8X-200 2.5 cm×3 cm column prequilibrated with $ddH_2O$. The column was washed with several column volumes of $ddH_2O$ and the product subsequently eluted with 2.5% aqueous $NH_4OH$. The fractions, identified by TLC (15:1:84 MeOH/$NH_4OH$/$CHCl_3$, ninhydrin stain), were combined and lyophilized to a white amorphous solid (184 mg, 61% yield). ¹H NMR (DMSO-d₆/TFA-d₁=20/1, 500 MHz) δ 4.01 (t, J=6.2 Hz, 1H), 2.48-2.64 (m, 2H), 2.49 (q, J=7.3 Hz, 2H), 2.00 (m, 2H), 1.17 (t, J=7.3 Hz, 3H); ¹³C NMR (DMSO-d₆/TFA-d₁=20/1, 125 MHz) δ 175.9, 56.3, 35.4, 31.4, 30.0, 20.1; HRESI calculated for $C_6H_{14}NO_2S$ ([M+H]⁺) m/z 164.0740; measured m/z 164.0744.

Example (2S)-2-amino-4-(ethylselanyl)butanoic acid (compound 3-Se)

FIG. 12 with bromoethane yielded compound 3-Se (4.1 mg, 85% yield) as a white solid. ¹H NMR (D₂O, 400 MHz) δ 3.85 (t, J=6.2 Hz, 1H), 2.43-2.50 (m, 4H), 2.01-2.11 (m, 2H), 1.19 (t, J=7.6 Hz, 3H); ¹³C NMR (D₂O, 100 MHz) δ 172.6, 53.5, 30.8, 17.0, 16.8, 14.7; HRESI calculated for $C_6H_{14}NO_2Se$ ([M+H]⁺) m/z 212.0184; measured m/z 212.0187.

Example (2S)-2-amino-4-(prop-2-yn-1-ylsulfanyl)butanoic acid (compound 4)

FIG. 10 with propargyl bromide yielded compound 4 (4.5 mg, 75% yield) as a white solid together with compound 5 (0.3 mg) as a white oil. ¹H NMR (D₂O/TFA=20/1, 400 MHz) δ 4.09 (t, J=6.4 Hz, 1H), 3.24 (d, J=2.8 Hz, 2H), 2.74 (t, J=6.8 Hz, 2H), 2.53 (t, J=2.4 Hz, 1H), 2.07-2.26 (m, 2H); ¹³C NMR (D₂O/TFA=20/1, 100 MHz) δ 171.3, 80.0, 72.0, 51.4, 28.8, 26.0, 17.8; HRESI calculated for $C_7H_{12}NO_2S$ ([M+H]⁺) m/z 174.0583; measured m/z 174.0582.

Example (2S)-2-amino-4-(prop-2-yn-1-ylselanyl)butanoic acid (compound 4-Se)

FIG. 12 with propargyl bromide yielded compound 4-Se (0.8 mg, 16% yield) as a white solid. ¹H NMR (D₂O, 400 MHz) δ 3.97 (t, J=6.3 Hz, 1H), 3.15 (t, J=1.6 Hz, 2H), 2.74 (t, J=7.6 Hz, 2H), 2.49 (t, J=2.6 Hz, 1H), 2.08-2.27 (m, 2H); ¹³C NMR (D₂O, 100 MHz) δ 172.0, 81.3, 72.0, 53.0, 30.3, 18.4, 6.3; HRESI calculated for $C_7H_{12}NO_2Se$ ([M+H]⁺) m/z 222.0028; measured m/z 222.0035.

Example (2S)-2-amino-4-(propa-1,2-dien-1-ylsulfanyl)butanoic acid (compound 5)

FIG. 10 with propargyl bromide yielded compound 5 (0.3 mg, 6% yield) as a white oil together with compound 4 (4.5 mg, 75% yield) as a white solid. 5.69 (t, J=6.4 Hz, 1H), 4.94 (d, J=10.4 Hz, 2H), 4.06 (t, J=6.4 Hz, 1H), 2.70 (t, J=7.6 Hz, 2H), 2.07-2.19 (m, 2H); HRESI calculated for $C_7H_{12}NO_2S$ ([M+H]⁺) m/z 174.0583; measured m/z 174.0582.

Example (2S)-2-amino-4-[(cyanomethyl)sulfanyl]butanoic acid (compound 6)

FIG. 11 with L-homocysteine (10 mg, 74 μmol) and bromoacetonitrile yielded compound 6 (7.6 mg, 59% yield) as a white solid. ¹H NMR (D₂O, 500 MHz) δ 4.10 (t, J=6.5H, 1H), 3.46 (s, 2H), 2.80 (t, J=11.5 Hz, 2H), 1.98-2.27 (m, 2H); ¹³C NMR (D₂O, 125 MHz) δ 171.4, 118.5, 51.4, 29.0, 27.3, 16.1; HRESI calculated for $C_6H_{11}N_2O_2S$ ([M+H]⁺) m/z 175.0536; measured m/z 175.0534.

Example (2S)-2-amino-4-[(cyanomethyl)selanyl]butanoic acid (compound 6-Se)

FIG. 13 with bromoacetonitrile yielded compound 6-Se (1.2 mg, 20% yield) as a white solid. ¹H NMR (D₂O, 400 MHz) δ 3.91 (t, J=6.5 Hz, 1H), 3.29 (s, 2H), 2.81 (dd, J=15.6, 6.8 Hz, 1H), 2.77 (dd, J=13.2, 6.8 Hz, 1H), 2.11-2.29 (m, 2H); ¹³C NMR (D₂O, 100 MHz) δ 172.3, 119.6, 53.2, 30.4, 19.9, 1.9; HRESI calculated for $C_6H_{11}N_2O_2Se$ ([M+H]⁺) 222.9980; measured m/z 222.9973.

Example (2S)-2-amino-4-(prop-2-en-1-ylsulfanyl)butanoic acid (compound 7)

FIG. 11 with allyl bromide yielded compound 7 (5.3 mg, 41% yield) as a white solid. ¹H NMR (D₂O/TFA=20/1, 400 MHz) δ 5.61-5.72 (m, 1H), 5.04 (d, J=10.8 Hz, 1H), 4.98 (d, J=2.0 Hz, 1H), 3.85 (t, J=6.8 Hz, 1H), 3.05 (dd, J=7.2, 0.8 Hz, 2H), 2.48 (t, J=7.6 Hz, 2H), 1.92-2.10 (m, 2H); ¹³C NMR (DMSO-d₆/TFA-d₁=8/1, 125 MHz) δ 171.2, 134.9, 117.9, 51.5, 34.0, 30.4, 25.9; HRESI calculated for $C_7H_{14}NO_2S$ ([M+H]⁺) m/z 176.0740; measured m/z 176.0728.

Example (2S)-2-amino-4-(prop-2-en-1-ylselanyl)butanoic acid (compound 7-Se)

FIG. 12 with allyl bromide yielded compound 7-Se (3.0 mg, 59% yield) as a white solid. ¹H NMR (D₂O, 400 MHz) δ 5.70-5.77 (m, 1H), 4.9 (m, 2H), 3.90 (t, J=6.3 Hz, 1H), 3.08 (d, J=7.8 Hz, 2H), 2.45 (t, J=8.2 Hz, 2H), 2.03-2.10 (m, 2H); ¹³C NMR (D₂O, 100 MHz) δ 172.1, 134.6, 116.6, 53.2, 30.5, 25.2, 16.7; HRESI calculated for $C_7H_{14}NO_2Se$ ([M+H]⁺) m/z 224.0184; measured m/z 224.0179.

Example (2S)-2-amino-4-(propylsulfanyl)butanoic acid (compound 8)

A protocol identical to that described for compound 3 using L-homocystine (150 mg, 0.559 mmol) and 1-bromopropane (112 μL, 1.23 mmol) gave compound 8 (181 mg, 91% yield) as a white amorphous solid. ¹H NMR (DMSO-d₆/TFA-d₁=20/1, 400 MHz) δ 4.05 (t, J=6.8 Hz, 1H), 2.61 (m, 2H), 2.50 (t, J=7.3 Hz, 2H), 2.03-2.09 (m, 2H), 1.56 (quin, J=7.3 Hz, 2H), 0.96 (t, J=7.2 Hz, 3H); ¹³C NMR (DMSO-d₆/TFA-d₁=20/1, 125 MHz) δ 171.2, 51.5, 33.3, 30.6, 26.9, 22.9, 13.6; HRESI calculated for $C_7H_{16}NO_2S$ ([M+H]⁺) m/z 178.0896; measured m/z 178.0900.

Example (2S)-2-amino-4-(propylselanyl)butanoic acid (compound 8-Se)

FIG. 13 with 1-bromopropane yielded compound 8-Se (3.1 mg, 50% yield) as a white solid. ¹H NMR (D₂O, 400

MHz) δ 3.97 (t, J=6.8 Hz, 1H), 2.34 (t, J=7.6 Hz, 2H), 2.27 (t, J=7.0 Hz, 2H), 1.95-2.13 (m, 2H), 1.30 (dt, J=7.2, 7.0 Hz, 2H), 0.59 (t, J=7.2 Hz, 3H); $^{13}$C NMR (D$_2$O, 100 MHz) δ 171.3, 52.6, 30.4, 25.9, 22.9, 17.1, 13.5; HRESI calculated for C$_7$H$_{16}$NO$_2$Se ([M+H]$^+$) m/z 226.0341; measured m/z 226.0353.

Example (2S)-2-amino-4-(propan-2-ylsulfanyl)butanoic acid (compound 9)

FIG. 10 with 2-bromopropane yielded compound 9 (1.2 mg, 22% yield) as a white solid. $^1$H NMR (D$_2$O, 400 MHz) δ 4.01 (t, J=6.5 Hz, 1H), 2.89 (quin, J=6.8 Hz, 1H), 2.59 (t, J=7.4 Hz, 2H), 1.96-2.12 (m, 2H), 1.09 (d, J=6.7 Hz, 6H); $^{13}$C NMR (D$_2$O, 100 MHz) δ 171.8, 52.0, 34.2, 29.8, 24.8, 22.2 (2 carbons); HRESI calculated for C$_7$H$_{16}$NO$_2$S ([M+H]$^+$) m/z 178.0896; measured m/z 178.0887.

Example (2S)-2-amino-4-(propan-2-ylselanyl)butanoic acid (compound 9-Se)

FIG. 14 with 2-bromopropane (0.24 mL, 2.54 mmol) yielded compound 9-Se (10 mg, 9% yield) as a white solid. L-selenomethionine (94.9 mg) was recovered after flash reversed-phase chromatography via Method C. $^1$H NMR (D$_2$O, 400 MHz) δ 3.83 (t, J=6.3 Hz, 1H), 3.09 (quin, J=6.85 Hz, 1H), 2.55 (t, J=7.8 Hz, 2H), 2.04-2.17 (m, 2H), 1.24 (d, J=7.0 Hz, 6H); $^{13}$C NMR (D$_2$O, 100 MHz) δ 110.0, 53.9, 31.3, 29.4, 23.5, 23.4, 16.7; HRESI calculated for C$_7$H$_{16}$NO$_2$Se ([M+H]$^+$) m/z 226.0341; measured m/z 226.0333.

Example (2S)-2-amino-4-(but-3-yn-1-ylsulfanyl)butanoic acid (compound 10)

FIG. 10 with 4-bromo-1-butyne yielded compound 10 (1.9 mg, 33% yield) as a white oil. $^1$H NMR (D$_2$O, 400 MHz) δ 3.88 (t, J=6.4 Hz, 1H), 2.62 (t, J=5.2 Hz, 2H), 2.58 (t, J=7.2 Hz, 2H), 2.40 (td, J=6.8 Hz, 2.4 Hz, 1H), 2.27 (t, J=2.54 Hz, 1H), 1.98-2.14 (m, 2H); $^{13}$C NMR (D$_2$O, 100 MHz) δ 172.8, 83.6, 70.3, 52.7, 29.8, 29.5, 26.4, 18.6; HRESI calculated for C$_8$H$_{14}$NO$_2$S ([M+H]$^+$) m/z 188.0740; measured m/z 188.0759.

Example (2S)-2-amino-4-(but-3-yn-1-ylselanyl)butanoic acid (compound 10-Se)

FIG. 13 with 4-bromo-1-butyne yielded compound 10-Se (2.1 mg, 33% yield) as a light yellow solid. $^1$H NMR (D$_2$O, 400 MHz) δ 3.92 (t, J=6.3 Hz, 1H), 2.61 (t, J=6.8 Hz, 2H), 2.57 (t, J=8.0 Hz, 2H), 2.44 (td, J=7.2 Hz, 2.8 Hz, 2H), 2.20 (t, J=2.4 Hz, 1H), 2.02-2.20 (m, 2H); $^{13}$C NMR (D$_2$O, 100 MHz) δ 172.1, 84.3, 70.1, 53.1, 30.7, 21.4, 19.5, 17.7; HRESI calculated for C$_8$H$_{14}$NO$_2$Se ([M+H]$^+$) m/z 236.0184; measured m/z 236.0200.

Example (2S)-2-amino-4-[(2E)-but-2-en-1-ylsulfanyl]butanoic acid (compound 11)

A protocol identical to that described for compound 3 using L-homocystine (150 mg, 0.559 mmol) and (2E)-1-bromo-2-butene (125 μL, 1.23 mmol) gave compound 11 (169 mg, 80% yield) as a white amorphous solid. $^1$H NMR (D$_2$O, 400 MHz) δ 5.40 (m, 1H), 5.24 (m, 1H), 3.97 (t, J=6.0 Hz, 1H), 2.92 (d, J=7.2 Hz, 2H), 2.42 (t, J=7.6 Hz, 2H), 1.91-2.03 (m, 2H), 1.44 (d, J=5.6 Hz, 3H); $^{13}$C NMR (D$_2$O, 100 MHz) δ 171.4, 129.8, 125.9, 51.7, 32.4, 29.11, 24.6, 16.7. HRESI calculated for C$_8$H$_{16}$NO$_2$S ([M+H]$^+$) m/z 190.0896; measured m/z 190.0904.

Example (2S)-2-amino-4-[(2-methylprop-2-en-1-yl)sulfanyl] butanoic acid (compound 12)

A protocol identical to that described for compound 3 using L-Homocystine (150 mg, 0.559 mmol) and 3-bromo-2-methylpropene (223 μL, 2.20 mmol) gave Compound 12 (169 mg, 80% yield) was obtained as a white amorphous solid. $^1$H NMR (DMSO-d$_6$/TFA-d$_1$=20/1, 400 MHz) δ 4.88 (dd, J=4.6, 3.2 Hz, 2H), 4.04 (t, J=6.4 Hz, 1H), 3.15 (s, 2H), 2.53 (m, 2H), 2.05-2.09 (m, 2H), 1.78 (s, 3H); $^{13}$C NMR (DMSO-d$_6$/TFA-d$_1$=20/1, 125 MHz) δ 171.1, 141.4, 136.5, 51.5, 38.4, 30.1, 26.1, 20.8; HRESI calculated for C$_8$H$_{16}$NO$_2$S ([M+H]$^+$) m/z 190.0896; measured m/z 190.0904.

Example (2S)-2-amino-4-[(2-methylprop-2-en-1-yl)selanyl] butanoic acid (compound 12-Se)

FIG. 12 with 3-bromo-2-methylpropene yielded compound 12-Se (5.0 mg, 85% yield) as a white solid. $^1$H NMR (D$_2$O, 400 MHz) δ 4.6 (m, 2H), 3.99 (t, J=6.5 Hz, 1H), 3.11 (s, 2H), 2.43-2.50 (m, 2H), 1.98-2.11 (m, 2H), 1.54 (s, 3H); $^{13}$C NMR (D$_2$O, 100 MHz) δ 171.4, 142.4, 113.0, 52.7, 30.5, 30.3, 20.0, 17.2; HRESI calculated for C$_8$H$_{15}$NO$_2$SeNa ([M+Na]$^+$) m/z 260.0160; measured m/z 260.0157.

Example (2S)-2-amino-4-(butylsulfanyl)butanoic acid (compound 13)

FIG. 10 with 1-bromobutane yielded compound 13 (6.4 mg, 99% yield) as a white solid. $^1$H NMR (D$_2$O, 400 MHz) δ 4.00 (t, J=6.3 Hz, 1H), 2.56 (t, J=7.4 Hz, 2H), 2.45 (t, J=7.2 Hz, 2H), 1.96-2.11 (m, 2H), 1.41 (quin, J=7.4 Hz, 2H), 1.23 (dt, J=7.4, 6.8 Hz, 2H), 0.73 (t, J=7.2 Hz, 3H); $^{13}$C NMR (D$_2$O, 100 MHz) δ 172.0, 52.1, 30.6, 30.4, 29.5, 26.2, 21.2, 12.7; HRESI calculated for C$_8$H$_{18}$NO$_2$S ([M+H]$^+$) m/z 192.1053; measured m/z 192.1074.

Example (2S)-2-amino-4-(butylselanyl)butanoic acid (compound 13-Se)

FIG. 13 with 1-bromobutane yielded compound 13-Se (9.3 mg, 100% yield) as a white solid. $^1$H NMR (D$_2$O, 400

MHz) δ 4.01 (t, J=6.5 Hz, 1H), 2.53 (m, 4H), 2.05-2.15 (m, 2H), 1.49 (quin, J=7.4 Hz, 2H), 1.23 (dt, J=7.6, 7.4 Hz, 2H), 0.74 (t, J=7.4 Hz, 3H); $^{13}$C NMR (D$_2$O, 100 MHz) δ 171.8, 52.8, 31.6, 30.6, 23.4, 22.2, 17.1, 12.6; HRESI calculated for C$_8$H$_{18}$NO$_2$Se ([M+H]$^+$) m/z 240.0497; measured m/z 240.0510.

Example (2S)-2-amino-4-[(2-methylpropyl)sulfanyl]butanoic acid (compound 14)

FIG. 10 with 2-bromo-propane yielded compound 14 (6.4 mg, 99% yield) as a white solid. $^1$H NMR (D$_2$O/TFA=20/1, 400 MHz) δ 4.04 (t, J=6.3 Hz, 1H), 2.54 (t, J=7.4 Hz, 2H), 2.32 (d, J=7.0 Hz, 2H), 2.00-2.12 (m, 2H), 1.6 (m, 1H), 0.78 (d, J=6.7 Hz, 6H); $^{13}$C NMR (D$_2$O/TFA=20/1, 100 MHz) δ 171.5, 51.6, 39.9, 29.4, 27.7, 26.8, 21.0 (2 carbons); HRESI calculated for C$_8$H$_{18}$NO$_2$S ([M+H]$^+$) m/z 192.1053; measured m/z 192.1043.

Example (2S)-2-amino-4-[(3-aminopropyl)sulfanyl]butanoic acid (compound 15)

FIG. 10 with 3-bromopropylamine hydrobromide yielded compound 15 (1.4 mg, 24% yield) as a white solid. $^1$H NMR (D$_2$O, 400 MHz) δ 3.89 (t, J=6.3 Hz, 1H), 2.96 (t, J=7.6 Hz, 2H), 2.51-2.58 (m, 4H), 1.99-2.10 (m, 2H), 1.82 (quin, J=7.3 Hz, 2H); $^{13}$C NMR (D$_2$O, 100 MHz) δ 172.8, 52.6, 38.3, 29.7, 27.3, 26.2 (2 carbons); HRESI calculated for C$_7$H$_{17}$N$_2$O$_2$S ([M+H]$^+$) m/z 193.1005; measured m/z 193.1019.

Example (2S)-2-amino-4-[(3-aminopropyl)selanyl]butanoic acid (compound 15-Se)

FIG. 13 with 3-bromopropylamine hydrobromide yielded compound 15-Se (5.7 mg, 86% yield) as a white solid. $^1$H NMR (D$_2$O, 400 MHz) δ 3.97 (t, J=6.3 Hz, 1H), 2.94 (t, J=7.4 Hz, 2H), 2.56 (m, 4H), 2.08-2.13 (m, 2H), 1.87 (quin, J=7.4 Hz, 2H); $^{13}$C NMR (D$_2$O, 100 MHz) δ 172.0, 52.9, 39.1, 30.6, 27.2, 19.1, 17.5. HRESI calculated for C$_7$H$_{17}$N$_2$O$_2$Se ([M+H]$^+$) m/z 241.0450; measured m/z 241.0465.

Example (2S)-2-amino-4-[(2E)-penta-2,4-dien-1-ylsulfanyl] butanoic acid (compound 16)

According to the protocol reported by Sato et al., [28] to a 50 mL solution of 1,4-pentadien-3-ol (0.5 g, 5.94 mmol) in water was added 48% HBr in water (1.2 g, 7.13 mmol) drop wise. The reaction was stirred at 0° C. until TLC indicated the reaction was complete (~2 h). The reaction was then diluted with ether and washed with NaHCO$_3$ (sat, 3×30 mL), water, and brine. The organic layer was dried with Na$_2$SO$_4$ and concentrated in vacuo to afford 4-bromo-1,3-pentadiene (0.46 g, 3.2 mmol) as a yellow liquid with a yield of 53%. FIG. 10 with this 4-bromo-1,3-pentadiene yielded compound 16 (1.4 mg, 22%) as a white solid. $^1$H NMR (D$_2$O, 400 MHz) δ 6.10 (dt, J=17.1, 10.2 Hz, 1H), 5.92 (dd, J=15.3, 10.6 Hz, 1H), 5.42 (dt, J=15.1, 7.7 Hz, 1H), 4.94 (dd, J=16.8, 1.6 Hz, 1H), 4.80 (dd, J=10.8, 1.4 Hz, 1H), 3.91 (t, J=6.5 Hz, 1H), 2.95 (d, J=7.4 Hz, 2H), 2.35 (t, J=7.2 Hz, 2H), 1.80-1.99 (m, 2H); $^{13}$C NMR (D$_2$O, 100 MHz) δ 171.2, 136.1, 133.5, 129.2, 117.2, 51.3, 32.1, 29.0, 24.8. HRESI calculated for C$_9$H$_{16}$NO$_2$S ([M+H]$^+$) m/z 202.0896; measured m/z 202.0905.

Example (2S)-2-amino-4-[(2-azidoethyl)sulfanyl]butanoic acid (compound 17)

FIG. 9 with dibromomoethane (0.46 mL, 5.32 mmol) yielded a mixture of dibromoethane:1-azido-2-bromoethane (1:2, 1.0 g). FIG. 10 with this mixture yielded compound 17 (2.1 mg, 33% yield) as a white solid together with dimer Compound 28 (4.2 mg, 46% yield) as a white solid. Compound 17: $^1$H NMR (D$_2$O, 400 MHz) δ 3.88 (t, J=6.5 Hz, 1H), 3.39 (t, J=6.5 Hz, 2H), 2.65 (t, J=6.5 Hz, 2H), 2.58 (t, J=7.4 Hz, 2H), 1.96-2.11 (m, 2H); $^{13}$C NMR (D$_2$O, 100 MHz) δ 172.6, 52.5, 50.2, 30.2, 29.8, 26.5; HRESI calculated for C$_6$H$_{13}$N$_4$O$_2$S ([M+H]$^+$) m/z 205.0754; measured m/z 205.0767.

Example (2S)-2-amino-4-[(3-methylbutyl)sulfanyl]butanoic acid (compound 18)

FIG. 10 with 1-bromo-3-methylbutane yielded compound 18 (6.5 mg, 99% yield) as a white solid. $^1$H NMR (D$_2$O/TFA=20/1, 400 MHz) δ 4.03 (t, J=6.5 Hz, 1H), 2.52 (t, J=7.4 Hz, 2H), 2.41 (t, J=7.8 Hz, 2H), 1.94-2.05 (m, 2H), 1.38-1.47 (m, 1H), 1.23-1.31 (q, J=7.6 Hz, 2H), 0.68 (d, J=6.7 Hz, 6H); $^{13}$C NMR (D$_2$O/TFA=20/1, 100 MHz) δ 171.5, 51.6, 37.5, 29.3, 28.7, 26.6, 26.1, 21.3 (2 carbons). HRESI calculated for C$_9$H$_{20}$NO$_2$S ([M+H]$^+$) m/z 206.1209; measured m/z 206.1223.

Example (2S)-2-amino-4-[(3-methylbut-2-en-1-yl)sulfanyl] butanoic acid (compound 19)

A protocol identical to that described for compound 3 using L-Homocystine (150 mg, 0.559 mmol) and 3,3-dimethylallyl bromide (250 μL, 2.15 mmol) gave compound 19 (304 mg, 76% yield) as a white amorphous solid. $^1$H NMR (DMSO-d$_6$/TFA-d$_1$=20/1, 500 MHz) δ 5.16 (t, J=7.8 Hz, 1H), 4.00 (t, J=6.2 Hz, 1H), 3.12 (d, J=7.7 Hz, 2H), 2.49-2.56 (m, 2H), 1.94-2.04 (m, 2H), 1.68 (s, 3H), 1.61 (s, 3H); $^{13}$C NMR (DMSO-d$_6$/TFA-d$_1$=20/1, 125 MHz) δ 175.8, 140.1, 125.7, 56.3, 35.5, 33.8, 31.3, 30.7, 22.9; HRESI calculated for C$_9$H$_{18}$NO$_2$S ([M+H]$^+$) m/z 204.1053; measured m/z 204.1053.

Example (2S)-2-amino-4-[(3-methylbut-2-en-1-yl)selanyl] butanoic acid (compound 19-Se)

FIG. 13 with 3,3-dimethylallyl bromide yielded compound 19-Se (2.8 mg, 41% yield) as a white solid. $^1$H NMR (D$_2$O/TFA=20/1, 400 MHz) δ 5.19-5.26 (m, 1H), 3.92 (t, J=6.3 Hz, 1H), 3.17 (d, J=8.6 Hz, 2H), 2.49 (t, J=8.0 Hz, 2H), 2.04-2.18 (m, 2H), 1.59 (s, 3H), 1.52 (s, 3H); $^{13}$C NMR (D$_2$O/TFA=20/1, 100 MHz) δ 175.8, 140.1, 125.7, 56.4, 35.5, 33.8, 31.3, 30.7, 22.9. HRESI calculated for $C_9H_{18}NO_2Se$ ([M+H]$^+$) m/z 252.0497; measured m/z 252.0512.

Example (2S)-2-amino-4-(cyclohex-2-en-1-ylsulfanyl)butanoic acid (compound 20)

FIG. 11 with 3-bromo-cyclohexene yielded compound 20 (4.6 mg, 30% yield) as a white solid. $^1$H NMR (D$_2$O, 400 MHz) δ 5.70-5.77 (m, 1H), 5.56 (d, J=8.2 Hz, 1H), 4.01 (dt, J=6.4, 0.3 Hz, 1H), 3.37 (br. s, 1H), 2.54-2.69 (m, 2H), 1.97-2.20 (m, 2H), 1.77-1.89 (m, 3H), 1.39-1.66 (m, 3H); $^{13}$C NMR (D$_2$O, 100 MHz) δ 171.8, 131.1, 126.7, 51.9, 39.94, 39.91, 28.54, 28.51, 24.2, 19.0; HRESI calculated for $C_{10}H_{18}NO_2S$ ([M+H]$^+$) m/z 216.1053; measured m/z 216.1043.

Example (2S)-2-amino-4-(cyclohex-2-en-1-ylselanyl)butanoic acid (compound 20-Se)

FIG. 13 with 3-bromo-cyclohexene yielded compound 20-Se (1.3 mg, 18% yield) as a white solid. $^1$H NMR (D$_2$O, 400 MHz) δ 5.64-5.72 (m, 2H), 3.90 (m, 1H), 3.58-3.66 (m, 1H), 2.86 (t, J=1.00 Hz, 1H), 2.52-2.68 (m, 2H), 2.05-2.20 (m, 2H), 1.90 (br. s, 2H), 1.50-1.70 (m, 3H); $^{13}$C NMR (D$_2$O, 100 MHz) δ 172.3, 131.4, 127.7, 53.4, 36.2, 31.5, 29.5, 24.2, 19.2, 17.6; HRESI calculated for $C_{10}H_{18}NO_2S$ ([M+H]$^+$) m/z 264.0497; measured m/z 264.0508.

Example (2S)-2-amino-4-[(3-azidopropyl)sulfanyl]butanoic acid (compound 21)

FIG. 9 with dibromopropane (0.50 mL, 4.98 mmol) yielded a mixture of dibromopropane:1-azido-3-bromopropane (2:5, 1.0 g). FIG. 10 with this mixture yielded compound 21 (1.7 mg, 25% yield) as a white solid together with dimer compound 29 (1.0 mg, 10% yield) as a white solid. Compound 21: $^1$H NMR (D$_2$O, 400 MHz) δ 3.93 (t, J=6.5 Hz, 1H), 3.26 (t, J=6.7 Hz, 2H), 2.54 (t, J=7.6 Hz, 2H), 2.49 (t, J=7.2 Hz, 2H), 1.93-2.14 (m, 2H), 1.70 (quin, J=6.8 Hz, 2H); $^{13}$C NMR (D$_2$O, 100 MHz) δ 172.3, 52.3, 49.7, 29.5, 27.69, 27.65, 26.3. HRESI calculated for $C_7H_{15}N_4O_2S$ ([M+H]$^+$) m/z 219.0910; measured m/z 219.0919.

Example (2S)-2-amino-4-(benzylsulfanyl)butanoic acid (compound 22)

A protocol similar to that described for compound 3 using L-Homocystine (250 mg, 0.93 mmol) and benzyl bromide (0.13 mL, 1.12 mmol) was employed with slight modifications. Specifically, after the evaporation of NH$_3$ the dried residue was dissolved in 15 mL ddH$_2$O and the pH subsequently adjusted to 7 by adding 1 M HCl. A heavy precipitate formed, which was filtered and washed with cold ddH$_2$O (3×10 mL). The filtrate was purified by recrystallization from ethanol to provide compound 22 (0.15 g, 72% yield). $^1$H NMR (D$_2$O/TFA=20/1, 400 MHz) δ 7.08-7.19 (m, 5H), 3.92 (t, J=6.3 Hz, 1H), 3.57 (s, 2H), 2.37 (t, J=8.2 Hz, 2H), 1.84-2.04 (m, 2H); $^{13}$C NMR (D$_2$O, 100 MHz) δ 171.3, 138.0, 128.8 (2 carbons), 128.7 (2 carbons), 127.2, 51.4, 34.6, 29.1, 25.5; HRESI calculated for $C_{11}H_{15}NO_2SNa$ ([M+Na]$^+$) m/z 248.0716; measured m/z 248.0716.

Example (2S)-2-amino-4-(benzylselanyl)butanoic acid (compound 22-Se)

FIG. 11 with L-selenomethionine (100 mg, 0.51 mmol) and benzyl bromide (0.24 mL, 2.03 mmol) yielded compound 22-Se (10 mg, 7% yield) as a white solid and L-selenohomocystine (70 mg, 0.19 mmol, 38% yield). $^1$H NMR (D$_2$O, 400 MHz) δ 7.11 (s, 2H), 7.10 (s, 2H), 7.00-7.06 (m, 1H), 3.86 (t, J=6.5 Hz, 1H), 3.62 (s, 2H), 2.33-2.39 (m, 2H), 1.90-1.97 (m, 2H); $^{13}$C NMR (D$_2$O, 100 MHz) δ 171.2, 139.2, 129.0 (2 carbons), 128.6 (2 carbons), 126.8, 46.4, 42.9, 30.3, 26.2; HRESI calculated for $C_{11}H_{16}NO_2Se$ ([M+H]$^+$) m/z 274.0341; measured m/z 274.0339.

Example (2S)-2-amino-4-{[(2E)-4-azidobut-2-en-1-yl]sulfanyl}butanoic acid (compound 23)

FIG. 9 with (E)-1,4-dibromobut-2-ene (2.0 g, 9.34 mmol) yielded a mixture of (E)-1-azido-4-bromobut-2-ene:(E)-1,4-dibromobut-2-ene (3:2, 2.31 g). FIG. 10 with this (E)-1-azido-4-bromobut-2-ene:(E)-1,4-dibromobut-2-ene mixture yielded 23 (1.3 mg, 18% yield) as a white solid together with dimer compound 30 (2.3 mg, 23% yield) as a white solid. Compound 23: $^1$H NMR (D$_2$O, 400 MHz) δ 5.52-5.69 (m, 2H), 3.94 (t, J=6.5 Hz, 1H), 3.66 (d, J=6.3 Hz, 2H), 3.09 (d, J=6.7 Hz, 2H), 2.49 (t, J=7.4 Hz, 2H), 1.92-2.12 (m, 2H); $^{13}$C NMR (D$_2$O, 100 MHz) δ 172.2, 130.9, 126.4, 52.1, 51.6, 31.7, 29.3, 24.9; HRESI calculated for $C_8H_{15}N_4O_2S$ ([M+H]$^+$) m/z 231.0910; measured m/z 231.0922.

Example (2S)-2-amino-4-{[(2E)-4-azidobut-2-en-1-yl]selanyl}butanoic acid (compound 23-Se)

FIG. 12 with the (E)-1-azido-4-bromobut-2-ene:(E)-1,4-dibromobut-2-ene mixture in the synthesis of compound 23 yielded compound 23-Se (3.1 mg, 36% yield) as a white solid. $^1$H NMR (D$_2$O, 400 MHz) δ 5.77-5.88 (m, 1H), 5.42-5.51 (m, 1H), 3.89 (t, J=6.1 Hz, 1H), 3.44 (d, J=6.7 Hz, 2H), 3.12 (d, J=7.4 Hz, 2H), 2.41-2.50 (m, 2H), 2.07-2.10 (m, 2H); $^{13}$C NMR (D$_2$O, 100 MHz) δ 169.8, 134.2, 122.7, 53.2, 40.3, 30.5, 23.3, 16.8; HRESI calculated for $C_8H_{15}N_4O_2Se$ ([M+H]$^+$) m/z 279.0355; measured m/z 279.0348.

Example (2S)-2-amino-4-{[(2E)-4-aminobut-2-en-1-yl]selanyl}butanoic acid (compound 24-Se)

(E)-1-azido-4-bromobut-2-ene was synthesized according to the procedure reported by Islam et al.[29] (E)-1,4-dibromobut-2-ene (2 g, 9.34 mmol) was placed in a round-bottom flask and dissolved in THF (10 mL). Sodium azide (800 mg, 12.2 mmol) was dissolved in 1 mL water and mixed the solution of (E)-1,4-dibromobut-2-ene. The reaction was stirred overnight at room temperature, diluted with diethyl ether (100 mL) and successively washed with water (15 mL) and saturated NaCl solution (15 mL). The organic layer was dried over anhydrous $Na_2SO_4$ and evaporated under reduced pressure. Crude products were purified by flash silica gel column chromatography using EtOAc/Hexanes affording 200 mg of (E)-1-azido-4-bromobut-2-ene (25% yield) and 320 mg of (E)-1,4-diazidobut-2-ene (25% yield), both as colorless liquids. FIG. 13 with (E)-1-azido-4-bromobut-2-ene yielded compound 24-Se (2.6 mg, 45% yield) as a white solid. $^1$H NMR ($D_2O$, 400 MHz) δ 5.71-6.05 (m, 1H), 5.37-5.59 (m, 1H), 3.75 (t, J=6.1 Hz, 1H), 3.45 (d, J=6.7 Hz, 2H), 3.12 (d, J=7.4 Hz, 2H), 2.37-2.45 (m, 2H), 2.01-2.07 (m, 2H); $^{13}$C NMR ($D_2O$, 100 MHz) δ 173.2, 134.1, 122.8, 54.0, 40.4, 30.9, 23.3, 16.7; HRESI calculated for $C_8H_{17}N_2O_2Se$ ([M+H]$^+$) m/z 253.0450; measured m/z 253.0464.

Example (2S)-2-amino-4-{[(4-methylphenyl)methyl]sulfanyl}butanoic acid (compound 25)

FIG. 10 with 4-methylbenzyl bromide yielded compound 25 (2.0 mg, 27% yield) as a white solid. $^1$H NMR ($D_2O$, 400 MHz) δ 7.05 (d, J=8.0 Hz, 2H), 7.00 (d, J=8.0 Hz, 2H), 3.93 (t, J=6.3 Hz, 1H), 3.53 (s, 2H), 2.36 (t, J=7.4 Hz, 2H), 2.07 (s, 3H), 1.90-2.09 (m, 2H); $^{13}$C NMR ($D_2O$, 100 MHz) δ 171.3, 137.4, 134.9, 129.2 (2 carbons), 128.8 (2 carbons), 51.5, 34.3, 29.1, 25.6, 19.9; HRESI calculated for $C_{12}H_{18}NO_2S$ ([M+H]$^+$) m/z 240.1053; measured m/z 240.1061.

Example (2S)-2-amino-4-{[(2E)-3-phenylprop-2-en-1-yl]sulfanyl}butanoic acid (compound 26)

FIG. 10 with 3-bromo-1-phenyl-1-propene yielded compound 26 (4.2 mg, 54% yield) as a white solid. $^1$H NMR ($D_2O$, 400 MHz) δ 7.23 (d, J=7.0 Hz, 2H), 7.13 (t, J=7.4 Hz, 2H), 7.05 (dd, J=14.5, 7.4 Hz, 1H), 6.32 (d, J=16.0 Hz, 1H), 6.03 (dt, J=16.0, 7.4 Hz, 1H), 3.96 (t, J=6.5 Hz, 1H), 3.14 (d, J=7.4 Hz, 2H), 2.44 (t, J=7.4 Hz, 2H), 1.93-2.05 (m, 2H); $^{13}$C NMR ($D_2O$, 100 MHz) δ 171.3, 136.4 (2 carbons), 132.1, 128.7 (2 carbons), 126.2, 125.5, 110.0, 51.6, 32.8, 29.2, 24.9; HRESI calculated for $C_{13}H_{18}NO_2S$ ([M+H]$^+$) m/z 252.1053; measured m/z 252.1075.

Example (2S)-2-amino-4-{[(4-nitrophenyl)methyl]sulfanyl}butanoic acid (compound 27)

FIG. 11 with 4-nitrobenzyl bromide yielded compound 27 (3.6 mg, 18% yield) as a white solid. $^1$H NMR ($D_2O$, 400 MHz) δ 8.06 (d, J=9.0 Hz, 2H), 7.43 (d, J=9.0 Hz, 2H), 3.94 (t, J=6.5 Hz, 1H), 3.75 (s, 2H), 2.45 (t, J=7.0 Hz, 2H), 1.90-2.09 (m, 2H); $^{13}$C NMR ($D_2O$, 100 MHz) δ 171.7, 146.6, 129.7 (2 carbons), 123.8 (2 carbons), 117.6, 51.7, 34.2, 29.2, 25.8; HRESI calculated for $C_{11}H_{15}N_2O_4S$ ([M+H]$^+$) m/z 271.0747; measured m/z 271.0761.

Example (2S)-2-amino-4-{[(4-nitrophenyl)methyl]selanyl}butanoic acid (compound 27-Se)

FIG. 13 with 4-nitrobenzyl bromide yielded compound 27-Se (1.6 mg, 18% yield) as a white solid. $^1$H NMR ($D_2O$, 400 MHz) δ 8.05 (d, J=9.0 Hz, 2H), 7.41 (d, J=9.0 Hz, 2H), 3.88 (t, J=6.4 Hz, 1H), 3.83 (s, 2H), 2.47 (t, J=6.8 Hz, 2H), 1.96-2.03 (m, 2H); $^{13}$C NMR ($D_2O$, 100 MHz) δ 171.9, 147.9, 146.2, 129.5 (2 carbons), 123.9 (2 carbons), 52.9, 30.5, 25.4, 17.7; HRESI calculated for $C_{11}H_{15}N_2O_4SE$ ([M+H]$^+$) m/z 319.0192; measured m/z 319.0201.

Example (2S)-2-amino-4-[(2-{[(3S)-3-amino-3-carboxypropyl]sulfanyl}ethyl)sulfanyl]butanoic acid (compound 28)

FIG. 9 with dibromoethane (0.46 mL, 5.32 mmol) yielded a mixture of dibromoethane:1-azido-2-bromoethane (1:2, 1.0 g). FIG. 10 with this dibromoethane:1-azido-2-bromoethane mixture yielded compound 17 (2.1 mg, 33%) as a white solid together with dimer compound 28 (4.2 mg, 46%) as a white solid. Compound 28: $^1$H NMR ($D_2O$, 400 MHz) δ 3.95 (t, J=6.3 Hz, 2H), 2.68 (s, 4H), 2.58 (t, J=7.4 Hz, 4H), 1.94-2.15 (m, 4H); $^{13}$C NMR ($D_2O$, 100 MHz) δ 172.2 (2 carbons), 52.1 (2 carbons), 30.4 (2 carbons), 29.6 (2 carbons), 26.3 (2 carbons); HRESI calculated for $C_{10}H_{21}N_2O_4S_2$ ([M+H]$^+$) m/z 297.0937; measured m/z 297.0949.

Example (2S)-2-amino-4-[(3-{[(3S)-3-amino-3-carboxypropyl]sulfanyl}propyl)sulfanyl]butanoic acid (compound 29)

FIG. 9 with dibromopropane (0.50 mL, 4.98 mmol) yielded a mixture of dibromopropane:1-azido-3-bromopropane (2:5, 1.0 g). FIG. 10 with this dibromopropane:1-azido-3-bromopropane mixture yielded compound 21 (1.7 mg, 25% yield) as a white solid together with dimer compound 29 (1.0 mg, 10% yield) as a white solid. Compound 29: $^1$H NMR ($D_2O$, 400 MHz) δ 3.96 (t, J=6.3 Hz, 2H), 2.56 (d, J=7.6 Hz, 4H), 2.50 (d, J=7.2 Hz, 4H), 1.96-2.12 (m, 4H), 1.71 (quin, J=7.1 Hz, 2H); $^{13}$C NMR ($D_2O$, 100 MHz) δ 172.1 (2 carbons), 52.0 (2 carbons), 29.5 (2 carbons), 29.3 (2 carbons), 27.9, 26.2 (2 carbons). HRESI calculated for $C_{11}H_{23}N_2O_4S_2$ ([M+H]$^+$) m/z 311.1094; measured m/z 311.1101.

Example (2S)-2-amino-4-{[(2E)-4-{[(3S)-3-amino-3-carboxypropyl]sulfanyl}but-2-en-1-yl]sulfanyl}butanoic acid (Compound 30)

FIG. 9 with (E)-1,4-dibromobut-2-ene (2.0 g, 9.34 mmol) yielded a mixture of (E)-1-azido-4-bromobut-2-ene:(E)-1,4-dibromobut-2-ene (3:2, 2.31 g). FIG. 10 with this (E)-1-azido-4-bromobut-2-ene:(E)-1,4-dibromobut-2-ene mixture yielded 23 (1.3 mg, 18% yield) as a white solid together with dimer compound 30 (2.3 mg, 23% yield) as a white solid. Compound 30: $^1$H NMR ($D_2O$, 400 MHz) δ 5.42-5.49 (m, 2H), 3.98 (t, J=6.5 Hz, 2H), 3.02-3.10 (m, 4H), 2.48 (t, J=7.4 Hz, 4H), 1.92-2.15 (m, 4H); $^{13}$C NMR ($D_2O$, 100 MHz) δ 171.9 (2 carbons), 128.9 (2 carbons), 51.9 (2 carbons), 31.8 (2 carbons), 29.2 (2 carbons), 25.0 (2 carbons); HRESI calculated for $C_{12}H_{23}N_2O_4S_2$ ([M+H]$^+$) m/z 323.1094; measured m/z 323.1102.

Gene cloning and protein expression and purification. The *Escherichia Coli* MAT (eMAT) was amplified using colony PCR from the cells of *E. Coli* BL21(DE3) strain using primers

5'-ATACTGCATATGGCAAAACACCTTTTTACG (forward, NdeI), per SEQ ID NO: 2, and

5'-CAGTATGGATCCTTACTTCAGACCGGCAGC (reverse, BamHI), per SEQ ID NO: 3. The PCR products were digested with respective restriction enzymes and ligated into pET28a vector to provide expression plasmids for proteins bearing N-terminal-His$_6$ fusions. The expression constructs for *Homo Sapiens* MATs (hMATs) were provided by Prof. Chunming Liu. The *Methanocaldococcus jannaschii* MAT (mMAT) gene was synthesized (sequence provided in SEQ ID NO: 1) by GenScript (Piscataway, N.J.) with N-terminal NdeI and C-terminal EcoRI restriction sites and subsequently also subcloned in the pET28a vector to provide an expression construct for the N-terminal-His$_6$ fusion. Expression and purification of rebeccamycin methyltransferase, RebM was carried out as described in Zhang et al.[5a] The *E. coli* S-adenosylhomocysteine nucleosidase (EC 3.2.2.9) (also known as SAH hydrolase) gene was amplified from the genome of *E. coli* BL21(DE3), using primers

5'-AGCCATATGAAAATCGGCATCATTGGTG (forward, NdeI), per SEQ ID NO: 4, and

5'-ATAGAATTCTTAGCCATGTGCAAGTTTCTG (reverse, EcoRI), per SEQ ID NO: 5. The PCR products were digested with respective restriction enzymes and ligated into pET28a vector to provide expression plasmids for the corresponding N-terminal-His$_6$ fusion protein.

All five MATs with N-terminal-His$_6$ (herein referred to simply as hMAT1A, hMAT2A, hMAT2, eMAT, and mMAT), RebM and SAH hydrolase were expressed in a corresponding *E. coli* BL21(DE3) host in the presence of 35 μg mL$^{-1}$ of kanamycin at 37° C. to an OD$_{600}$ of ~0.6, induced with 0.5 mM IPTG, and continued to grow at 37° C. for another 4 h. The cells were harvested by centrifugation (30 min, 5000 rpm), resuspended in buffer A (20 mM NaH$_2$PO$_4$, 300 mM NaCl, 10 mM imidazole, pH 7.8). The cells were lysed via incubation with 1 mg mL$^{-1}$ lysozyme (~50,000 U mg$^{-1}$; Sigma-Aldrich, St. Louis, Mo., USA) for 30 min on ice followed by sonication (VirSonic 475; Virtis, Gardiner, N.Y.; 100 W, 4×30 s pulses, ~1 min between pulses) on ice. MATs were purified via affinity chromatography (5 mL HiTrap Ni-NTA chelating column, GE Healthcare, Piscataway, N.J.) following standard linear gradient (50 mM NaH$_2$PO$_4$, 300 mM NaCl, pH 8.0 with a linear gradient of imidazole of 10-500 mM) using an AKTA Purifier 10 (GE Healthcare). Buffer exchange of pooled fractions containing the purified protein was accomplished using a PD-10 column (GE Healthcare) eluted with 25 mM Tris-HCl, 80 mM KCl, pH 8. Protein concentrations were determined by Bradford assay (Bio-Rad, Hercules, Calif., USA) using BSA as a standard. For this study, all proteins retained the N-terminal-His$_6$ affinity tag.

MAT Assay

In vitro MAT reactions were conducted in a volume of 50 μl with 2 mM S/Se-alkylated analog (compounds 2-30), 1 mM ATP and 5 μM purified MAT in 25 mM Tris buffer pH 8.0, 5 mM MgCl$_2$, 50 mM KCl for 4 h. The sMAT and mMAT reactions were conducted at 65° C. while hMATs and eMAT were incubated at 37° C. Reactions were quenched by adding an equal volume of methanol followed by centrifugation (10,000×g for 15 min) to remove the precipitated protein and product formation for each reaction was subsequently analyzed by RP-HPLC using Method D (FIG. 15, first column). For each reaction, percent yield was based upon the integration of species at 254 nm and calculated by dividing the integrated area of product and/or decomposed product by the sum of integrated area of product and/or decomposed product and the remaining substrate. The assays were repeated twice under identical conditions, and Table 2 (and FIG. 5) represents an average value of two assays. The inclusion of adenine and 5'-R-thio-5'-adenosine in these calculations is based upon the established SAM and ATP chemical decomposition pathways which indicate adenine and 5'-R-thio-5'-adenosine to only derive from SAM (not ATP). All putative products were subsequently confirmed by high resolution electrospray ionization (ESI) mass spectra with positive (+) and/or negative (−) mode.

Example

FIG. 18 illustrates the synthesis of (seleno)methionine analogs, use of a high-throughput MAT assay, and product verification via LC/MS.

Coupled hMAT2/RebM Assay

In vitro hMAT2-RebM coupled reactions were carried out in a volume of 25 μl with 2 mM S/Se-alkylated analogs, 1 mM ATP, 50 μM rebeccamycin ortholog compound 31 (synthesized as previously described), [30] 5 μM hMAT2, 10 μM RebM, 5 μM SAH hydrolase in 25 mM Tris buffer pH 8.0, 5 mM MgCl$_2$, 50 mM KCl for 24 h at 37° C. Reactions were quenched by adding an equal volume of methanol followed by centrifugation (10,000 g for 15 min) to remove the precipitated protein and the product formation for each reaction was subsequently analyzed by RP-HPLC using Method E (FIG. 15, middle column). The assays were repeated twice under identical conditions and Table 2 (and FIG. 8) represents an average value of two assays. The reactions were scaled (>500 μM compound 31), purified by semi-prep HPLC using Method E and the putative new products were confirmed by NMR (Table 3) and HRMS.

TABLE 3

| NMR Chemical Shifts (in PPM) of 4'O—R-Rebeccamycin in CD$_3$OD; where R = | | | | | | |
|---|---|---|---|---|---|---|
| Atom | —H | —CH$_3$ | —CH$_2$CH$_3$ | —CH$_2$CHCH$_2$ | —CH$_2$CCH | —CH$_2$CCN |
| C1'/H1' | 86.2/6.20 | 86.2/6.20 | 86.2/6.20 | 86.2/6.20 | 86.2/6.20 | 86.2/6.20 |
| C2'/H2' | 74.5/3.83 | 74.6/3.83 | 74.4/3.82 | 74.8/3.81 | 74.9/3.82 | 74.8/3.82 |
| C3'/H3' | 78.3/3.74 | 78.2/3.83 | 78.2/3.82 | 78.3/3.87 | 78.6/3.89 | 78.3/3.95 |

TABLE 3-continued

NMR Chemical Shifts (in PPM) of 4'O—R-Rebeccamycin in $CD_3OD$; where R =

| Atom | —H | —$CH_3$ | —$CH_2CH_3$ | —$CH_2CHCH_2$ | —$CH_2CCH$ | —$CH_2CCN$ |
|---|---|---|---|---|---|---|
| C4'/H4' | 69.0/4.26 | 78.8.0/3.98 | 77.0/4.07 | 77.0/4.14 | 76.8/4.21 | 78.0/4.26 |
| C5'/H5' | 80.3/3.99 | 79.2/3.99 | 79.2/3.99 | 79.2/4.05 | 79.2/4.05 | 78.73/4.12 |
| C6'/H6', H6" | 59.8/4.25, 4.03 | 59.9/4.13, 4.03 | 59.9/4.13, 4.03 | 60.0/4.15, 4.05 | 60.2/4.24, 4.04 | 60.1/4.17, 4.06 |
| 4-O'—$H_3$ | NA | 61.1/3.79[a] | NA | NA | NA | NA |
| 4-O'—$CH_2CH_3$ | NA | NA | (69.5/4.09, 3.96) (15.9/1.33) | NA | NA | NA |
| 4-O'—$CH_2CHCH_2$ | NA | NA | NA | (74.9/4.59, 4.44) (6.10) (5.39, 5.22) [a],[b] | NA | NA |
| 4-O'—$CH_2CCH$ | NA | NA | NA | NA | (61.0/4.70, 4.63) (2.92)[c] | NA |
| 4-O'—$CH_2CCN$ | NA | NA | NA | NA | NA | (58.3/4.85)[a] |

[a]resonances listed as C1"/H1", C2"/H2", C3"/H3" in sequential order;
[b]13C C2"(CH) and C3" ($CH_2$) were not observed in the HSQC;
[c]13C C3" (CH) was not observed in the HSQC.

Example II

The MAT from *Sulfolobus solfataricus* (sMAT), an enzyme from a poorly explored class of the MAT family, has the ability to produce a range of differentially alkylated SAM analogs in the presence of non-native methionine analogs and ATP. To investigate the molecular basis for SAM analog production, the sMAT in the SAM bound, S-adenosylethionine (SAE) bound, and unbound forms was crystallized. Notably, among these structures, the SAE-bound form offers the first MAT structure containing a non-native product and cumulatively, these structures add new structural insight into the MAT family and allow for detailed active site comparison with its homologs in *E. coli* and humans. As the only existing thermostable MAT structures from archaea, the structures herein also provide as a basis for future engineering to broaden SAM analog production as reagents for methyltransferase-catalyzed 'alkyl-randomization' and/or the study of methylation in the context of biological processes.

Some members of the MAT family accommodate non-native methionine analogs [9, 55] and, in the context of coupled reactions containing permissive methyltransferases, enable the ability for natural product 'alkylrandomization'.

A sequence divergent class of MATs has been identified in archaea [37, 47], with only ~20% sequence identity with *E. coli* and human MATs. However, structural information and broad substrate specificity assessment for members of this divergent class of MATs is lacking. The present disclosure provides *Sulfolobus solfataricus* MAT (sMAT) to enable the cumulative synthesis of a broad panel of unnatural SAM analogs (31 analogs detected) starting from synthetic S/Se-alkylated Met analogs (42 analogs) or commercial sources (3 analogs).

Interestingly, in contrast to its low sequence similarity to other MATs, sMAT displays the typical three-domain fold and partly conserved active site architecture. Unlike other known MAT structures, the activity of sMAT cannot be stimulated by ionic potassium [47]. This can be supported structurally by the presence of a lysine side chain (K63) in sMAT, which likely has a similar function to potassium ion in other MATs. Further, the capture of the first atypical ligand bound structure of MAT provides insights on the nature of sMAT broad substrate specificity and a template for expanding the substrate scope. The present disclosure expose sMAT as an efficient catalyst for SAM analog production that is amendable to downstream SAM-utilizing processes.

Overall Structural Organization:

The crystal structures of sMAT have been determined successfully at 2.19 Å or 2.39 Å resolution for the SAM-liganded form, 2.49 Å for the SAE-liganded form and 2.21 Å for the unliganded form. Similar to *E. coli* MAT (eMAT) [52], Rat liver MAT (rlMAT) [35], human MATs (hMAT1A and hMAT2A) [49], sMAT packs as a tetramer. All four sMAT structures contain two subunits, A and B, in the asymmetric unit and the tetramer is formed by a 2-fold crystallographic symmetry axis. The buried surface interface between the two subunits A and B, and the two dimers AB and CD are calculated to be 2570 and 1870 Å$^2$ respectively [41]. In the tetramer, there are four potential ligand-binding sites: two sites sandwiched by A and B, and the other two sites between C and D. Compared with other known MAT structures [43], the sMAT monomer adopts a similar 3-domain architecture with secondary structure variants. Interestingly, unlike other MATs, structural variations were observed between subunits A and B in sMAT with an average root mean square deviation (rmsd) of 0.51 Å in both the liganded and unliganded structures. In addition, the maximum rmsd between all the A subunits and the maximum rmsd between all the B subunits in all sMAT structures are calculated as 0.29 Å and 0.21 Å, respectively. As a result, half of the active sites are in a more open conformation.

Active Site Contents:

The MAT catalyzed SAM formation occurs via a sequential two-step mechanism. In the first step, SAM is formed by a direct $S_N2$ reaction, in which the sulfur atom of methionine attacks the C5' position of ATP and thus cleaves the polyphosphate chain from ATP. In the second step, the triphosphate is further hydrolysed to diphosphate (PPi) and phosphate (Pi)[43]. Komoto et al. identified two critical residues, lysine 165 and histidine 14, in eMAT for this proposed $S_N2$ reaction based on their ligand-bound structures. Interestingly, even with significant sequential variations to eMAT and other MATs, several conserved residues were observed in sMAT, mainly located around the active site, including the two crucial residues, lysine (K201) and histidine (H29) for the proposed $S_N2$ reaction.

The interaction between sMAT and products in the active site are multifaceted. The adenine ring of SAM is recognized by a hydrogen bond with the side chain of aspartate 144 and a stacking interaction with the aromatic ring of tyrosine 270. Several water molecules surrounding by the adenine ring also form a hydrogen bond network to the enzyme. The 2'-OH and 3'-OH of the adenosine ribose interact with the side chains of aspartate 199, aspartate 282 and serine 277. Similar interactions involving aspartic acids have been seen in other MAT structures bound with SAM, but not for serine [40, 50]. The methionine/ethionine moiety (of SAM and SAE, respectively) forms hydrogen bonds with four residues, in which the amino group interacts with the side chain of aspartate 282, and the carboxylate group interacts with the side chain of histidine 58, asparagine 60 and asparagine 159. The methyl or ethyl group is buried in a slightly hydrophobic pocket surrounded by asparagine 159, aspartate 160, isoleucine 349, leucine 145 and the adenine ring. As similar observations in eMAT [40], the PPi and Pi formed a U-shaped conformation with two magnesium ions closely stacked on both sides. Further, the two magnesium sites are formed with the side chains of aspartate 31, glutamate 305 and three water molecules. The phosphate groups are surrounded and stabilized by the side chains of several basic amino acids: lysine 25, histidine 29, lysine 201, arginine 288 and lysine 310.

As described, the ligands are solvent inaccessible and thus, the entrance of the active site requires a dynamic and flexible region. A flexible loop region was previously identified as the gate for the active site in MATs [53]. This gate loop feature has been confirmed by crystal structures of eMAT, hMAT2A and hMAT2B, in which the loop becomes ordered when ligands are bound and it becomes disordered when the active site is empty [40, 50]. A similar gating loop region was identified in sMAT, which has interactions with the adenine ring and the methionine or ethionine moiety.

Unusual Product Formation During Crystallization: Two sets of ligand bound crystals were obtained in the presence of 5 mM ADP, 10 mM ethionine (or methionine), 10 mM $Mg^{2+}$ ion, and 1.4 M $NaHPO_4/K_2HPO_4$. Thus based on the simulated annealing Fo-Fc omit map of the active site, one ADP, one PO4, two $Mg^{2+}$ and one ethionine (or methionine) molecule were initially built in. However, this model does not fit the electron density perfectly, because the Fo-Fc omit map does not agree with the placement of the crucial carbon atom. Thus, it is very clear that the product has already formed and a model including PPi and SAE (or SAM) is more appropriate. The new model has a lower temperature factor and a better real-space correlation to electron density in the active site. MAT-catalyzed SAM/SAE formation via ADP and Met/Eth has not been previously observed. In addition, incubation of sMAT in the presence of ADP and methionine at 65° C. for 4 hr under standard assay conditions led to no detectable product. Thus, two explanations for this unusual product formation have been proposed: (i) The sMAT protein is contaminated by ATP during expression or purification; (ii) The unusual reaction catalyzed by sMAT can actually occur in vitro, but may take as long as one month to finish, which corresponds to the length of crystal growth in this experiment.

Structure Homology:

A DALI search [38] for structures similar to the sMAT monomer returned several hits, all of which are previously solved MAT structures with Z-scores between 23 and 29. Those MAT structures share a very high level of overall sequence identity (>50%) and a high level of conservation among residues associated with substrates binding. Interestingly, sMAT only has a maximum sequence identity of 19% with these known MATs, but shares a similar three-domain.

For the comparison of active site residues, crystal structures of sMAT, eMAT [40] and hMAT2A [49] were aligned by ligands as described in the methods section. Surprisingly, 16 of 17 active site residues detected in sMAT have an identical or similar residue in eMAT and hMAT2A. The only extra residue sMAT has is H315, which forms hydrogen bond with $O_5$ in di-phosphate. DALI-based sequence alignment was able to identify 11 pairs of residues. Eight of them are conserved among sMAT and other MATs, including the crucial residues histidine and lysine for the proposed $S_N2$-like mechanism [40]. The other three pairs are very similar residues at the same spot: for example, in sMAT tyrosine 270 forms stacking interactions with the adenine ring of SAE/SAM, while in eMAT it is phenylalanine 230. Intriguingly, there are another 5 pairs of residues that are not detectable via DALI search: the side chain of sMAT lysine 25 (eMAT lysine 245) helps stabilize the tri-phosphate group; the side chains of sMAT histidine 58 and asparagine 60 (eMAT glutamine 98 and lysine 269) form hydrogen bonds with the carboxyl group of methionine or ethionine; the side chain of sMAT glutamate 305 (eMAT aspartate 271) form ionic bonds with the magnesium ion; the side chain of sMAT lysine 63 occupies the same spot as the eMAT potassium ion and helps stabilize the di-phosphate ligand.

Unlike other known MATs, it has been previously reported that the activity of sMAT cannot be enhanced by $K^+$ [47]. In the present study, all the crystals of sMAT were obtained from the crystallization condition containing more than 150 mM potassium, but electron density suitable for $K^+$ was not observed in any datasets. Combined with the active sites alignment evidence, it is very likely that the catalytic activity of sMAT is not affected by $K^+$, because the lysine in sMAT serves to present the requisite cation properties.

Substrate Specificity of sMAT:

The substrate specificity for sMAT based upon RP-HPLC is illustrated in FIG. 16 wherein observed 5'-methyl-thio (seleno)-5'-deoxyadenosine (MTA) production (via RP-HPLC) was interpreted as product based upon the well-established SAM decay pathways indicating MTA to directly derive from SAM (not ATP). [18, 11, 57] Of the 45 putative substrates tested with sMAT, 11 led to appreciable (>50%) SAM analog production, an additional 15 led to moderate (25-50%) conversion, while 5 offered detectable product (<25%) under the conditions described. In general, smaller alkyl substitutions were better tolerated, suggesting steric infringement to possibly prohibit larger substitutions. Interestingly, in the case where direct comparisons could be made, the degree of unsaturation correlated with a reduction in turnover (e.g., propyl>allyl>propargyl). Importantly, notable turnover was observed with branched analogs (FIG. 16) that previously led to only trace product with MATs studied to date.

A comparison of the kinetic parameters for L-methionine and the non-native substrate for which a ligand-bound structure is available (L-ethionine) reveals that the proficiency of the sMAT increases for both the substrates with an increase in temperature from 37° C. to 65° C., and correlates to both an increase in $k_{cat}$ and a decrease in $K_m$. At either temperature, the $k_{cat}$ values for the sMAT reaction with L-methionine or L-ethionine are similar and the reduced proficiency with L-ethionine when compared to the native substrate L-methionine derive from a combination of higher $K_m$ values for both L-ethionine and ATP.

Interestingly, eMAT and hMAT2A also have some ability to incorporate ethionine. The ethionine turns over with sMAT, and hMAT2A is near 100%, whereas eMAT is just 10%. A ligand-based alignment shows that sMAT has a larger cavity around the ethyl/methyl group than either hMAT2A or eMAT.

Also, branched analogs highlighted in FIG. 16 turnover significantly better with sMAT, comparing with eMAT, hMAT2A and mMAT (MAT from *Methanocaldococcus jannaschii*). Interestingly, mMAT is a thermophilic archaea MAT that has all active site residues conserved with sMAT. However, further comparison between their active site cavities cannot be conducted, because mMAT structure remains unknown. The current structural information suggests the better turnover rate of branched SAM analogs with sMAT is possibly mediated by some general orientation/dynamics of the gating loop and/or secondary shell variations.

Conclusions: sMAT has the characteristic fold and the typical tetramer assembly of known MATs. In addition, the slightly expanded substrate scope of sMAT over other MATs studied to date highlight sMAT as a useful tool for the production of SAM analogs. In conjunction with the demonstration of coupled MAT-methyltransferase systems for differential alkylation, this chemoenzymatic strategy circumvents a major liability in the use of synthetic SAM analogs—namely, the dramatic instability of the SAM analogs.

Further, the elucidation of the active site architecture with the atypical product bound, the characterization of the gating loop region, as well as the sMAT turnover reactions with different SAM analogs provide a blueprint for future SAM analog production.

Materials and Methods

Expression and Purification of sMAT:

The methionine adenosyltransferase (MAT) gene (UniProt accession: Q980S9) was cloned into NdeI/EcoRI-digested pET28a to enable production of recombinant N-His$_6$-sMAT). For protein production, the corresponding pET28a-sMAT construct was transformed into the *E. coli* methionine auxotroph strain B834 (DE3) and auto-induction media (Sreenath et al., 2005) was used for expression at 37° C. The cells were harvested by centrifugation at 5000 rpm for 30 min and resuspended in buffer 20 mM NaH$_2$PO$_4$, 300 mM NaCl, 10 mM imidazole pH 7.8. The cells were lysed via lysozyme incubation followed by sonication on ice. Subsequently, N-His6-sMAT was purified via Ni-NTA chelating column (GE Healthcare) following a protocol with a linear imidazole (10-500 mM) elution gradient (50 mM NaH$_2$PO$_4$, 300 mM NaCl, pH 8.0) The His$_6$-tag was removed by thrombin (Novagen) cleavage and the affinity tag was removed via a second round of Ni-NTA affinity chromatography. After the buffer exchange using PD-10 column (25 mM Tris-HCl, pH 8), the desired truncated Se-sMAT was concentrated to 27 mg/mL, flash frozen in liquid nitrogen and stored at −80° C. Protein concentrations were determined by Bradford assay (Bio-Rad, Hercules, Calif., USA) using BSA as a standard. Unless otherwise indicated, the term sMAT herein refers to SeMet-labeled sMAT after thrombin cleavage.

Crystallization, Diffraction, and Structure Determination:

General screens were performed with PEGRx HT, Crystal Screen HT, Index HT, and SaltRx HT (Hampton Research) utilizing a Mosquito® dispenser (TTP labTech) by the sitting drop method. Crystal growth was monitored by Bruker Nonius Crystal Farms at 20° C. All sMAT crystals with or without substrates were obtained by mixing 2 μL of protein solution and 2 μL of reservoir solution, 1.40 M sodium phosphate monobasic monohydrate/potassium phosphate dibasic pH 5.6, using the sitting drop method. For unbound sMAT crystals, the protein solution contained 0.15-0.2 mM sMAT and 25 mM Tris pH 8.0. For sMAT: (SAM) condition, the protein solution contains 0.15-0.2 mM sMAT, 1 mM SAM and 25 mM Tris pH 8.0. For sMAT: (ADP+Met/Eth), the protein solution contained 0.2-0.3 mM sMAT, 5 mM ADP, 10 mM Met (or Eth), 10 mM MgCl$_2$, 12.5 mM KCl, 7.5 mM DTT and 25 mM Tris pH 8. All crystals were cryoprotected by 25% DMSO or 25% ethylene glycol and flash frozen in liquid nitrogen.

X-ray diffraction data were collected at the Life Science Collaborative Access Team (LS-CAT) with an X-ray wavelength of 0.98 Å for all sMAT crystals at the Advanced Photon Source at Argonne National Laboratory. Datasets were indexed and scaled by HKL2000 or XDS [39, 46]. For structure solution of apo sMAT, phenix.HySS was used for determination of selenium atom sub-structure, AutoSol for phasing and phenix.autobuild for model building (Adams et al., 2010). For the other structures of sMAT with ligands, molecular replacement was utilized using the apo sMAT structure as a starting model. The structures including several double conformations were manually rebuilt in several rounds by Coot [33] and further refined by phenix.refine [31]. MolProbity was used to validate the quality of the coordinates [32]. All structural figures in this paper were generated using PyMOL [48].

Ligand-based Structural alignment of MAT homologs: In order to best compare the active site contents between structures with low sequence identity, four structures were aligned based on ligand positions by PyMOL. They are eMAT with SAM and PPNP (PDB code 1RG9) [40], hMAT2A with SAM (PDB code 2P02) [49], sMAT with SAM, PPi and PO$_4$ (PDB code 4K0B) and sMAT with SAE, PPi and PO$_4$ (4L2Z). 1RG9, 2P02 and 4K0B were first aligned by SAM molecule, and thus 4L2Z was aligned to 4K0B via several active site residues. Atom clashes were calculated in presence of hydrogen atoms using PyMOL and displayed as bumps.

In-vitro sMAT assay: In vitro sMAT reactions were conducted in a volume of 50 μl with 2 mM S/Se-alkylated analog, 1 mM ATP and 5 μM purified sMAT in 25 mM Tris buffer pH 8.0, 5 mM MgCl$_2$, 50 mM KCl for 4 h at 65° C. Reactions were quenched by adding an equal volume of methanol followed by centrifugation (10,000×g for 15 min) to remove the precipitated protein and product formation for each reaction was subsequently analyzed by reverse phase HPLC (RP-HPLC) using method described below. For each reaction, percent yield was based upon the integration of species at 254 nm and calculated by dividing the integrated area of product and/or decomposed product by the sum of integrated area of product and/or decomposed product and the remaining substrate. The assays were repeated twice under identical conditions, and Table 4 (and FIG. 17) represents an average value of two assays. The inclusion of adenine and 5'-R-thio-5'-adenosine in these calculations is based upon the established SAM and ATP chemical decomposition pathways which indicate adenine and 5'-R-thio-5'-adenosine to only derive from SAM (not ATP). All putative products were subsequently confirmed by high resolution electrospray ionization (ESI) mass spectra with positive (+) and/or negative (−) mode.

TABLE 4

Summary of sMAT reactions

| Analog | Percentage Turn-Over | Theoretical mass | Observed mass |
|---|---|---|---|
| HOOC-CH(NH₂)-CH₂-CH₂-S-CH₃ (methionine) | 100 | 399.1445, 297.0896[a] | 399.1444, 298.0965[b] |
| HOOC-CH(NH₂)-CH₂-CH₂-Se-CH₃ (selenomethionine) | 100 | 447.0890, 345.0340[a] | 447.0895, 346.0416[b] |
| –S–CH₂CH₃ | 84 | 413.1602, 311.1052[a] | 413.1599, 312.1121[b] |
| –Se–CH₂CH₃ | 76 | 461.1046, 359.0497[a] | 416.1040, 360.0565[b] |
| –S–CH₂–C≡CH | 36 | 321.0896[a] | 322.1051[b] |
| –Se–CH₂–C≡CH | 28 | 369.0340[a] | 370.0411[b] |
| –S–CH=C=CH₂ | ND | NA | NA |
| –S–CH₂–C≡N | 68 | 322.0848[a] | 323.0919[b] |
| –Se–CH₂–C≡N | 12 | 370.0293[a] | 371.0371[b] |
| –S–CH₂–CH=CH₂ | 27 | 425.1602, 323.1052[a] | 425.1609, 324.1129[b] |
| –Se–CH₂–CH=CH₂ | 30 | 371.0497[a] | 372.0568[b] |
| –S–CH₂CH₂CH₃ | 44 | 427.1758, 325.1209[a] | 427.1759, 326.1281[b] |
| –Se–CH₂CH₂CH₃ | 66 | 475.1203, 373.0653[a] | 475.1200, 374.0720[b] |
| –S–CH(CH₃)₂ | 53 | 427.1758, 325.1209[a] | 427.1762, 326.1282[b] |
| –Se–CH(CH₃)₂ | 40 | 373.0653[a] | 374.0743[b] |

TABLE 4-continued

Summary of sMAT reactions

| Analog | Percentage Turn-Over | Theoretical mass | Observed mass |
|---|---|---|---|
| S-CH2CH2C≡CH | 30 | 437.1602, 335.1052[a] | 437.1599, 336.1124[b] |
| Se-CH2CH2C≡CH | 10 | 383.0497[a] | 384.0566[b] |
| S-CH2CH=CHCH3 | 27 | 439.1758, 337.1209[a] | 439.1754, 338.1275[b] |
| S-CH2C(CH3)=CH2 | 15 | 439.1758, 337.1209[a] | 439.1754, 338.1282[b] |
| Se-CH2C(CH3)=CH2 | 46 | 385.0653[a] | 386.0730[b] |
| S-CH2CH2CH2CH3 | 27 | 441.1915, 339.1365[a] | 441.1966, 340.1477[b] |
| Se-CH2CH2CH2CH3 | 70 | 489.1359, 387.0810[a] | 489.1358, 388.0882[b] |
| S-CH2CH(CH3)2 | 57 | 441.1915, 339.1365[a] | 441.1918, 340.1439[b] |
| S-CH2CH2CH2NH2 | ND | NA | NA |
| Se-CH2CH2CH2NH2 | ND | NA | NA |
| S-CH2CH=CHCH=CH2 | 14 | 451.1758 | 451.1756 |
| S-CH2CH2N3 | 50 | 454.1616, 352.1066[a] | 454.1615, 353.1140[b] |
| S-CH2CH2CH(CH3)2 | 36 | 455.2071, 353.1522[a] | 455.2123, 354.1634[b] |
| S-CH2CH=C(CH3)2 | 12 | 453.1915 | 453.2044 |

TABLE 4-continued
Summary of sMAT reactions
| Analog | Percentage Turn-Over | Theoretical mass | Observed mass |
|---|---|---|---|
| 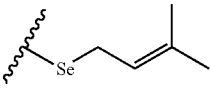 | 44 | 399.0810[a] | 400.0878[b] |
| 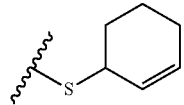 [SMILES: *SC1C=CCCC1] | ND | NA | NA |
| 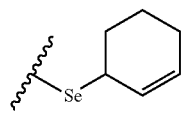 | ND | NA | NA |
| 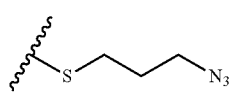 [SMILES: *SCCCN=[N+]=[N-]] | 60 | 468.1772, 366.1223[a] | 468.1772, 367.1296[b] |
| 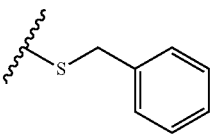 [SMILES: *SCc1ccccc1] | ND | NA | NA |
| 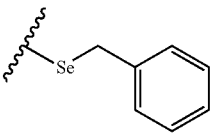 [SMILES: *[Se]Cc1ccccc1] | ND | NA | NA |
| 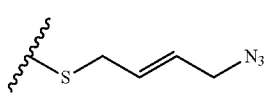 [SMILES: *SC/C=C/CN=[N+]=[N-]] | 28 | 480.1772, 378.1223[a] | 480.1768, 379.1292[b] |
| 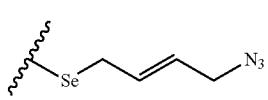 [SMILES: *[Se]C/C=C/CN=[N+]=[N-]] | 24 | 426.0667[a] | 427.0687[b] |
| 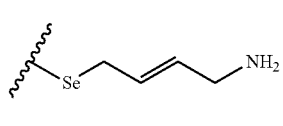 [SMILES: *[Se]C/C=C/CN] | 38 | 400.0762[a] | 401.0830[b] |
| 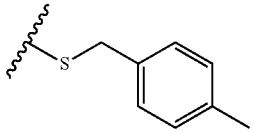 [SMILES: *SCc1ccc(C)cc1] | ND | NA | NA |
| 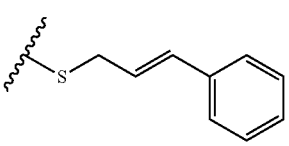 [SMILES: *SC/C=C/c1ccccc1] | ND | NA | NA |
| 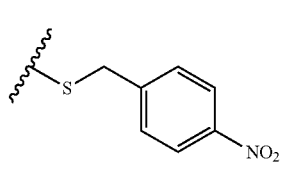 [SMILES: *SCc1ccc([N+](=O)[O-])cc1] | ND | NA | NA |

TABLE 4-continued

Summary of sMAT reactions

| Analog | Percentage Turn-Over | Theoretical mass | Observed mass |
|---|---|---|---|
| [Se-CH2-C6H4-NO2] | ND | NA | NA |
| [S-CH2CH2-S-CH2CH2-CH(NH2)-COOH] | ND | NA | NA |
| [S-CH2CH2CH2-S-CH2CH2-CH(NH2)-COOH] | ND | NA | NA |
| [S-CH2-CH=CH-CH2-S-CH2CH2-CH(NH2)-COOH] | ND | NA | NA |

[a]theoretical mass of degraded 5'-alkyl-thio(seleno)-5'-deoxyadenosine (MTA); observed mass of degraded 5'-alkyl thio(seleno)-5'-deoxyadenosine (MTA):
[b][M + H];
$^{ND}$not detected;
$^{NA}$not applicable.

RP-HPLC method: Reactions were quenched by the addition of equal volume of methanol followed by centrifugation at 10,000 g for 15 min to remove precipitated protein before applying on an analytical Varian ProStar HPLC [Luna $C_{18}$ column, 5 μm, 4.6 mm×250 mm; Phenomenex, Torrance, Calif., USA; gradient of 10% B to 40% B over 15 min, 40% B to 75% B over 5 min (A=10 mM $NaH_2PO_4$, 5 mM octane sulfonic acid, pH was adjusted to 3.5 using phosphoric acid; B=acetonitrile) flow rate=1 mL min$^{-1}$; $A_{254}$]. Reaction products were confirmed by HRMS.

Kinetic Measurements of sMAT Reactions: Pseudo first-order kinetics was assessed in triplicate under saturating ATP (2.5 mM) and variable L-methionine/L-ethionine (0.007, 0.013, 0.033, 0.066, 0.133, 0.333, 0.66, 1.33 mM) and saturating L-methionine/L-ethionine (2.5 mM) and variable ATP (0.013, 0.033, 0.066, 0.133, 0.333, 0.66, 1.33 mM) concentrations. Reactions were performed in buffer containing 25 mM Tris pH 8.0, 40 mM KCl and 5 mM $MgCl_2$, and 0.5 μg purified sMAT was added and incubated at 37° C. or 65° C. in a final volume of 20 μL. Reaction products were analyzed using RP-HPLC method above and product quantification was carried out using standard curve generated by commercial SAM. The kinetic curves were fit to the Michaelis-Menton equation using Prism software.

Example III

FIG. 19 illustrates a reaction catalyzed by MAT. Relatedly, FIG. 20 presents the synthesis of methionine-tetrazole (Met-T or T-Met), where: (a) is $(Boc)_2O$, pyridine, $NH_4HCO_3$, rt, 5 h, 70-8-%; (b) is $(TFA)_2O$: pyridine (1:1), THF, 0° C., 3 h, 85-95%; (c) is $NaN_3$, $ZnBr_2$, $H_2O$/2-propanol (2:1), 80° C., 16 h, 80-90%; and (d) is $Et_2NH$, $CH_2Cl_2$, 0.5 h, 80-94%. And FIG. 21 provides data illustrating the increased stability of SAM-T relative to native SAM.

REFERENCES

Throughout this document, various references are mentioned. All such references, including those listed below, are incorporated herein by reference in their entirety.

[1] a) S. S. Lamb, G. D. Wright, Proc. Natl. Acad. Sci. USA 2005, 102, 519-520; b) C. Olano, C. Mendez, J. A. Salas, Nat. Prod. Rep. 2010, 27, 571-616.
[2] a) J. J. Banik, J. W. Craig, P. Y. Calle, S. F. Brady, J. Am. Chem. Soc. 2010, 132, 15661-15670; b) S. J. Kwon, M. Mora-Pale, M. Y. Lee, J. S. Dordick, Curr. Opin. Chem. Biol. 2012, 16, 186-195; c) T. L. Li, Y. C. Liu, S. Y. Lyu, Curr. Opin. Chem. Biol. 2012, 16, 170-178.
[3] a) R. W. Gantt, P. Peltier-Pain, J. S. Thorson, Nat. Prod. Rep. 2011, 28, 1811-1853; b) R. W. Gantt, P. Peltier-Pain, W. J. Cournoyer, J. S. Thorson, Nat. Chem. Biol. 2011, 7, 685-691; c) R. W. Gantt, P. Peltier-Pain, S. Singh, M. Zhou, J. S. Thorson, Proc. Natl. Acad. Sci. USA May 2013, 110, 7648-7653; d) M. Zhou, A. Hamza, C.-G. Zhan, J. S. Thorson, J. Nat. Prod. 2013, 76, 279-286; e) P. Peltier-Pain, K. Marchillo, M. Zhou, D. R. Andes, J. S. Thorson. Org. Lett. 2012, 14, 5086-5089.
[4] D. K. Liscombe, G. V. Louie, J. P. Noel, Nat. Prod. Rep. 2012, 29, 1238-1250.
[5] a) C. Zhang, R. L. Weller, J. S. Thorson, S. R. Rajski, J. Am. Chem. Soc. 2006, 128, 2760-2761; b) H. Stecher, M. Tengg, B. J. Ueberbacher, P. Remler, H. Schwab, H. Griengl, M. Gruber-Khadjawi, Angew. Chem. Int. Ed. Engl. 2009, 48, 9546-9548.
[6] a) K. Islam, W. Zheng, H. Yu, H. Deng, M. Luo, ACS Chem. Biol. 2011, 6, 679-684; b) R. Wang, W. Zheng, H. Yu, H. Deng, M. Luo, J. Am. Chem. Soc. 2011, 133, 7648-7651; c) I. R. Bothwell, K. Islam, Y. Chen, W. Zheng, G. Blum, H. Deng, M. Luo, J. Am. Chem. Soc. 2012, 134, 14905-14912; d) S. Willnow, M. Martin, B. Luscher, E. Weinhold, Chem bio chem. 2012, 13, 1167-

1173; e) R. Wang, K. Islam, Y. Liu, W. Zheng, H. Tang, N. Lailler, G. Blum, H. Deng, M. Luo, *J. Am. Chem. Soc.* January 2013, 135, 1048-1056.

[7] a) C. Dalhoff, G. Lukinavicius, S. Klimasauskas, E. Weinhold, *Nat. Prot.* 2006, 1, 1879-1886; b) C. Dalhoff, G. Lukinavicius, S. Klimasauskas, E. Weinhold, *Nat. Chem. Biol.* 2006, 2, 31-32; c) S. Klimasauskas, E. Weinhold, *Trends Biotechnol.* 2007, 25, 99-104; d) G. Lukinavicius, V. Lapiene, Z. Stasevskij, C. Dalhoff, E. Weinhold, S. Klimasauskas, *J. Am. Chem. Soc.* 2007, 129, 2758-2759; e) C. Dalhoff, M. Huben, T. Lenz, P. Poot, E. Nordhoff, H. Koster, E. Weinhold, *Chem bio chem.* 2010, 11, 256-265; f) Y. Motorin, J. Burhenne, R. Teimer, K. Koynov, S. Willnow, E. Weinhold, M. Helm, *Nucleic Acids Res.* 2011, 39, 1943-1952.

[8] P. M. Ueland, *Pharmacol. Rev.* 1982, 34, 223-285.

[9] a) Z. J. Lu, G. D. Markham, *J. Biol. Chem.* 2002, 277, 16624-16631; b) O. M. Ottink, F. H. Nelissen, Y. Derks, S. S. Wijmenga, H. A. Heus, *Anal. Biochem.* 2010, 396, 280-283.

[10] a) C. Sanchez, I. A. Butovich, A. F. Brana, J. Rohr, C. Mendez, J. A. Salas, *Chem. Biol.* 2002, 9, 519-53; b) C. G. Hyun, T. Bililign, J. C. Liao, J. S. Thorson, *Chem bio chem.* 2003, 4, 114-117; c) C. Zhang, C. Albermann, X. Fu, N. R. Peters, J. D. Chisholm, G. Zhang, E. J. Gilbert, P. G. Wang, D. L. Van Vranken, J. S. Thorson, *Chem bio chem.* 2006, 7, 795-804; d) S. Singh, J. G. McCoy, C. Zhang, C. A. Bingman, G. N. Phillips, Jr., J. S. Thorson, *J. Biol. Chem.* 2008, 283, 22628-22636.

[11] a) D. F. Iwig, S. J. Booker, *Biochemistry,* 2004, 43, 13496-13509; b) D. F. Iwig, A. T. Grippe, T. A. McIntyre, S. J. Booker, *Biochemistry,* 2004, 43, 13510-13524.

[12] a) J. Jiracek, M. Collinsova, I. Rosenberg, M. Budesinsky, E. Protivinska, H. Netusilova, T. A. Garrow, *J. Med. Chem.* 2006, 49, 3982-3989; b) Y. Yi, S. X. Fa, W. Cao, L. W. Zeng, M. X. Wang, H. P. Xu, X. Zhang, *Chem. Commun.* 2012, 48, 7495-7497.

[13] R. L. Strausberg, E. A. Feingold, L. H. Grouse, J. G. Derge, R. D. Klausner, F. S. Collins, L. Wagner, C. M. Shenmen, G. D. Schuler, S. F. Altschul, B. Zeeberg, K. H. Buetow, C. F. Schaefer, N. K. Bhat, R. F. Hopkins, H. Jordan, T. Moore, S. I. Max, J. Wang, F. Hsieh, L. Diatchenko, K. Marusina, A. A. Farmer, G. M. Rubin, L. Hong, M. Stapleton, M. B. Soares, M. F. Bonaldo, T. L. Casavant, T. E. Scheetz, M. J. Brownstein, T. B. Usdin, S. Toshiyuki, P. Carninci, C. Prange, S. S. Raha, N. A. Loquellano, G. J. Peters, R. D. Abramson, S. J. Mullahy, S. A. Bosak, P. J. McEwan, K. J. McKernan, J. A. Malek, P. H. Gunaratne, S. Richards, K. C. Worley, S. Hale, A. M. Garcia, L. J. Gay, S. W. Hulyk, D. K. Villalon, D. M. Muzny, E. J. Sodergren, X. H. Lu, R. A. Gibbs, J. Fahey, E. Helton, M. Ketteman, A. Madan, S. Rodrigues, A. Sanchez, M. Whiting, A. Madan, A. C. Young, Y. Shevchenko, G. G. Bouffard, R. W. Blakesley, J. W. Touchman, E. D. Green, M. C. Dickson, A. C. Rodriguez, J. Grimwood, J. Schmutz, R. M. Myers, Y. S. N. Butterfield, M. I. Kryzywinski, U. Skalska, D. E. Smailus, A. Schnerch, J. E. Schein, S. J. M. Jones, M. A. Marra, M. G. C. M. Pro, *Proc. Natl. Acad. Sci. USA,* 2002, 99, 16899-16903.

[14] G. D. Markham, J. Deparasis, J. Gatmaitan, *J. Biol. Chem.* 1984, 259, 4505-4507.

[15] C. J. Bult, O. White, G. J. Olsen, L. X. Zhou, R. D. Fleischmann, G. G. Sutton, J. A. Blake, L. M. FitzGerald, R. A. Clayton, J. D. Gocayne, A. R. Kerlavage, B. A. Dougherty, J. F. Tomb, M. D. Adams, C. I. Reich, R. Overbeek, E. F. Kirkness, K. G. Weinstock, J. M. Merrick, A. Glodek, J. L. Scott, N. S. M. Geoghagen, J. F. Weidman, J. L. Fuhrmann, D. Nguyen, T. R. Utterback, J. M. Kelley, J. D. Peterson, P. W. Sadow, M. C. Hanna, M. D. Cotton, K. M. Roberts, M. A. Hurst, B. P. Kaine, M. Borodovsky, H. P. Klenk, C. M. Fraser, H. O. Smith, C. R. Woese, J. C. Venter, *Science,* 1996, 273, 1058-1073.

[16] S. C. Lu, J. M. Mato, *Physio. Rev.* 2012, 92, 1515-1542.

[17] N. Yarlett, J. Garofalo, B. Goldberg, M. A. Ciminelli, V. Ruggiero, J. R. Sufrin, C. J. Bacchi, *Biochim. Biophys. Acta* 1993, 1181, 68-76.

[18] Hoffman, J. L. (1986). Chromatographic analysis of the chiral and covalent instability of S-adenosyl-L-methionine. Biochemistry 25, 4444-4449.

[19] H. L. LeGros, Jr., A. B. Halim, A. M. Geller, M. Kotb, *J. Biol. Chem.* 2000, 275, 2359-2366.

[20] J. K. Coward, E. P. Slisz, *J. Med. Chem.* 1973, 16, 460-463.

[21] a) H. Yang, Z. Z. Huang, J. Wang, S. C. Lu, *FASEB* 2001, 15, 1507-1516; b) H. Chen, M. Xia, M. Lin, H. P. Yang, J. Kuhlenkamp, T. Li, N. M. Sodir, Y. H. Chen, H. Josef-Lenz, P. W. Laird, S. Clarke, J. M. Mato, S. C. Lu, *Gastroenterology* 2007, 133, 207-218. c) T. Zhang, Z. C. Zheng, Y. Q. Liu, J. J. Zhang, Y. Zhao, Y. Liu, H. T. Zhu, G. H. Zhao, J. W. Liang, Q. Li, H. M. Xu, *Acta Histochem* January 2013, 115, 48-55.

[22] a) Q. Liu, K. Wu, Y. Zhu, Y. He, J. Wu, Z. Liu, *Hepatology Res.* 2007, 37, 376-388; b) W. Zhang, V. Sviripa, X. Chen, J. Shi, T. Yu, A. Hamza, N. D. Ward, L. M. Kril, C. W. Vander Kooi, C. G. Zhan, B. M. Evers, D. S. Watt, C. Liu, *ACS Chem. Biol.* April 2013, 8, 796-803.

[23] a) W. A. Barton, J. Lesniak, J. B. Biggins, P. D. Jeffrey, J. Jiang, K. R. Rajashankar, J. S. Thorson, D. B. Nikolov, *Nat. Struct. Biol.* 2001, 8, 545-551; b) W. A. Barton, J. B. Biggins, J. Jiang, J. S. Thorson, D. B. Nikolov *Proc. Natl. Acad. Sci. USA* 2002, 99, 13397-13402; c) D. Hoffmeister, J. Yang, L. Liu, J. S. Thorson, *Proc. Natl. Acad. Sci. USA* 2003, 100, 13184-13189; d) J. Yang, L. Liu, J. S. Thorson, *Chem bio chem.* 2004, 5, 992-996; e) J. Yang, X. Fu, J. Liao, L. Liu, J. S. Thorson, *Chem & Biol* 2005, 12, 657-664; f) R. Moretti, J. S. Thorson, *J. Biol. Chem.* 2007, 282, 16942-16947; g) G. J. Williams, C. Zhang, J. S. Thorson, *Nat. Chem. Biol.* 2007, 3, 657-662; h) R. Moretti, A. Chang, P. Peltier-Pain, C. A. Bingman, G. N. Phillips, Jr., J. S. Thorson, *J. Biol. Chem.* 2011, 286, 13235-13243.

[24] T. Shiraiwa, K. Nakagawa, N. Kanemoto, T. Kinda, H. Yamamoto, *Chem. Pharm. Bull.* 2002, 50, 1081-1085.

[25] Z. S. Zhou, E. Smith, R. G. Matthews, *Bioorg. Med. Chem. Lett.* 2000, 10, 2471-2475.

[26] Y. Yi, S. Fa, W. Cao, L. Zeng, M. Wang, H. Xu, X. Zhang, *Chem. Commun.* 2012, 48, 7495-7497.

[27] C. A. Dekker, J. S. Fruton, *J. Biol. Chem.* 1948, 173, 471-477.

[28] K. Sato, M. Hirayama, *Bull. Chem. Soc. Jpn.* 1969, 42, 2589-2592.

[29] K. Islam, I. Bothwell, Y. Chen, C. Sengelaub, R. Wang, H. Deng, M. Luo, *J. Am. Chem. Soc.* 2012, 134, 5909-5915.

[30] J. D. Chisholm, D. L. Van Vranken, *J. Org. Chem.* 2000, 65, 7541-7553.

[31] Adams, P. D., Afonine, P. V., Bunkoczi, G., Chen, V. B., Davis, I. W., Echols, N., Headd, J. J., Hung, L. W., Kapral, G. J., Grosse-Kunstleve, R. W., et al. (2010). PHENIX: a comprehensive Python-based system for macromolecular structure solution. Acta Crystallogr D 66, 213-221.

[32] Chen, V. B., Arendall, W. B., 3rd, Headd, J. J., Keedy, D. A., Immormino, R. M., Kapral, G. J., Murray, L. W.,

[33] Emsley, P., Lohkamp, B., Scott, W. G., and Cowtan, K. (2010). Features and development of Coot. Acta Crystallogr D 66, 486-501.

[34] Fu, Z., Hu, Y., Markham, G. D., and Takusagawa, F. (1996). Flexible loop in the structure of S-adenosylmethionine synthetase crystallized in the tetragonal modification. Journal of biomolecular structure & dynamics 13, 727-739.

[35] Gonzalez, B., Pajares, M. A., Hermoso, J. A., Alvarez, L., Garrido, F., Sufrin, J. R., and Sanz-Aparicio, J. (2000). The crystal structure of tetrameric methionine adenosyltransferase from rat liver reveals the methionine-binding site. Journal of molecular biology 300, 363-375.

[36] Gonzalez, B., Pajares, M. A., Hermoso, J. A., Guillerm, D., Guillerm, G., and Sanz-Aparicio, J. (2003). Crystal structures of methionine adenosyltransferase complexed with substrates and products reveal the methionine-ATP recognition and give insights into the catalytic mechanism. Journal of molecular biology 331, 407-416.

[37] Graham, D. E., Bock, C. L., Schalk-Hihi, C., Lu, Z. J., and Markham, G. D. (2000). Identification of a highly diverged class of S-adenosylmethionine synthetases in the archaea. The Journal of biological chemistry 275, 4055-4059.

[38] Holm, L., and Rosenstrom, P. (2010). Dali server: conservation mapping in 3D. Nucleic acids research 38, W545-549.

[39] Kabsch, W. (2010). Xds. Acta Crystallogr D 66, 125-132.

[40] Komoto, J., Yamada, T., Takata, Y., Markham, G. D., and Takusagawa, F. (2004). Crystal structure of the S-adenosylmethionine synthetase ternary complex: a novel catalytic mechanism of S-adenosylmethionine synthesis from ATP and Met. Biochemistry 43, 1821-1831.

[41] Krissinel, E., and Henrick, K. (2007). Inference of macromolecular assemblies from crystalline state. Journal of molecular biology 372, 774-797.

[42] Lu, S. C., and Mato, J. M. (2008). S-Adenosylmethionine in cell growth, apoptosis and liver cancer. Journal of gastroenterology and hepatology 23 Suppl 1, S73-77.

[43] Markham, G. D., and Pajares, M. A. (2009). Structure-function relationships in methionine adenosyltransferases. Cellular and molecular life sciences: CMLS 66, 636-648.

[44] Mato, J. M., Alvarez, L., Ortiz, P., and Pajares, M. A. (1997). S-adenosylmethionine synthesis: molecular mechanisms and clinical implications. Pharmacology & therapeutics 73, 265-280.

[45] Mudd, S. H., and Cantoni, G. L. (1958). Activation of Methionine for Transmethylation 0.3. Methionine-Activating Enzyme of Bakers Yeast. Journal of Biological Chemistry 231, 481-492.

[46] Otwinowski, Z., and Minor, W. (1997). Processing of X-ray diffraction data collected in oscillation mode. Method Enzymol 276, 307-326.

[47] Porcelli, M., Cacciapuoti, G., Carteni-Farina, M., and Gambacorta, A. (1988). S-adenosylmethionine synthetase in the thermophilic archaebacterium Sulfolobus solfataricus. Purification and characterization of two isoforms. European journal of biochemistry/FEBS 177, 273-280.

[48] Schrodinger, LLC (2010). The PyMOL Molecular Graphics System, Version 1.3r1.

[49] Shafqat, N., Muniz, J. R., Pilka, E. S., Papagrigoriou, E., von Delft, F., Oppermann, U., and Yue, W. W. (May 2013). Insight into S-adenosylmethionine biosynthesis from the crystal structures of the human methionine adenosyltransferase catalytic and regulatory subunits. The Biochemical journal 452, 27-36.

[50] Sreenath, H. K., Bingman, C. A., Buchan, B. W., Seder, K. D., Burns, B. T., Geetha, H. V., Jeon, W. B., Vojtik, F. C., Aceti, D. J., Frederick, R. O., et al. (2005). Protocols for production of selenomethionine-labeled proteins in 2-L polyethylene terephthalate bottles using auto-induction medium. Protein expression and purification 40, 256-267.

[51] Takusagawa, F., Kamitori, S., and Markham, G. D. (1996a). Structure and function of S-adenosylmethionine synthetase: crystal structures of S-adenosylmethionine synthetase with ADP, BrADP, and PPi at 28 angstroms resolution. Biochemistry 35, 2586-2596.

[52] Takusagawa, F., Kamitori, S., Misaki, S., and Markham, G. D. (1996b). Crystal structure of S-adenosylmethionine synthetase. The Journal of biological chemistry 271, 136-147.

[53] Taylor, J. C., and Markham, G. D. (2003). Conformational dynamics of the active site loop of S-adenosylmethionine synthetase illuminated by site-directed spin labeling. Archives of biochemistry and biophysics 415, 164-171.

[54] Taylor, J. C., Takusagawa, F., and Markham, G. D. (2002). The active site loop of S-adenosylmethionine synthetase modulates catalytic efficiency. Biochemistry 41, 9358-9369.

[55] Wang, R., Islam, K., Liu, Y., Zheng, W., Tang, H., Lailler, N., Blum, G., Deng, H., and Luo, M. (January 2013). Profiling genome-wide chromatin methylation with engineered posttranslation apparatus within living cells. Journal of the American Chemical Society 135, 1048-1056.

[56] Willnow, S., Martin, M., Luscher, B., and Weinhold, E. (2012). A selenium-based click AdoMet analogue for versatile substrate labeling with wild-type protein methyltransferases. Chem bio chem: a European journal of chemical biology 13, 1167-1173.

[57] Zhang, C.; Weller, R. L.; Thorson, J. S.; Rajski, S. R. Journal of the American Chemical Society 2006, 128, 2760-1.

[58] Pljevaljcic, G.; Pignot, M.; Weinhold, E. Journal of the American Chemical Society 2003, 125, 3486-92.

[59] Ibáñez, G.; McBean, J. L.; Astudillo, Y. M.; Luo, M. Analytical Biochemistry 2010, 401, 203-10.

Sequence Listing Free Text

SEQ ID NO: 1 is the DNA sequence of synthetic *Methanocaldococcus jannaschii* MAT (mMAT) gene where the bold letters indicate engineered restriction sites for subcloning (5'-NdeI and 3'-EcoRI).

5'-CATATGCGTAATATCATTGTGAAAAAACTGGATGTGGAACCGATTGA

AGAACGCCCGACGGAAATTGTTGAACGTAAAGGTCTGGGTCATCCGGATT

CAATTTGCGACGGTATCGCCGAAAGCGTGTCTCGCGCACTGTGTAAAATG

TACATGGAAAAGTTTGGCACGATTCTGCATCACAATACCGATCAGGTCGA

ACTGGTGGGCGGTCATGCTTATCCGAAGTTTGGCGGTGGCGTCATGGTGT

CACCGATTTACATCCTGCTGTCGGGTCGTGCAACCATGGAAATCCTGGAT

```
AAGGAAAAGAATGAAGTCATCAAGCTGCCGGTGGGTACCACGGCAGTTAA
AGCAGCCAAGGAATATCTGAAAAAGGTCCTGCGTAACGTTGATGTCGACA
AAGATGTTATTATCGATTGCCGCATTGGTCAGGGCAGCATGGACCTGGTG
GATGTTTTTGAACGCCAGAAAAACGAAGTGCCGCTGGCTAACGACACGAG
TTTCGGTGTTGGCTACGCGCCGCTGTCCACCACGGAACGTCTGGTGCTGG
AAACCGAACGTTTTCTGAACAGCGATGAACTGAAAAACGAAATCCCGGCG
GTTGGTGAAGACATTAAAGTCATGGGTCTGCGTGAAGGCAAAAAGATTAC
CCTGACGATCGCGATGGCCGTGGTTGATCGCTATGTGAAGAACATCGAAG
AATACAAAGAAGTGATCGAAAAGGTTCGTAAAAAGGTCGAAGATCTGGCA
AAAAAGATCGCTGACGGCTATGAAGTTGAAATCCACATTAACACGGCCGA
TGACTATGAACGCGAATCCGTGTACCTGACCGTTACGGGTACCAGCGCAG
AAATGGGTGATGACGGCTCTGTGGGTCGTGGCAACCGCGTTAATGGCCTG
ATTACCCCGTTCCGTCCGATGAGTATGGAAGCAGCTTCCGGTAAAAACCC
```

```
GGTTAATCACGTCGGCAAGATTTATAACATCCTGGCGAATCTGATTGCCA
ACGATATCGCAAAACTGGAAGGTGTCAAGGAATGTTACGTGCGTATTCTG
TCACAAATCGGCAAACCGATTAATGAACCGAAGGCCCTGGATATCGAAAT
TATCACCGAAGACTCGTACGATATTAAAGACATCGAACCGAAAGCTAAGG
AAATTGCGAACAAATGGCTGGACAACATTATGGAAGTTCAGAAGATGATC
GTCGAAGGCAAGGTCACCACGTTTTGAGAATTC-3'
```

SEQ ID NO: 2 is

5'-ATACTGCATATGGCAAAACACCTTTTTACG (forward, NdeI).

SEQ ID NO: 2 is

5'-CAGTATGGATCCTTACTTCAGACCGGCAGC (reverse, BamHI).

What is claimed is:

1. An S-adenosyl-L-methionine (SAM) or Se-adenosyl-L-methionine (SeAM) analog of the Formula III:

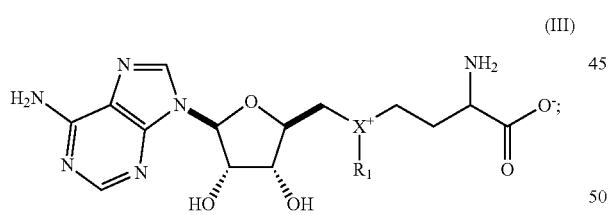

wherein X is selected from the group consisting of S and Se;

wherein, when X is S, $R_1$ is selected from the group consisting of:

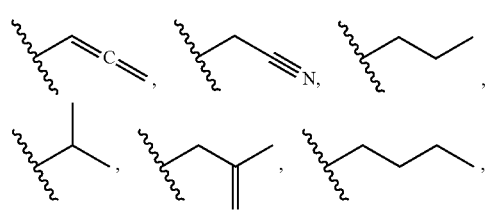

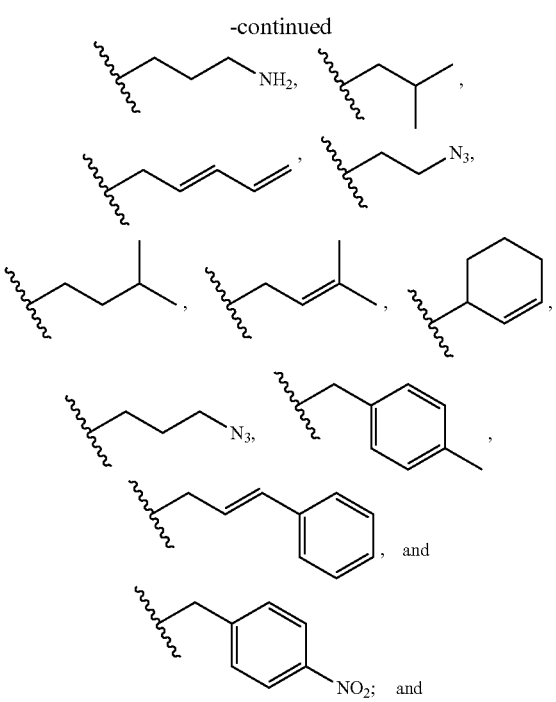

, and

, and wherein, when X is Se, $R_1$ is selected from the group consisting of:

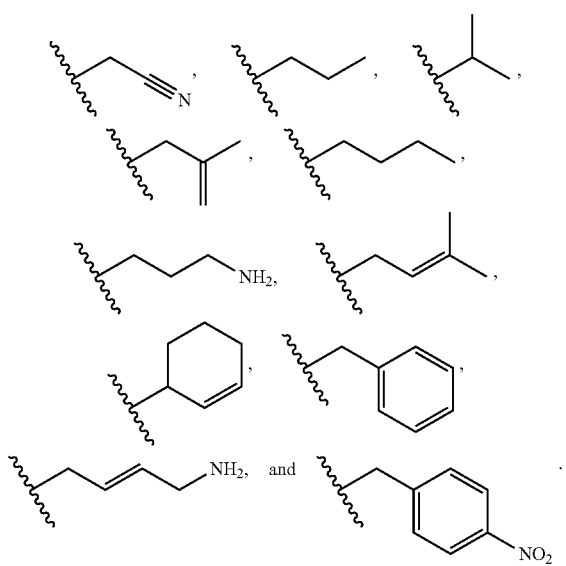

2. A compound of the Formula II:

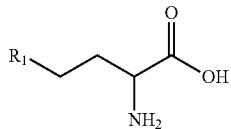

wherein $R_1$ is selected from the group consisting of

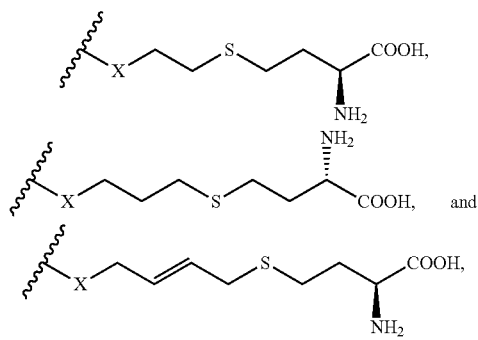

and X is S.

3. An S-adenosyl-L-methionine analog of the Formula III:

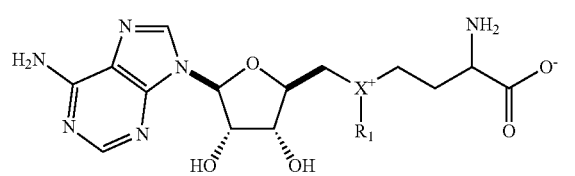

wherein X is S and $R_1$ is selected from the group consisting of:

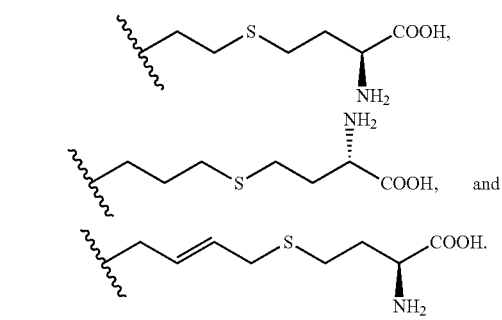

4. An S-adenosyl-L-methionine (SAM) analog of the formula:

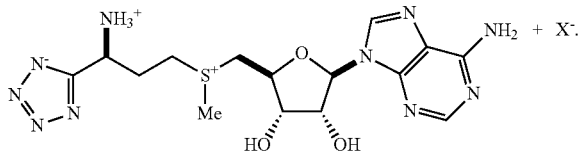

5. A method of producing an S-adenosyl-L-methionine analog according to claim 4, comprising the step of reacting a first substrate comprising methionine-tetrazole with a second substrate comprising adenosine triphosphate (ATP) in the presence of a methionine adenosyltransferase (MAT).

6. The method of claim 5, wherein the MAT comprises at least one of human MAT II catalytic alpha and regulatory beta subunit (hMAT2), human MAT II catalytic alpha subunit alone (hMAT2A), human MAT I catalytic subunit alpha (hMAT1A), *Escherichia coli* MAT (eMAT), *Sulfolobus solfataricus* MAT (sMAT), and *Methanocaldococcus jannaschii* MAT (mMAT).

7. A method of producing the S-adenosyl-L-methionine analog of claim 1, comprising the step of reacting a first substrate comprising a methionine analog with a second substrate comprising adenosine triphosphate (ATP) in the presence of a methionine adenosyltransferase (MAT).

8. The method of claim 7, wherein the MAT comprises at least one of human MAT II catalytic alpha and regulatory beta subunit (hMAT2), human MAT II catalytic alpha subunit alone (hMAT2A), human MAT I catalytic subunit alpha (hMAT1A), *Escherichia coli* MAT (eMAT), *Sulfolobus solfataricus* MAT (sMAT), and *Methanocaldococcus jannaschii* MAT (mMAT).

9. The method of claim 7, wherein the first substrate is of the Formula II:

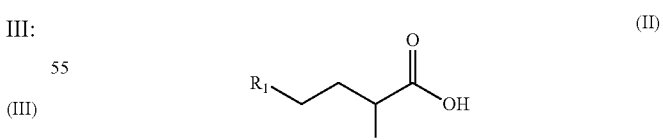

wherein $R_1$ is selected from the group consisting of

-continued

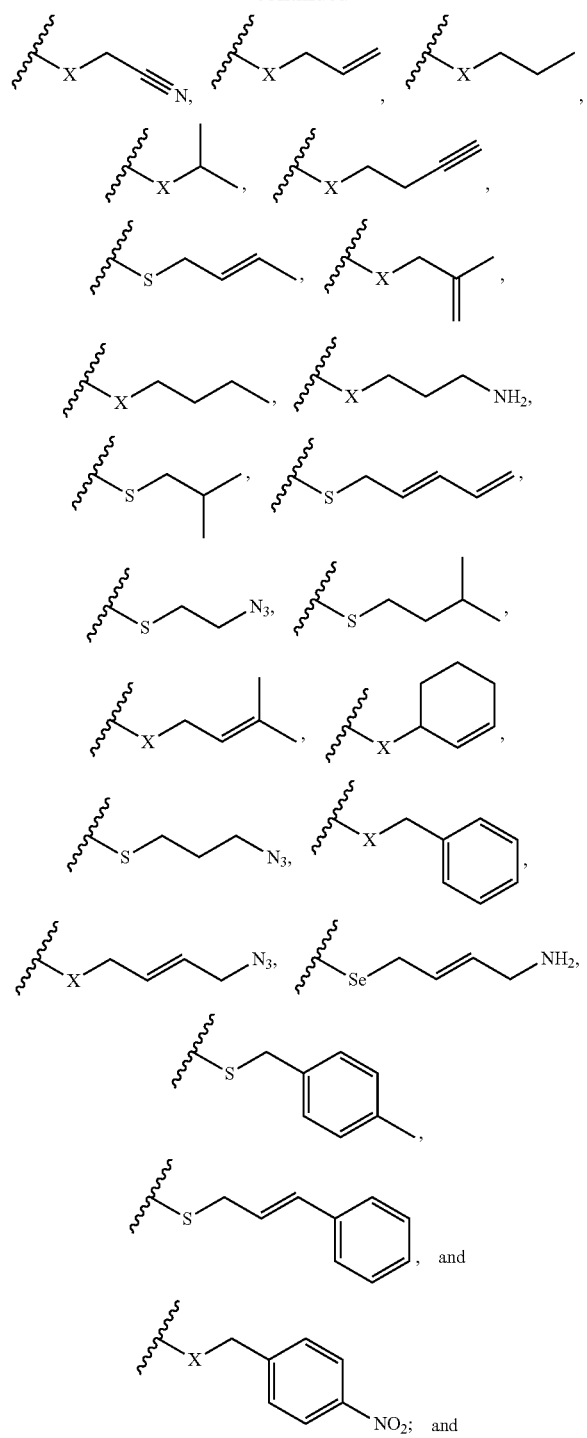

wherein X is S.

10. A method of producing the Se-adenosyl-L-methionine analog of claim 1, comprising the step of reacting a first substrate comprising a methionine analog with a second substrate comprising adenosine triphosphate (ATP) in the presence of a methionine adenosyltransferase (MAT).

11. The method of claim 10, wherein the first substrate is of the Formula II:

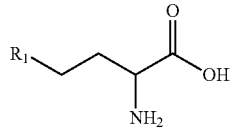
(II)

wherein $R_1$ is selected from the group consisting of

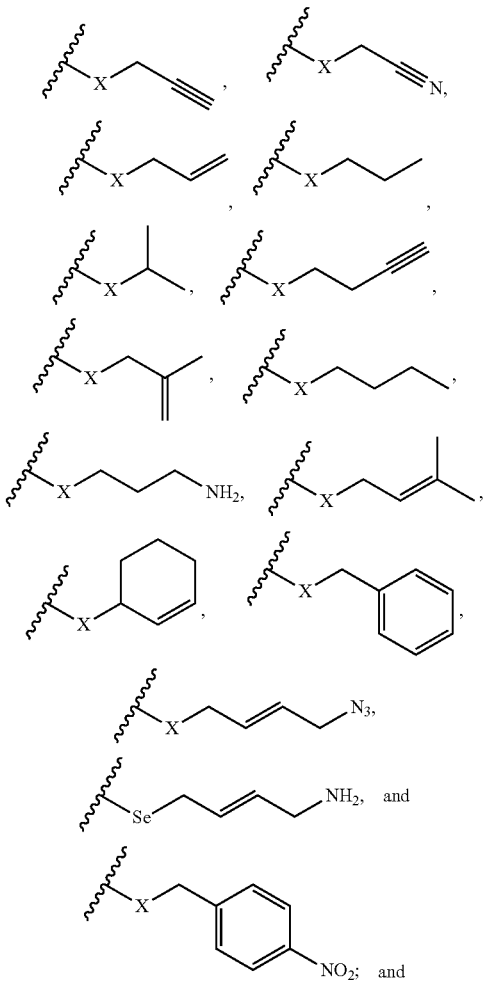

wherein X is Se.

12. A method of producing an indolocarbazole analog, comprising the step of reacting a first substrate comprising a methionine analog with a second substrate in the presence of a methionine adenosyltransferase (MAT), wherein the methionine analog is of the Formula II:

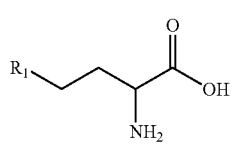
(II)

wherein $R_1$ is selected from the group consisting of

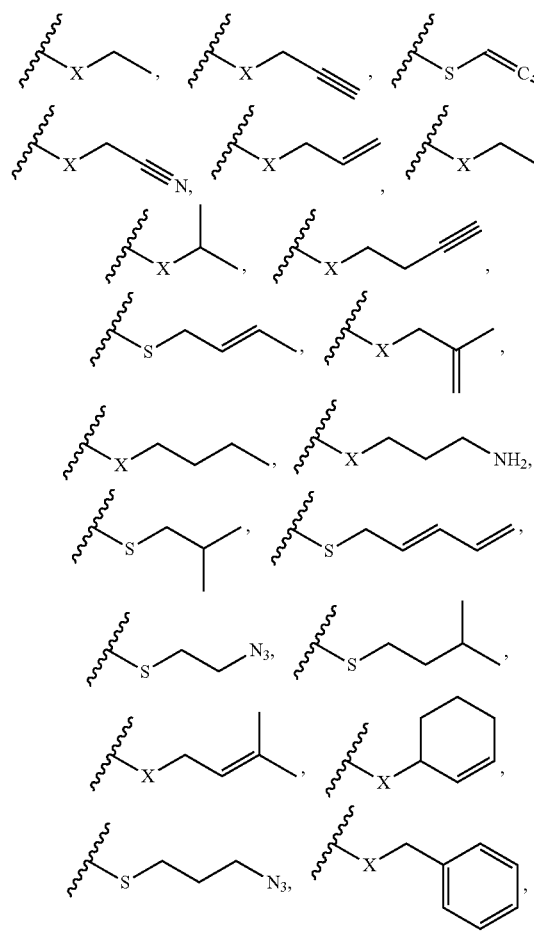

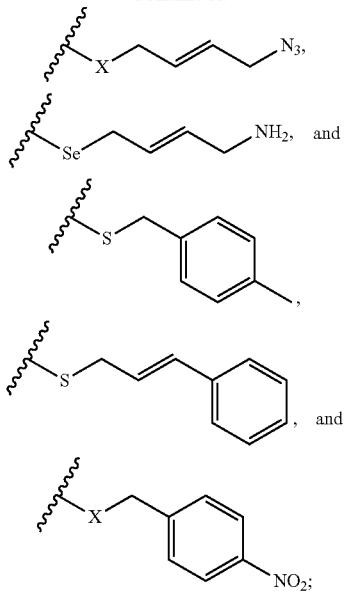

wherein X is selected from the group consisting of S and Se; and wherein the second substrate comprises at least one indolocarbazole group.

13. The method of claim 12, wherein the MAT comprises at least one of human MAT II catalytic alpha and regulatory beta subunit (hMAT2), human MAT II catalytic alpha subunit alone (hMAT2A), human MAT I catalytic subunit alpha (hMAT1A), *Escherichia coli* MAT (eMAT), *Sulfolobus solfataricus* MAT (sMAT), and *Methanocaldococcus jannaschii* MAT (mMAT).

* * * * *

SEQUENCE LISTING

<160> NUMBER OF SEQ ID NOS: 5

<210> SEQ ID NO 1
<211> LENGTH: 1230
<212> TYPE: DNA
<213> ORGANISM: Methanocaldococcus jannaschii

<400> SEQUENCE: 1

```
catatgcgta atatcattgt gaaaaaactg gatgtggaac cgattgaaga acgcccgacg    60
gaaattgttg aacgtaaagg tctgggtcat ccggattcaa tttgcgacgg tatcgccgaa   120
agcgtgtctc gcgcactgtg taaaatgtac atggaaaagt tggcacgat tctgcatcac   180
aataccgatc aggtcgaact ggtgggcggt catgcttatc gaagtttgg cggtggcgtc   240
atggtgtcac cgatttacat cctgctgtcg ggtcgtgcaa ccatggaaat cctggataag   300
gaaaagaatg aagtcatcaa gctgccggtg gtaccacgg cagttaaagc agccaaggaa   360
tatctgaaaa aggtcctgcg taacgttgat gtcgacaaag atgttattat cgattgccgc   420
attggtcagg gcagcatgga cctggtggat gttttgaac gccagaaaaa cgaagtgccg   480
ctggctaacg acacgagttt cggtgttggc tacgcgccgc tgtccaccac ggaacgtctg   540
gtgctggaaa ccgaacgttt tctgaacagc gatgaactga aaaacgaaat cccggcggtt   600
ggtgaagaca ttaaagtcat gggtctgcgt gaaggcaaaa agattaccct gacgatcgcg   660
atggccgtgg ttgatcgcta tgtgaagaac atcgaagaat acaaagaagt gatcgaaaag   720
gttcgtaaaa aggtcgaaga tctggcaaaa aagatcgctg acggctatga agttgaaatc   780
cacattaaca cggccgatga ctatgaacgc gaatccgtgt acctgaccgt tacgggtacc   840
agcgcagaaa tgggtgatga cggctctgtg ggtcgtggca accgcgttaa tggcctgatt   900
accccgttcc gtccgatgag tatggaagca gcttccggta aaaacccggt taatcacgtc   960
ggcaagattt ataacatcct ggcgaatctg attgccaaca tatcgcaaa actggaaggt  1020
gtcaaggaat gttacgtgcg tattctgtca caaatcggca aaccgattaa tgaaccgaag  1080
gccctggata tcgaaattat caccgaagac tcgtacgata ttaaagacat cgaaccgaaa  1140
gctaaggaaa ttgcgaacaa atggctggac aacattatgg aagttcagaa gatgatcgtc  1200
```

```
gaaggcaagg tcaccacgtt ttgagaattc                                          1230

<210> SEQ ID NO 2
<211> LENGTH: 30
<212> TYPE: DNA
<213> ORGANISM: Neisseria denitrificans

<400> SEQUENCE: 2
atactgcata tggcaaaaca ccttttttacg                                           30

<210> SEQ ID NO 3
<211> LENGTH: 30
<212> TYPE: DNA
<213> ORGANISM: Bacillus amyloliquefaciens

<400> SEQUENCE: 3
cagtatggat ccttacttca gaccggcagc                                           30

<210> SEQ ID NO 4
<211> LENGTH: 28
<212> TYPE: DNA
<213> ORGANISM: Neisseria denitrificans

<400> SEQUENCE: 4
agccatatga aaatcggcat cattggtg                                             28

<210> SEQ ID NO 5
<211> LENGTH: 30
<212> TYPE: DNA
<213> ORGANISM: Excherichia coli

<400> SEQUENCE: 5
atagaattct tagccatgtg caagtttctg                                           30
```